US011397182B2

(12) United States Patent
Lyden et al.

(10) Patent No.: US 11,397,182 B2
(45) Date of Patent: Jul. 26, 2022

(54) METHODS FOR PROGNOSING AND PREVENTING METASTATIC LIVER DISEASE

(71) Applicant: CORNELL UNIVERSITY, Ithaca, NY (US)

(72) Inventors: David C. Lyden, New York, NY (US); Bruno Costa Da Silva, Lisbon (PT)

(73) Assignee: CORNELL UNIVERSITY, Ithaca, NY (US)

( * ) Notice: Subject to any disclaimer, the term of this patent is extended or adjusted under 35 U.S.C. 154(b) by 134 days.

(21) Appl. No.: 15/517,697

(22) PCT Filed: Oct. 7, 2015

(86) PCT No.: PCT/US2015/054538
§ 371 (c)(1),
(2) Date: Apr. 7, 2017

(87) PCT Pub. No.: WO2016/057702
PCT Pub. Date: Apr. 14, 2016

(65) Prior Publication Data
US 2018/0231558 A1 Aug. 16, 2018

Related U.S. Application Data

(60) Provisional application No. 62/060,925, filed on Oct. 7, 2014.

(51) Int. Cl.
G01N 33/00 (2006.01)
G01N 33/574 (2006.01)
C12Q 1/6886 (2018.01)

(52) U.S. Cl.
CPC ..... *G01N 33/57438* (2013.01); *C12Q 1/6886* (2013.01); *C12Q 2600/118* (2013.01); *C12Q 2600/158* (2013.01); *G01N 2333/46* (2013.01); *G01N 2333/70557* (2013.01); *G01N 2333/70585* (2013.01); *G01N 2333/70596* (2013.01); *G01N 2333/715* (2013.01); *G01N 2333/90245* (2013.01); *G01N 2333/96494* (2013.01); *G01N 2800/50* (2013.01)

(58) Field of Classification Search
CPC ............... G01N 33/57438; G01N 2800/50
See application file for complete search history.

(56) References Cited

U.S. PATENT DOCUMENTS

| | | | |
|---|---|---|---|
| 5,849,701 A | 12/1998 | Roberts et al. | |
| 6,492,428 B1 | 12/2002 | Al-Abed et al. | |
| 6,599,938 B1 | 7/2003 | Al-Abed et al. | |
| 7,147,852 B2 | 12/2006 | Gilbertson | |
| 7,365,200 B2 | 4/2008 | Sircar et al. | |
| 7,435,737 B2 | 10/2008 | Gaeta et al. | |
| 7,491,740 B2 | 2/2009 | Al-Abed | |
| 7,511,056 B2 | 3/2009 | Diefenbacher et al. | |
| 8,158,589 B2 | 4/2012 | Dotor Herrerias et al. | |
| 8,552,040 B2 | 10/2013 | Al-Abed | |
| 8,569,462 B2 | 10/2013 | Bedinger et al. | |
| 8,691,944 B2 | 4/2014 | Clark et al. | |
| 9,816,998 B2 | 11/2017 | Lyden et al. | |
| 9,921,223 B2 | 3/2018 | Kalluri et al. | |
| 2008/0113997 A1 | 5/2008 | Sielecki-Dzurdz et al. | |
| 2008/0317759 A1 | 12/2008 | Bucala et al. | |
| 2010/0184046 A1 | 7/2010 | Klass et al. | |
| 2010/0196426 A1 | 8/2010 | Skog et al. | |
| 2011/0118298 A1 | 5/2011 | Fritz et al. | |
| 2011/0160210 A1 | 6/2011 | Fleenor et al. | |
| 2012/0208706 A1 | 8/2012 | Downing et al. | |
| 2013/0005599 A1* | 1/2013 | Klass ................... | C12Q 1/6886 506/9 |
| 2013/0029339 A1 | 1/2013 | Skog et al. | |
| 2013/0177498 A1 | 7/2013 | Goldenberg et al. | |
| 2013/0287801 A1 | 10/2013 | Castronovo et al. | |
| 2014/0038901 A1 | 2/2014 | Lyden et al. | |
| 2014/0045915 A1 | 2/2014 | Skog et al. | |
| 2014/0162888 A1 | 6/2014 | Kuslich et al. | |
| 2014/0178403 A1 | 6/2014 | Bucala et al. | |
| 2014/0227179 A1 | 8/2014 | Liu et al. | |
| 2015/0218651 A1 | 8/2015 | Lyden et al. | |

(Continued)

FOREIGN PATENT DOCUMENTS

| | | | |
|---|---|---|---|
| WO | 2005/091805 A2 | 6/2005 | |
| WO | 2009/100029 | 8/2009 | |

(Continued)

OTHER PUBLICATIONS

Fesler, A., et al. Circulating microRNA testing for the early diagnosis and follow-up of colorectal cancer patients. Mol. Diagn. Ther., Jun. 2014, 18(3):303-308.*
He, X-X., et al. Macrophage migration inhibitor factor promtes colorectal cancer. Molecular Medicine, Jan.-Feb. 2009, 15(1-2):1-10.*
Mathivanan S, et al. Exosomes: Extracellular organelles important in intercellular communication. J. Proteomics, 2010, 73:1907-1920.*
Batagov, A.O., et al. Exosomes secreted by human cells transport largely mRNA fragments that are enriched in the 3'-untranslated regions. Biology Direct, 2013, 8:12, p. 1-8.*
Shabad L.M., Bull. Wld. Hlth Org., 26: 649-659, 1962.*
International Search Report and Written Opinion for corresponding Application No. PCT/US2015/054538 (dated Feb. 25, 2016).

(Continued)

*Primary Examiner* — Gyan Chandra
(74) *Attorney, Agent, or Firm* — Troutman Pepper Hamilton Sanders LLP (Rochester)

(57) ABSTRACT

The present invention is directed to a method for identifying an individual who is at risk for developing metastatic liver disease that involves measuring, in a sample isolated from the individual, exosomal levels of one or more markers of metastatic liver disease. Kits for carrying out this method are also disclosed. The present invention also relates to a method of preventing metastatic liver disease in an individual who are at risk for developing the disease that involves administering one or more inhibitors of liver pre-metastatic niche formation.

7 Claims, 28 Drawing Sheets
Specification includes a Sequence Listing.

(56) References Cited

U.S. PATENT DOCUMENTS

| | | | |
|---|---|---|---|
| 2017/0175200 A1 | 6/2017 | Lyden et al. | |
| 2018/0045728 A1 | 2/2018 | Kalluri et al. | |
| 2018/0231558 A1 | 8/2018 | Lyden et al. | |
| 2019/0049435 A1 | 2/2019 | Lyden et al. | |

FOREIGN PATENT DOCUMENTS

| | | | |
|---|---|---|---|
| WO | 2010/056337 | | 5/2010 |
| WO | 2010/141955 | | 12/2010 |
| WO | 2012/031008 | | 3/2012 |
| WO | WO2012/135844 | * | 10/2012 |
| WO | 2013/028788 | | 2/2013 |
| WO | 2013/134786 | | 9/2013 |
| WO | 2014/028862 | | 2/2014 |
| WO | 2014/037332 | | 3/2014 |
| WO | 2014/055775 | | 4/2014 |
| WO | 2014/062978 A1 | | 4/2014 |

OTHER PUBLICATIONS

Zhang et al., "A Niche Role for Cancer Exosomes in Metastasis," Nat. Cell Biol. 17(6):709-711 (2015).
Seton-Rogers, "Metastasis: An Influential Delivery," Nat. Rev. Cancer 15(7):386 (2015).
Ferrarelli, "Exosomes Prep the Metastatic Site," Sci. Signal. 8(380):ec150 (2015).
He et al., "Macrophage Migration Inhibitory Factor Promotes Colorectal Cancer," Mol. Med. 15(1-2):1-10 (2009).
Lalazar, "MIF: A Harbinger of Evil," Sci. Translational Med. 7(292):292 (2015).
Vignieri and Smith, "Cancer Biology: Tumor Cells Educate the Metastatic Niche," Science Magazine 348 (6240):1220 (Jun. 12, 2015).
Ray, "Pancreatic Cancer Exosomes Prime the Liver for Metastasis," Nat. Rev. Gastroenterol. Hepatol. 12(7):371 (2015).
Costa-Silva et al., "Pancreatic Cancer Exosomes Initiate Pre-Metastatic Niche Formation in the Liver," Nat. Cell Biol. 17:816-826 (2015).
Hagemann et al., "Macrophages Induce Invasiveness of Epithelial Cancer Cells via NF-kappaB and JNK," J. Immunol. 175:1197-1205 (2005).
Funamizu et al., "Macrophage Migration Inhibitory Factor (MIF) Induces Epithelial to Mesenchymal Transition, Enhances Tumor Aggressiveness and Predicts Clinical Outcome in Resected Pancreatic Ductal Adenocarcinoma," Int. J. Cancer 132(4):785-794 (2013).
Chen et al., "ISO-1, a Macrophage Migration Inhibitory Factor Antagonist, Inhibits Airway Remodeling in a Murine Model of Chronic Asthma," Mol. Med. 16(9-10):400-408 (2010).
Garai et al., "Macrophage Migration Inhibitory Factor (MIF) Tautomerase Inhibitors as Potential Novel Anti-Inflammatory Agents: Current Developments," Curr. Med. Chem. 16:1091-1114 (2009).
Xu et al., "Current Developments of Macrophage Migration Inhibitory Factor (MIF) Inhibitors," Drug Discovery Today 18(11-12):592-600 (2013).
Guescini et al., "Astrocytes and Glioblastoma Cells Release Exosomes Carrying mtDNA," J Neural Transm 117 (1):1-4 (2010).
Balaj et al., "Tumour Microvesicles Contain Retrotransposon Elements and Amplified Oncogene Sequences," Nat Commun 2:180 (2011).
Zhang et al., "Stimulated Human Mast Cells Secrete Mitochondrial Components That Have Autocrine and Paracrine Inflammatory Actions," PLOS One 7(12):1-9 (2012).
Kahlert et al., "Identification of Double-Stranded Genomic DNA Spanning Chromosomes with Mutated KRAS and p53 DNA in the Serum Exosomes of Patients with Pancreatic Cancer," J. Biol. Chem. 289(7):3869-3875 (2014).
Thakur et al., "Double-Stranded DNA in Exosomes: a Novel Biomarker in Cancer Detection," Cell Res. 24(6)766-769 (2014).
Zimmer et al., "The S100 Protein Family: History, Function, and Expression," Brain Research Bulletin 37(4):417-429 (1995).
Schmid et al., "EGFR/KRAS/BRAF Mutations in Primary Lung Adenocarcinomas and corresponding Locoregional Lymph Node Metastase," Clin Cancer Res. 15:4554 (2009).
Adamczyk et al., "Characterization of Soluble and Exosomal Forms of the EGFR Released from Pancreatic Cancer Cells," Life Sciences 89:304 (2011).
Desgrosellier et al., "Integrins in Cancer: Biological Implications and Therapeutic Opportunities," Nat Rev Cancer 10(1):9-22 (2010).
Enns et al., "Alphavbeta5-integrins Mediate Early Steps of Metastasis Formation," Eur J Cancer 41 (7):1065-1072 (2005).
Nair et al., "HYD1-induced Increase in Reactive Oxygen Species Leads to Autophagy and Necrotic Cell Death in Multiple Myeloma Cells," Mol Cancer Ther 8(8):2441-2451 (2009).
Mullamitha et al, "Phase I Evaluation of a Fully Human Anti-Alphav Integrin Monoclonal Antibody (CNTO 95) in Patients With Advanced Solid Tumors," Clin. Cancer Res. 13(7):2128-2135 (2007).

* cited by examiner

| Genes induced by mouse PAN02exo when compared to Normal Pancreas exosomes | | | Genes induced by human BxPC-3exo when compared to PBS treatment | | |
|---|---|---|---|---|---|
| Gene | Log Fold Change | FDR | Gene | Log Fold Change | FDR |
| LOC100128054 | 7.524059149 | 7.28E-15 | S100B | 5.782305593 | 7.38E-05 |
| ADH1A | 6.344404229 | 8.21E-08 | TP63 | 5.172610596 | 0.002778148 |
| FMO2 | 6.17300344 | 1.50E-05 | IL8 | 4.699965751 | 1.39E-63 |
| ADH1B | 6.114073128 | 3.27E-112 | GPR22 | 4.661288999 | 0.027470428 |
| GSTA1 | 5.715984908 | 3.00E-05 | S100A8 | 4.4980507 | 0.047379092 |
| MYH11 | 5.600128884 | 1.17E-27 | CXCL3 | 4.396309109 | 3.17E-54 |
| TNNT2 | 5.514023897 | 2.68E-17 | MMP9 | 4.305146616 | 3.79E-36 |
| CTAGE1 | 5.462042066 | 0.000305047 | CCL7 | 3.93843354 | 4.29E-72 |
| ADAMTS8 | 5.459350748 | 0.000223641 | CSF3 | 3.653969601 | 2.21E-05 |
| KCNB1 | 5.458589734 | 0.000254024 | LILRA3 | 3.605061969 | 5.58E-07 |
| RSPO1 | 5.45752464 | 0.000199908 | PI15 | 3.604054327 | 7.36E-05 |
| IL20RA | 5.456956702 | 0.000195035 | CXCL1 | 3.570170841 | 5.12E-22 |
| NPPB | 5.448133138 | 4.26E-93 | CCL20 | 3.45962387 | 1.51E-78 |
| SYTL5 | 5.377678588 | 5.95E-20 | CXCL2 | 3.4311756 | 2.94E-67 |
| SULT2B1 | 5.362351219 | 0.000417028 | TEX12 | 3.413307007 | 0.012408712 |
| ACTC1 | 5.037689516 | 5.23E-58 | CSF2 | 3.372948353 | 4.08E-22 |
| ACAN | 5.0070819 | 1.03E-22 | CD48 | 3.307474035 | 0.016446605 |
| B3GALT2 | 4.814354727 | 9.67E-62 | TREM1 | 3.303382066 | 2.91E-13 |
| GPR21 | 4.736633955 | 2.21E-76 | CXCL5 | 3.209903872 | 8.93E-56 |
| ASPN | 4.699061196 | 1.12E-23 | MEOX1 | 3.080120853 | 5.58E-10 |
| SAA1 | 4.698316261 | 7.64E-16 | IL24 | 3.06778842 | 1.28E-16 |
| MX2 | 4.625187007 | 3.56E-28 | CXCL6 | 2.987867967 | 1.09E-19 |
| MYOZ1 | 4.598142875 | 2.22E-61 | PF4 | 2.984788464 | 0.004751274 |
| SERTAD4-AS1 | 4.503471551 | 3.11E-09 | IGFBP1 | 2.951378579 | 0.000116361 |
| BMP6 | 4.492740125 | 2.97E-62 | CCL8 | 2.949614509 | 7.10E-14 |
| PLN | 4.43894036 | 8.47E-26 | UNC5D | 2.885831401 | 0.022828144 |
| FBXL22 | 4.388205052 | 7.96E-59 | LIPM | 2.83255934 | 0.001899547 |
| PRELP | 4.337494803 | 8.51E-58 | RAB27B | 2.802950441 | 3.42E-18 |
| TSPAN2 | 4.333478213 | 7.91E-33 | GCNT3 | 2.775488909 | 2.44E-19 |
| INMT | 4.298302772 | 1.99E-59 | C3orf80 | 2.742708889 | 2.74E-29 |
| MYO7B | 4.287496742 | 2.01E-26 | C1QTNF9 | 2.726173094 | 0.019402149 |
| NINJ2 | 4.260308174 | 8.99E-05 | BCL2A1 | 2.650756661 | 0.000369146 |
| OXTR | 4.204233161 | 7.50E-39 | SLCO2B1 | 2.563623162 | 2.32E-28 |
| ZNF704 | 4.198649771 | 5.98E-44 | FDCSP | 2.535004007 | 3.51E-06 |
| SEMA5B | 4.152757563 | 2.02E-12 | LINC00520 | 2.533941289 | 1.53E-15 |
| ACTA2 | 4.151564817 | 6.54E-33 | SIGLEC9 | 2.468104621 | 1.48E-05 |
| VIT | 4.113207873 | 1.12E-27 | IGFN1 | 2.415122317 | 3.02E-12 |
| RAMP1 | 4.06988694 | 4.80E-70 | TREML3P | 2.413522986 | 1.26E-13 |
| RPRML | 4.060162629 | 0.000156682 | PDK4 | 2.410051907 | 7.01E-57 |
| LINC00312 | 4.049725602 | 3.29E-60 | IL33 | 2.399485975 | 1.92E-18 |
| MEGF6 | 4.048776556 | 2.02E-73 | ADAMDEC1 | 2.392208335 | 0.024701594 |
| HSD17B6 | 4.028722359 | 8.16E-43 | RERG | 2.37674902 | 3.75E-14 |
| PTPRZ1 | 4.021468674 | 1.31E-22 | G0S2 | 2.344614021 | 2.89E-53 |
| SFRP4 | 4.012510892 | 9.33E-113 | CXCL10 | 2.334753268 | 0.009221518 |
| COMP | 3.978816339 | 4.61E-44 | IL1B | 2.333049732 | 2.72E-23 |
| MX1 | 3.949463561 | 6.68E-23 | LPAR4 | 2.31995155 | 0.011388819 |
| NPNT | 3.938992723 | 1.19E-05 | EGR2 | 2.298494163 | 1.54E-20 |
| LMCD1 | 3.922326565 | 1.47E-76 | LOC100505622 | 2.277347805 | 5.51E-05 |
| GDF6 | 3.85458637 | 5.44E-123 | TNFSF18 | 2.274093776 | 5.09E-14 |
| OLFML2B | 3.795245437 | 9.74E-19 | CCL13 | 2.271133719 | 5.80E-15 |
| LOC643355 | 3.766341005 | 6.26E-08 | FGR | 2.257531363 | 0.015418117 |
| OAS1 | 3.734179 | 5.58E-23 | LOC344887 | 2.256635142 | 5.04E-19 |
| EFHD1 | 3.666151754 | 2.66E-61 | PTGS2 | 2.24078561 | 1.91E-49 |
| IFI44L | 3.609637545 | 5.69E-18 | FAM163A | 2.233387665 | 2.73E-10 |
| CNN1 | 3.604278042 | 1.83E-48 | BEX2 | 2.215293166 | 2.88E-05 |

Figure 19A

| Genes induced by mouse PAN02exo when compared to Normal Pancreas exosomes | | | Genes induced by human BxPC-3exo when compared to PBS treatment | | |
|---|---|---|---|---|---|
| KCNJ6 | 3.587859996 | 3.42E-17 | MIR4635 | 2.209766963 | 0.008810472 |
| FOXS1 | 3.576522492 | 5.65E-45 | RAB39B | 2.183243204 | 6.23E-08 |
| PKP2 | 3.574709277 | 1.42E-108 | AKR1C1 | 2.18238439 | 4.08E-18 |
| EPPK1 | 3.489326926 | 3.36E-24 | LILRB4 | 2.156392088 | 2.33E-06 |
| MFAP4 | 3.459323897 | 3.63E-61 | CLDN1 | 2.15621489 | 4.86E-62 |
| ECEL1 | 3.450434323 | 9.45E-07 | ZMAT4 | 2.10821211 | 0.000172345 |
| CCDC146 | 3.440143709 | 3.79E-24 | ANKRD22 | 2.104808861 | 0.000355804 |
| HOPX | 3.435470236 | 2.46E-20 | STEAP4 | 2.096475472 | 6.93E-10 |
| KRT18 | 3.431053017 | 3.47E-95 | SPTA1 | 2.085870837 | 0.002703656 |
| SERTAD4 | 3.425292695 | 1.25E-15 | GKN2 | 2.042172855 | 0.003319173 |
| GJA5 | 3.41869236 | 1.10E-08 | ALOX5AP | 2.03340418 | 0.000568048 |
| SH3GL3 | 3.417051928 | 0.000182815 | LILRB2 | 2.026344856 | 0.021268213 |
| HFM1 | 3.414757513 | 0.000307095 | LOC643723 | 2.025619372 | 9.33E-11 |
| FGF9 | 3.412154923 | 4.26E-46 | SPOCK3 | 2.013590795 | 3.97E-05 |
| PTGIS | 3.410665791 | 8.40E-46 | GPR115 | 2.005654606 | 8.66E-13 |
| NCALD | 3.409927008 | 2.95E-15 | IGF2-AS | 1.992999273 | 0.002687647 |
| ACTG2 | 3.395665745 | 1.90E-50 | C15orf48 | 1.989412713 | 1.98E-05 |
| RGS7BP | 3.391765237 | 9.22E-20 | SLC22A3 | 1.978686891 | 1.30E-51 |
| PALM3 | 3.351323862 | 0.000238664 | IGF2 | 1.972293632 | 1.52E-10 |
| AMZ1 | 3.335833276 | 6.26E-110 | TNFRSF9 | 1.962116566 | 2.71E-08 |
| KIF26B | 3.334337811 | 4.74E-53 | MIR146A | 1.924124805 | 1.41E-05 |
| C10orf10 | 3.306838664 | 2.42E-94 | LOC729177 | 1.909633145 | 0.021268213 |
| KRT32 | 3.273025522 | 4.79E-11 | MME | 1.907876625 | 3.61E-16 |
| IL1RAPL2 | 3.256005142 | 3.46E-05 | IFI44L | 1.906644191 | 1.92E-07 |
| LOC100505633 | 3.25558642 | 3.23E-69 | NAMPT | 1.890895671 | 5.95E-62 |
| HSPB7 | 3.255245865 | 1.49E-30 | CCL11 | 1.880929922 | 1.17E-16 |
| NOX4 | 3.209934071 | 8.97E-38 | TDO2 | 1.880580169 | 7.61E-41 |
| XPNPEP2 | 3.20782835 | 2.61E-05 | DMRTA1 | 1.879690641 | 0.018222364 |
| ADH1C | 3.206605285 | 3.99E-05 | CDRT1 | 1.875760341 | 0.01391475 |
| COL14A1 | 3.202637433 | 5.82E-29 | DNER | 1.862896595 | 6.34E-32 |
| PLEKHA7 | 3.179068747 | 2.84E-46 | SCG2 | 1.840464617 | 2.31E-41 |
| KCNMB1 | 3.157091229 | 2.03E-05 | STRA6 | 1.840400916 | 1.70E-06 |
| WISP1 | 3.154107436 | 1.07E-37 | PDE4B | 1.828296663 | 4.65E-28 |
| LDB3 | 3.126718552 | 1.45E-24 | IL1A | 1.825155926 | 1.03E-32 |
| CCDC81 | 3.100415857 | 5.69E-18 | MYH15 | 1.810502881 | 2.86E-09 |
| C7orf69 | 3.079024731 | 3.19E-26 | HMOX1 | 1.809512155 | 9.96E-34 |
| SYNPO2L | 3.078289498 | 2.21E-26 | AKR1B10 | 1.800940466 | 9.31E-14 |
| SYNPO | 3.066502549 | 5.00E-61 | SAMSN1 | 1.800323612 | 0.000260774 |
| NXPH3 | 3.058597706 | 1.14E-34 | KCNJ15 | 1.793514558 | 0.012710666 |
| ANKRD1 | 3.046958525 | 3.21E-26 | KCNJ2 | 1.785118191 | 9.28E-05 |
| C9orf106 | 3.039114742 | 0.000385046 | TNFAIP6 | 1.777902616 | 5.19E-46 |
| ELN | 3.032615564 | 2.00E-23 | TFPI2 | 1.770869761 | 9.27E-24 |
| PGM5 | 3.026629556 | 1.24E-53 | HSD11B1 | 1.753988244 | 7.87E-18 |
| HEYL | 3.001999418 | 7.02E-29 | DIO2 | 1.740588354 | 6.21E-16 |
| FAM83D | 3.001102626 | 6.86E-32 | LINC00622 | 1.737962895 | 6.15E-07 |
| KIAA0040 | 2.982988069 | 7.14E-46 | ENPP3 | 1.731803617 | 1.36E-05 |
| H19 | 2.9819341 | 4.73E-08 | PLIN2 | 1.727549147 | 4.26E-77 |
| MEST | 2.97513194 | 5.13E-35 | TDRD6 | 1.719739715 | 2.05E-07 |
| CACNB4 | 2.967632497 | 5.23E-33 | AKR1C2 | 1.719572885 | 3.23E-25 |
| NHSL2 | 2.956610016 | 1.36E-21 | CFHR1 | 1.709938662 | 0.003123255 |
| CCDC80 | 2.944961169 | 2.36E-73 | AGTR1 | 1.685012131 | 6.78E-18 |
| NXPE2 | 2.942001334 | 3.87E-26 | TNIP3 | 1.674538426 | 2.85E-09 |
| HMCN1 | 2.91552812 | 3.19E-72 | SLITRK6 | 1.67399002 | 0.020741378 |
| GPRIN3 | 2.900269582 | 5.91E-07 | DPT | 1.67288709 | 0.007859062 |
| B3GAT1 | 2.883005414 | 1.14E-40 | LAMP3 | 1.671564503 | 2.33E-08 |
| ITIH3 | 2.855294711 | 1.49E-20 | BCAN | 1.671563079 | 0.006256414 |
| MGP | 2.854393369 | 4.35E-37 | ABI3BP | 1.671391816 | 3.03E-70 |

Figure 19B

| Genes induced by mouse PAN02exo when compared to Normal Pancreas exosomes | | | Genes induced by human BxPC-3exo when compared to PBS treatment | | |
|---|---|---|---|---|---|
| USP18 | 2.849902598 | 3.47E-21 | NPY1R | 1.654482657 | 9.89E-19 |
| OAS2 | 2.830516204 | 3.64E-29 | SCRG1 | 1.642213968 | 1.10E-11 |
| RTKN2 | 2.828337274 | 2.07E-27 | TRIL | 1.635030594 | 1.44E-08 |
| A2M | 2.819816569 | 4.99E-22 | KYNU | 1.632196729 | 0.000420749 |
| KIAA0226L | 2.818721528 | 8.31E-07 | FCGR2B | 1.621497691 | 0.006359361 |
| IFIT1 | 2.813306143 | 1.16E-29 | PAPPA | 1.600345514 | 7.77E-47 |
| SLC13A5 | 2.810640351 | 7.09E-07 | RGS18 | 1.585075624 | 0.021584242 |
| MMP11 | 2.808038782 | 8.77E-81 | NPY5R | 1.584430301 | 0.021110596 |
| FMO3 | 2.784385382 | 2.71E-05 | C12orf39 | 1.581173603 | 0.003786866 |
| TMEM119 | 2.768253745 | 8.64E-92 | LIN7A | 1.565944226 | 2.04E-08 |
| KRT7 | 2.768124122 | 2.84E-31 | HSD3BP4 | 1.562412946 | 4.96E-07 |
| WFDC1 | 2.763713445 | 5.16E-19 | FAIM2 | 1.554143467 | 4.89E-09 |
| OVCH2 | 2.757757253 | 2.43E-07 | MMP12 | 1.554078904 | 3.65E-10 |
| RASGRP1 | 2.749719278 | 2.90E-29 | LOC148696 | 1.543395422 | 0.022032804 |
| IFI27 | 2.744862005 | 4.27E-14 | BHLHE40-AS1 | 1.537685217 | 0.030277997 |
| NKAIN4 | 2.73631803 | 1.45E-05 | PTPN22 | 1.536246758 | 1.52E-05 |
| HAPLN3 | 2.736122297 | 4.28E-73 | TRABD2A | 1.526917779 | 0.044597261 |
| KRT33B | 2.730547658 | 0.000205947 | KCNN1 | 1.523717562 | 0.03962665 |
| SLA | 2.717691731 | 5.38E-09 | PDC | 1.518920878 | 1.36E-05 |
| IFI6 | 2.711465419 | 2.90E-16 | LCN1 | 1.518492668 | 0.011693391 |
| LBH | 2.70858854 | 2.45E-39 | AADAC | 1.515657945 | 2.04E-10 |
| OAS3 | 2.699400764 | 5.29E-22 | CCDC102B | 1.513317837 | 6.06E-16 |
| GPBAR1 | 2.692402213 | 1.64E-24 | LINC00536 | 1.510020052 | 1.16E-08 |
| SYBU | 2.689275398 | 3.89E-56 | LINC00595 | 1.507811062 | 0.000736899 |
| TMEM130 | 2.685488473 | 3.08E-59 | PAPPA2 | 1.506582065 | 1.87E-37 |
| NREP | 2.67622946 | 2.40E-65 | IL4I1 | 1.503568957 | 0.000141468 |
| TAGLN | 2.673055081 | 2.27E-61 | FAIM3 | 1.503328476 | 6.78E-09 |
| SHISA3 | 2.672622452 | 3.21E-14 | | | |
| SORBS1 | 2.668907897 | 2.04E-33 | | | |
| MEOX1 | 2.667371177 | 9.73E-20 | | | |
| FAM46B | 2.661221214 | 6.50E-14 | | | |
| C12orf69 | 2.660331154 | 3.21E-20 | | | |
| ACTBL2 | 2.629241299 | 1.76E-12 | | | |
| FAM150A | 2.627871378 | 1.95E-38 | | | |
| ITGA9 | 2.625667597 | 6.39E-17 | | | |
| CPA4 | 2.622352606 | 2.03E-71 | | | |
| CYP7B1 | 2.612475099 | 7.84E-11 | | | |
| NTF4 | 2.600354556 | 2.27E-06 | | | |
| LMOD1 | 2.588635394 | 1.24E-27 | | | |
| SLC38A4 | 2.587875338 | 2.29E-25 | | | |
| C1orf198 | 2.585829464 | 2.53E-36 | | | |
| GABRA5 | 2.57883383 | 1.82E-05 | | | |
| MGAM | 2.561092393 | 3.72E-24 | | | |
| IL16 | 2.561023454 | 7.88E-28 | | | |
| FBLN2 | 2.558300966 | 2.58E-70 | | | |
| LOC100505718 | 2.558243337 | 2.98E-20 | | | |
| KRT19 | 2.557763078 | 1.31E-46 | | | |
| C11orf87 | 2.553011307 | 8.57E-26 | | | |
| SIK1 | 2.549041456 | 4.38E-83 | | | |
| DPT | 2.544430406 | 6.35E-29 | | | |
| CHN2 | 2.539314664 | 1.19E-24 | | | |
| SERPINA3 | 2.536020663 | 9.80E-22 | | | |
| JPH2 | 2.533838323 | 2.86E-27 | | | |
| SGCD | 2.529007021 | 4.61E-29 | | | |
| BPI | 2.522106716 | 1.25E-09 | | | |
| CDX1 | 2.510123419 | 5.74E-09 | | | |
| SCN3A | 2.502547162 | 3.51E-28 | | | |

Figure 19C

| Genes induced by mouse PAN02exo when compared to Normal Pancreas exosomes | | | Genes induced by human BxPC-3exo when compared to PBS treatment |
|---|---|---|---|
| MFAP5 | 2.497989353 | 1.02E-59 | |
| ZCCHC5 | 2.49624461 | 7.98E-19 | |
| IFITM1 | 2.491236578 | 4.27E-25 | |
| COL1A1 | 2.490396084 | 2.06E-60 | |
| SULF1 | 2.483323091 | 7.80E-52 | |
| LIMS2 | 2.48011122 | 2.82E-51 | |
| ITGBL1 | 2.479500715 | 8.02E-60 | |
| TPD52L1 | 2.476493555 | 4.17E-16 | |
| SCGB3A2 | 2.467249582 | 7.84E-12 | |
| COL4A1 | 2.465165718 | 5.65E-48 | |
| GFRA1 | 2.462745548 | 7.18E-23 | |
| ASB5 | 2.462214833 | 3.81E-06 | |
| CELSR1 | 2.45558854 | 1.47E-90 | |
| ALDH1B1 | 2.453290015 | 2.57E-30 | |
| ROR1 | 2.449236378 | 9.20E-34 | |
| ISG15 | 2.447911727 | 1.53E-27 | |
| ANO1 | 2.445130907 | 2.66E-45 | |
| IL22RA1 | 2.443364214 | 2.31E-05 | |
| ST6GALNAC5 | 2.442786208 | 4.09E-15 | |
| ART4 | 2.440980667 | 4.97E-24 | |
| SYNM | 2.439753205 | 1.41E-39 | |
| TRIL | 2.431061427 | 1.70E-15 | |
| CMPK2 | 2.429094653 | 1.62E-09 | |
| KCNH1 | 2.423086526 | 3.77E-06 | |
| ITGB1BP2 | 2.422565648 | 7.24E-23 | |
| ECM2 | 2.42251806 | 2.07E-33 | |
| GPR17 | 2.410509369 | 1.14E-18 | |
| KCND3 | 2.405924176 | 9.09E-27 | |
| HERC6 | 2.389468358 | 1.62E-26 | |
| KAL1 | 2.38893552 | 6.78E-09 | |
| SLIT3 | 2.388385894 | 5.66E-69 | |
| MN1 | 2.386351935 | 4.40E-72 | |
| ITGA8 | 2.385841782 | 1.99E-40 | |
| COL11A1 | 2.380717645 | 7.38E-12 | |
| TRPM2 | 2.37293964 | 0.000108827 | |
| NIPAL4 | 2.369458711 | 9.80E-09 | |
| COL15A1 | 2.366663763 | 2.84E-23 | |
| IGF1 | 2.363041473 | 3.95E-11 | |
| ROR2 | 2.358723144 | 4.05E-61 | |
| GLB1L2 | 2.354486223 | 1.81E-06 | |
| FAM35DP | 2.35144086 | 0.000616164 | |
| NPAS4 | 2.347417684 | 6.84E-06 | |
| UPK1A-AS1 | 2.346897562 | 1.09E-07 | |
| FAXC | 2.34186364 | 6.43E-29 | |
| PODNL1 | 2.341057058 | 2.52E-82 | |
| PCDHA12 | 2.340843313 | 4.95E-08 | |
| PPP1R12B | 2.336905179 | 2.85E-48 | |
| CDH1 | 2.332319439 | 2.20E-07 | |
| HR | 2.327978431 | 7.90E-25 | |
| PODN | 2.325698165 | 1.70E-34 | |
| PPP1R14A | 2.324912609 | 1.88E-55 | |
| HNRNPA1P33 | 2.323644546 | 1.63E-08 | |
| P2RY6 | 2.322061067 | 5.58E-09 | |
| SUSD2 | 2.318456375 | 4.10E-48 | |
| ATP10A | 2.316927897 | 3.07E-51 | |
| EXTL1 | 2.315371235 | 1.04E-33 | |
| LFNG | 2.314732839 | 2.46E-24 | |

Figure 19D

| Genes induced by mouse PAN02exo when compared to Normal Pancreas exosomes | | | Genes induced by human BxPC-3exo when compared to PBS treatment |
|---|---|---|---|
| FRY | 2.304046336 | 3.88E-33 | |
| ISLR | 2.303950851 | 3.79E-26 | |
| FAM163B | 2.303021928 | 8.71E-07 | |
| PSORS1C1 | 2.303016815 | 3.34E-05 | |
| SHROOM2 | 2.29770631 | 8.07E-24 | |
| ADRA2A | 2.293010193 | 0.000465993 | |
| PDLIM3 | 2.289785952 | 1.52E-47 | |
| GRIP2 | 2.289261687 | 1.19E-06 | |
| FN1 | 2.28573274 | 2.69E-95 | |
| ARHGEF4 | 2.284917447 | 7.24E-30 | |
| KCNE1 | 2.283627927 | 1.13E-06 | |
| KLHL10 | 2.272184577 | 8.51E-05 | |
| ATP1A3 | 2.266494338 | 1.28E-09 | |
| CHRM5 | 2.252327338 | 6.43E-06 | |
| RIMS1 | 2.246543691 | 6.24E-08 | |
| PIK3AP1 | 2.244143171 | 2.00E-09 | |
| TNXB | 2.236909308 | 1.91E-32 | |
| PRR15 | 2.232131856 | 2.97E-38 | |
| SOD3 | 2.224312445 | 3.05E-45 | |
| FGF1 | 2.223195346 | 1.06E-23 | |
| LRRC32 | 2.214475585 | 7.98E-73 | |
| BMP4 | 2.213789836 | 1.88E-22 | |
| KRT80 | 2.211552527 | 7.66E-20 | |
| NTN4 | 2.210311882 | 2.61E-52 | |
| LINC00607 | 2.207942504 | 1.91E-27 | |
| LDLRAD4 | 2.203109485 | 1.90E-30 | |
| POSTN | 2.202239231 | 4.85E-71 | |
| STARD4-AS1 | 2.201868867 | 2.43E-31 | |
| WIPF3 | 2.197944418 | 0.0001101 | |
| ANK3 | 2.193894129 | 1.71E-86 | |
| PTPLAD2 | 2.193395495 | 8.09E-44 | |
| SLC16A9 | 2.190039937 | 1.58E-05 | |
| FBLN1 | 2.189426379 | 4.09E-15 | |
| DIAPH3 | 2.187240625 | 1.67E-38 | |
| PLCL1 | 2.178947736 | 8.58E-48 | |
| MAN1C1 | 2.176329772 | 2.84E-31 | |
| MYH15 | 2.172551957 | 2.90E-20 | |
| LHX9 | 2.168116086 | 2.85E-07 | |
| ACVR2A | 2.166274202 | 1.82E-77 | |
| TC2N | 2.164967038 | 9.34E-06 | |
| MATN3 | 2.149111459 | 4.36E-55 | |
| DEPTOR | 2.147122479 | 1.36E-58 | |
| C5orf46 | 2.138399314 | 2.41E-14 | |
| NPR1 | 2.135160136 | 0.000814051 | |
| COL5A1 | 2.134822335 | 6.67E-62 | |
| KRT34 | 2.130846125 | 1.57E-17 | |
| COL5A3 | 2.130012067 | 3.87E-62 | |
| SYNPO2 | 2.125507771 | 2.30E-28 | |
| THBS1 | 2.125295084 | 2.88E-40 | |
| THRB | 2.124864513 | 1.36E-08 | |
| SCRG1 | 2.123107975 | 6.21E-10 | |
| RAB33A | 2.118190885 | 8.49E-23 | |
| FIBIN | 2.11306888 | 6.33E-28 | |
| FMOD | 2.11304386 | 1.28E-26 | |
| KCNK3 | 2.112486666 | 1.35E-10 | |
| SNED1 | 2.108030194 | 3.57E-55 | |
| FGF14 | 2.105603473 | 1.15E-11 | |

Figure 19E

| Genes induced by mouse PAN02exo when compared to Normal Pancreas exosomes | | | Genes induced by human BxPC-3exo when compared to PBS treatment |
|---|---|---|---|
| OLFML3 | 2.105463988 | 1.43E-57 | |
| GLP2R | 2.10390926 | 1.55E-07 | |
| PTH1R | 2.10381271 | 5.68E-07 | |
| SLC2A5 | 2.096846413 | 5.50E-11 | |
| ARNT2 | 2.096007845 | 1.55E-62 | |
| FNDC1 | 2.092269161 | 8.92E-23 | |
| FAM90A1 | 2.082670744 | 0.000106997 | |
| TMEM37 | 2.082183848 | 0.000221988 | |
| KIT | 2.080533098 | 2.84E-32 | |
| ALPK2 | 2.080529145 | 3.34E-40 | |
| TINAGL1 | 2.080231668 | 2.58E-70 | |
| LINC00319 | 2.074851288 | 3.42E-12 | |
| PRSS35 | 2.073653163 | 3.72E-24 | |
| FNDC5 | 2.072053578 | 1.85E-06 | |
| MGC16121 | 2.072028624 | 6.89E-20 | |
| SLC8A1 | 2.070797246 | 9.29E-27 | |
| ANXA3 | 2.06934259 | 3.35E-21 | |
| EPSTI1 | 2.069094252 | 8.07E-19 | |
| SULF2 | 2.067837442 | 2.36E-52 | |
| FIBCD1 | 2.048468221 | 3.12E-31 | |
| SESN3 | 2.041280421 | 2.70E-89 | |
| MUC1 | 2.029840909 | 5.70E-39 | |
| TNFSF4 | 2.028304785 | 2.18E-50 | |
| MRVI1 | 2.010259653 | 8.64E-21 | |
| EBI3 | 2.005873622 | 0.000286013 | |
| CFB | 2.004775453 | 1.11E-42 | |
| LOC100506795 | 1.999829974 | 4.95E-09 | |
| KCNS3 | 1.99906361 | 2.29E-31 | |
| GALNT16 | 1.995311245 | 5.47E-20 | |
| PLXDC1 | 1.988956339 | 9.46E-36 | |
| RIMS3 | 1.988378753 | 3.51E-16 | |
| RARRES2 | 1.984754413 | 4.99E-14 | |
| MIR143HG | 1.982797955 | 1.89E-15 | |
| HSPA2 | 1.981932628 | 2.22E-19 | |
| NCAM2 | 1.973776359 | 4.86E-18 | |
| STAC | 1.972813678 | 8.77E-39 | |
| HTR2A | 1.970152949 | 1.19E-15 | |
| C7 | 1.967517977 | 1.38E-09 | |
| FXYD1 | 1.966431531 | 1.98E-10 | |
| C21orf7 | 1.96400731 | 1.95E-48 | |
| IGFBPL1 | 1.95915086 | 1.71E-10 | |
| C10orf107 | 1.958350679 | 2.64E-20 | |
| GPC3 | 1.955300124 | 2.99E-11 | |
| ADRA2C | 1.951595621 | 0.000830346 | |
| ZNF365 | 1.951254273 | 1.32E-32 | |
| CLSTN2 | 1.94922819 | 2.80E-27 | |
| COL3A1 | 1.946305479 | 4.06E-29 | |
| ARHGAP20 | 1.943432992 | 7.34E-52 | |
| STARD5 | 1.943142462 | 1.83E-44 | |
| GPR124 | 1.942242452 | 1.60E-78 | |
| GAS1 | 1.940515115 | 8.35E-11 | |
| LRRN2 | 1.939411394 | 3.01E-05 | |
| SYT12 | 1.939339458 | 1.89E-22 | |
| CTGF | 1.934174895 | 5.16E-20 | |
| XAF1 | 1.930663011 | 1.45E-52 | |
| JAK3 | 1.927175098 | 2.45E-28 | |
| ABCA9 | 1.926675718 | 1.14E-23 | |

Figure 19F

| Genes induced by mouse PAN02exo when compared to Normal Pancreas exosomes | | | Genes induced by human BxPC-3exo when compared to PBS treatment |
|---|---|---|---|
| LIMCH1 | 1.924354741 | 9.46E-23 | |
| AKAP5 | 1.924185968 | 5.84E-44 | |
| CYS1 | 1.924058165 | 3.29E-47 | |
| HRH2 | 1.921323407 | 0.000526243 | |
| PARP9 | 1.920200391 | 9.26E-48 | |
| VTN | 1.918369557 | 1.82E-20 | |
| CXCR7 | 1.915505063 | 5.25E-23 | |
| MYLK | 1.915217464 | 2.58E-23 | |
| THBS2 | 1.910417009 | 4.21E-59 | |
| ELOVL2 | 1.909135936 | 6.31E-30 | |
| LYPD6 | 1.908348795 | 0.000369277 | |
| SYNE2 | 1.907745236 | 3.22E-46 | |
| SLC1A7 | 1.905916023 | 1.15E-18 | |
| HAPLN1 | 1.900461905 | 2.45E-07 | |
| SH3RF2 | 1.898120445 | 6.40E-84 | |
| FAM65B | 1.887536124 | 6.10E-15 | |
| CCL11 | 1.876334328 | 1.01E-06 | |
| C2 | 1.873537404 | 4.75E-34 | |
| LGSN | 1.872949214 | 1.03E-09 | |
| PPYR1 | 1.871948716 | 1.47E-06 | |
| PRICKLE1 | 1.869084321 | 5.70E-23 | |
| POTEF | 1.868812617 | 0.000203419 | |
| SPARC | 1.868357894 | 1.96E-48 | |
| NTRK2 | 1.868163542 | 5.98E-11 | |
| ANKRD6 | 1.855133911 | 2.59E-63 | |
| GPC4 | 1.849005844 | 5.00E-31 | |
| COL4A2 | 1.848334823 | 3.49E-51 | |
| SHROOM3 | 1.847087047 | 9.52E-22 | |
| ANKH | 1.845268247 | 5.19E-75 | |
| AEBP1 | 1.843426085 | 8.41E-62 | |
| OSBPL10 | 1.843075854 | 9.11E-37 | |
| TRIM14 | 1.842145987 | 9.52E-35 | |
| DERL3 | 1.838830558 | 7.15E-08 | |
| DSP | 1.837187988 | 2.71E-59 | |
| SLC9A7P1 | 1.836690104 | 1.06E-16 | |
| ADRA1B | 1.832861674 | 5.36E-17 | |
| COL25A1 | 1.831955502 | 1.40E-18 | |
| MEX3B | 1.831380453 | 1.77E-39 | |
| BST1 | 1.827467125 | 2.25E-64 | |
| CASQ2 | 1.826135708 | 0.000127143 | |
| SYTL2 | 1.825226954 | 3.20E-22 | |
| MYL9 | 1.823112118 | 4.34E-56 | |
| FSCN2 | 1.817747083 | 1.43E-12 | |
| COL1A2 | 1.817665255 | 1.70E-43 | |
| BGN | 1.813790084 | 2.34E-69 | |
| CALD1 | 1.813372497 | 2.06E-37 | |
| PLAC9 | 1.80789524 | 1.23E-38 | |
| NNMT | 1.806322175 | 5.66E-61 | |
| ITGA11 | 1.797108136 | 1.26E-64 | |
| GCK | 1.790677866 | 0.000231281 | |
| KCNG2 | 1.790580801 | 4.07E-05 | |
| KRT86 | 1.789798574 | 7.36E-06 | |
| POTEM | 1.78814089 | 8.37E-06 | |
| KCNE3 | 1.787353122 | 8.91E-15 | |
| GAS7 | 1.780644932 | 7.04E-22 | |
| LEP | 1.779559319 | 0.000180081 | |
| CDKN2B | 1.779285697 | 1.56E-26 | |

Figure 19G

| Genes induced by mouse PAN02exo when compared to Normal Pancreas exosomes | | | Genes induced by human BxPC-3exo when compared to PBS treatment |
|---|---|---|---|
| IGFBP3 | 1.778000238 | 2.00E-27 | |
| KCNT2 | 1.777475969 | 1.70E-10 | |
| DYSF | 1.774657195 | 3.23E-59 | |
| FAT4 | 1.773930959 | 8.92E-34 | |
| RASGRP2 | 1.770783348 | 9.99E-18 | |
| FHL1 | 1.767516026 | 1.36E-31 | |
| KIAA1324L | 1.763677418 | 5.17E-33 | |
| RCAN2 | 1.763500975 | 6.19E-24 | |
| LMO7 | 1.763474293 | 1.16E-27 | |
| FERMT1 | 1.763027257 | 2.44E-34 | |
| CCDC3 | 1.755335484 | 1.01E-21 | |
| B3GNT8 | 1.755083249 | 6.18E-11 | |
| LGALS2 | 1.739574191 | 1.18E-05 | |
| FMO5 | 1.737982228 | 1.28E-15 | |
| MBNL1-AS1 | 1.733072818 | 2.05E-25 | |
| RUNX1T1 | 1.732035124 | 6.49E-37 | |
| PADI1 | 1.731492091 | 2.40E-06 | |
| ID4 | 1.730184092 | 2.27E-14 | |
| GBP1P1 | 1.723902141 | 1.40E-06 | |
| PDE1C | 1.723389156 | 2.88E-24 | |
| CDSN | 1.717035713 | 2.44E-20 | |
| KLHL30 | 1.716907767 | 2.83E-16 | |
| LTBP2 | 1.716726663 | 1.85E-60 | |
| SORBS2 | 1.715413529 | 1.93E-13 | |
| SCN2A | 1.714158178 | 2.35E-21 | |
| PDIA2 | 1.706000219 | 0.000137 | |
| MYOZ2 | 1.705748395 | 2.19E-11 | |
| PRSS23 | 1.705108895 | 5.64E-49 | |
| LRP5 | 1.699262197 | 5.61E-73 | |
| HTR1B | 1.694565871 | 4.80E-15 | |
| SGCG | 1.693736077 | 2.03E-15 | |
| KRTAP1-5 | 1.693581431 | 3.40E-09 | |
| PCK2 | 1.693491479 | 6.37E-36 | |
| LOC255167 | 1.688486888 | 3.12E-05 | |
| PMP22 | 1.68818248 | 3.84E-98 | |
| ADAMTS2 | 1.685577499 | 2.41E-46 | |
| FAM84B | 1.685035548 | 5.77E-26 | |
| FBLN5 | 1.684055151 | 5.52E-31 | |
| CGNL1 | 1.682331599 | 1.07E-25 | |
| AXIN2 | 1.677784162 | 2.54E-45 | |
| GDPD5 | 1.67676922 | 3.17E-59 | |
| CTHRC1 | 1.673297107 | 5.01E-56 | |
| IRF7 | 1.672188721 | 6.74E-18 | |
| ARL4A | 1.670112354 | 3.30E-62 | |
| TMPO-AS1 | 1.670003618 | 5.41E-05 | |
| ACSS1 | 1.662667888 | 1.11E-15 | |
| C10orf54 | 1.661674265 | 5.86E-26 | |
| ALDH1A1 | 1.661653693 | 1.54E-14 | |
| IFIT3 | 1.661064881 | 9.76E-18 | |
| DCN | 1.660756427 | 4.75E-46 | |
| OLFM2 | 1.656922837 | 2.10E-23 | |
| NRXN3 | 1.656310151 | 1.68E-26 | |
| ADAM19 | 1.651693229 | 3.51E-54 | |
| TMEM178B | 1.649308212 | 1.39E-26 | |
| PDGFRB | 1.649250293 | 1.15E-45 | |
| CD34 | 1.649003728 | 3.27E-06 | |
| DTX3L | 1.64771995 | 2.97E-48 | |

Figure 19H

Genes induced by mouse PAN02exo when compared to Normal Pancreas exosomes

Genes induced by human BxPC-3exo when compared to PBS treatment

| Gene | Value | p-value |
|---|---|---|
| SVEP1 | 1.642435239 | 3.17E-28 |
| DDAH1 | 1.64158379 | 1.05E-23 |
| SLC6A17 | 1.638856262 | 5.04E-14 |
| GBP1 | 1.638451734 | 1.95E-23 |
| DOCK11 | 1.630670751 | 1.06E-56 |
| TP53I11 | 1.627355787 | 7.25E-48 |
| ADAMTS12 | 1.6250833 | 5.06E-35 |
| ADAM12 | 1.619532301 | 1.68E-86 |
| GCNT4 | 1.615701157 | 8.30E-10 |
| LPPR3 | 1.614483975 | 8.52E-08 |
| MFAP2 | 1.61345614 | 3.09E-32 |
| ASB2 | 1.612407452 | 6.02E-26 |
| TMEM92 | 1.611556992 | 0.000270101 |
| GARNL3 | 1.611321059 | 8.57E-09 |
| MYH10 | 1.607225074 | 5.27E-24 |
| SLC6A9 | 1.60676313 | 8.17E-26 |
| HSPB1 | 1.60416002 | 2.02E-81 |
| DDX58 | 1.601415309 | 2.41E-20 |
| NXN | 1.598300623 | 3.92E-42 |
| IFIT2 | 1.597275838 | 4.14E-13 |
| ADAMTS15 | 1.596904524 | 2.33E-28 |
| RGS7 | 1.596216449 | 4.84E-15 |
| LTC4S | 1.593302084 | 0.00026869 |
| TUFT1 | 1.59276749 | 2.89E-19 |
| NOSTRIN | 1.592419533 | 1.54E-10 |
| CAPG | 1.58812892 | 5.61E-11 |
| SERPINF1 | 1.587911936 | 1.60E-29 |
| TMC3 | 1.586936352 | 0.000198428 |
| ARHGAP9 | 1.586531369 | 0.000187947 |
| PPAP2A | 1.585952991 | 1.24E-43 |
| CRISPLD2 | 1.58448247 | 1.59E-35 |
| JDP2 | 1.583332914 | 7.60E-53 |
| PLEKHA6 | 1.583047866 | 4.76E-17 |
| PABPC4L | 1.582327067 | 9.13E-12 |
| SGK223 | 1.581958288 | 2.41E-47 |
| LINC00842 | 1.578631237 | 2.11E-14 |
| EFEMP1 | 1.576873663 | 7.38E-36 |
| NMNAT3 | 1.574945619 | 0.000194546 |
| NEDD9 | 1.573419779 | 6.74E-34 |
| SYNC | 1.57220655 | 2.40E-52 |
| CFI | 1.57204251 | 1.77E-48 |
| PPL | 1.571799276 | 2.80E-12 |
| IFITM3 | 1.57163477 | 2.27E-38 |
| ANK2 | 1.56964236 | 5.22E-28 |
| NUAK1 | 1.569362314 | 1.56E-25 |
| IFIH1 | 1.568930808 | 1.16E-22 |
| LOC400456 | 1.563718676 | 7.02E-18 |
| KALRN | 1.561815621 | 5.05E-17 |
| SERPINE2 | 1.561025156 | 2.51E-13 |
| HNMT | 1.55956329 | 4.91E-44 |
| KCND2 | 1.556743383 | 3.82E-25 |
| TLR3 | 1.555300772 | 5.99E-22 |
| GLIPR2 | 1.555112168 | 1.00E-88 |
| FAM13C | 1.554878245 | 1.94E-34 |
| LMO3 | 1.554776197 | 8.30E-06 |
| THY1 | 1.551997405 | 2.33E-51 |
| DAAM2 | 1.549084272 | 2.31E-36 |

Figure 19I

| Genes induced by mouse PAN02exo when compared to Normal Pancreas exosomes | | | Genes induced by human BxPC-3exo when compared to PBS treatment |
|---|---|---|---|
| RHOJ | 1.548349412 | 1.05E-46 | |
| CSRP2 | 1.547035932 | 6.50E-26 | |
| DUSP2 | 1.544866334 | 3.49E-07 | |
| LINC00035 | 1.543255171 | 1.53E-06 | |
| MATN2 | 1.538653348 | 2.75E-20 | |
| MAP2 | 1.537360346 | 1.56E-25 | |
| RASSF2 | 1.53425016 | 2.22E-18 | |
| TNS1 | 1.529983303 | 2.23E-44 | |
| PKDCC | 1.526693835 | 5.70E-49 | |
| PTGDS | 1.526195796 | 0.000475108 | |
| CHRDL2 | 1.524883354 | 1.01E-11 | |
| TGM1 | 1.524736237 | 5.96E-14 | |
| PDE5A | 1.523737554 | 1.19E-38 | |
| PRKAG2 | 1.520516923 | 6.56E-35 | |
| CMAHP | 1.520060628 | 2.93E-13 | |
| FZD7 | 1.517209233 | 3.85E-52 | |
| BAMBI | 1.516646613 | 4.15E-58 | |
| PDZD4 | 1.514562855 | 3.23E-11 | |
| RAB11FIP1 | 1.514437648 | 4.54E-32 | |
| MIAT | 1.512631313 | 9.34E-10 | |
| SCUBE3 | 1.512590565 | 7.84E-28 | |
| GDF5 | 1.511970793 | 2.96E-29 | |
| KIAA1161 | 1.511857708 | 9.71E-19 | |
| RTP4 | 1.511290102 | 1.37E-12 | |
| LOC100130992 | 1.510237952 | 2.87E-10 | |
| SLC4A3 | 1.508150127 | 1.01E-38 | |
| EDIL3 | 1.507933383 | 1.32E-39 | |
| C10orf114 | 1.505459519 | 1.10E-06 | |
| NPAS1 | 1.503874799 | 5.31E-25 | |

Figure 19J

METHODS FOR PROGNOSING AND PREVENTING METASTATIC LIVER DISEASE

This application is a national stage application under 35 U.S.C. § 371 of International Application No. PCT/US2015/054538, filed Oct. 7, 2015, which claims the benefit of U.S. Provisional Patent Application Ser. No. 62/060,925, filed Oct. 7, 2014, which is hereby incorporated by reference in its entirety.

FIELD OF THE INVENTION

The present invention is directed to methods and kits suitable for identifying individuals who are at risk for developing metastatic liver disease, and to methods of preventing metastatic liver disease in those identified individuals.

BACKGROUND OF THE INVENTION

One of the most lethal cancers, pancreatic cancer has a 5-year survival rate of about 6% and a median survival rate of about 6 months (Saif, M. W., "Pancreatic Neoplasm in 2011: An Update," *JOP: Journal of the Pancreas* 12:316-321 (2011); Chan et al., "Strategies for Discovering Novel Pancreatic Cancer Biomarkers," *J. Proteomics* 81:126-134 (2013)), with pancreatic ductal adenocarcinoma (known as PDAC) being the most common type that accounts for more than 90% of cases (Fesinmeyer et al., "Differences in Survival by Histologic Type of Pancreatic Cancer," *Cancer Epidemiol. Biomarkers Prev.* 14:1766-1773 (2005)). The poor prognosis of PDAC is due to a combination of factors, including difficulties in detecting early stage disease, its high metastatic potential, and resistance to conventional therapies. Therefore, a better understanding of the initial events in PDAC development is needed in order to improve early detection and disease intervention.

Exosomes, membrane vesicles of endocytic origin ranging in size from 30 to 150 nm (Arscott & Camphausen, "EGFR Isoforms in Exosomes as a Novel Method for Biomarker Discovery in Pancreatic Cancer," *Biomark. Med.* 5:821 (2011); Record et al., "Exosomes as New Vesicular Lipid Transporters Involved in Cell-Cell Communication and Various Pathophysiologies," *Biochim. Biophys. Acta* 1841:108-120 (2014); El Andaloussi et al., "Extracellular Vesicles: Biology and Emerging Therapeutic Opportunities," *Nat. Rev. Drug Discov.* 12:347-357 (2013)), are emerging as key players in intercellular communication between cancer cells and their microenvironment through horizontal transfer of information via their cargo, which includes proteins, DNAs, mRNAs and microRNAs (Choi et al., "Proteomics, Transcriptomics and Lipidomics of Exosomes and Ectosomes," *Proteomics* 13:1554-1571 (2013); Martins et al., "Tumor-Cell-Derived Microvesicles as Carriers of Molecular Information in Cancer," *Curr. Opin. Oncol.* 25:66-75 (2013); Peinado et al., "The Secreted Factors Responsible for Pre-Metastatic Niche Formation: Old Sayings and New Thoughts," *Semin. Cancer Biol.* 21:139-146 (2011); Thakur et al. "Double-Stranded DNA in Exosomes: A Novel Biomarker in Cancer Detection," *Cell Res.* 24(6):766-9 (2014); Tetta et al., "Extracellular Vesicles as an Emerging Mechanism of Cell-to-Cell Communication," *Endocrine* 44:11-19 (2013); Valadi et al. "Exosome-Mediated Transfer of mRNAs and MicroRNAs is a Novel Mechanism of Genetic Exchange Between Cells," *Nat. Cell Biol.* 9:654-659 (2007); Zoller, M., "Pancreatic Cancer Diagnosis by Free and Exosomal miRNA," *World J. Gastrointest. Pathophysiol.* 4:74-90 (2013)). Recently, the formation of pre-metastatic niches, a sequence of events which prepares future metastatic sites for the influx of tumor cells and which supports engraftment and survival of these incoming metastatic cells (Peinado et al., "The Secreted Factors Responsible for Pre-Metastatic Niche Formation: Old Sayings and New Thoughts," *Semin. Cancer Biol.* 21:139-146 (2011); Kaplan et al., "VEGFR1-Positive Haematopoietic Bone Marrow Progenitors Initiate the Pre-Metastatic Niche," *Nature* 438:820-827 (2005); Sceneay et al., "The Pre-Metastatic Niche: Finding Common Ground," *Cancer Metastasis Rev.* 32:449-464 (2013)), has been shown to depend on tumor-derived exosomes (Peinado et al. "Melanoma Exosomes Educate Bone Marrow Progenitor Cells Toward a Pro-Metastatic Phenotype Through MET," *Nature Med.* 18:883-891 (2012; Hood et al., "Exosomes Released by Melanoma Cells Prepare Sentinel Lymph Nodes for Tumor Metastasis," *Cancer Res.* 71:3792-3801 (2011)).

SUMMARY OF THE INVENTION

A first aspect of the present invention is directed to a method of identifying a subject having or at risk of developing metastatic liver disease. This method involves measuring, in a sample isolated from the subject, exosomal levels of one or more markers of metastatic liver disease selected from the group consisting of Annexin A1 (ANXA1), CD44, CD47, cadherin 1 (CDH1), filamin A (FLNA), high mobility group box 1 (HMGB1), integrin β3 (ITGB3), lectin galactoside-binding soluble 1 (LGALS1), lectin galactoside-binding soluble 3 (LGALS3), macrophage migration inhibitory factor (MIF), matrix metalloproteinase 14 (MMP14), plasminogen activator urokinase receptor (PLAUR), prostaglandin-endoperoxide synthase 2 (PTGS2), and ras-related C3 botulinum toxin substrate 1 (RAC1). The measured exosomal levels of the one or more markers of metastatic liver disease are compared to exosomal levels of the one or more markers of metastatic liver disease in a control sample. The method further involves identifying the subject as having or at risk of developing liver metastases when the subject has increased exosomal levels of the one or more markers of metastatic liver disease relative to control levels of the one or more markers of metastatic liver disease.

Another aspect of the present invention is directed to a method of identifying a subject having or at risk of developing metastatic liver disease. This methods involves measuring, in a liver cell sample isolated from the subject, expression levels of one or more markers of liver pre-metastatic niche formation selected from the group consisting of matrix metallopeptidase 9 (MMP9), S100 protein B (S100B), S100 protein A8 (S100A8), connective tissue growth factor (CTGF), endothelin-1 (EDN1), platelet-derived growth factor-B (PDGFB), C—C motif chemokine 2 (CCL2), fibroblast growth factor-2 (FGF2), hepatocyte growth factor (HGF), interleukin-1 (IL-1A and IL-1B), interleukin-6 (IL-6), insulin-like growth factor-1 (IGF1), transforming growth factor beta (TGFβ) and vascular endothelial growth factor (VEGF). The measured expression levels of the one or more markers of liver pre-metastatic niche formation are compared to expression levels of the one or more markers of liver pre-metastatic niche formation in a control sample and the subject is identified as having or at risk of developing liver metastases when the subject has increased expression levels of the one or more markers of liver pre-metastatic niche formation relative to control expression levels of the one or more markers of liver pre-metastatic niche formation.

Another aspect of the present invention is directed to a method of inhibiting metastatic liver disease in a subject. This method involves selecting a subject having increased exosomal levels of one or more markers of metastatic liver disease relative to control exosomal levels of the one or more markers of metastatic liver disease where the markers of metastatic liver disease are selected from the group consisting of Annexin A1 (ANXA1), CD44, CD47, cadherin 1 (CDH1), filamin A (FLNA), high mobility group box 1 (HMGB1), integrin β3 (ITGB3), lectin galactoside-binding soluble 1 (LGALS1), lectin galactoside-binding soluble 3 (LGALS3), macrophage migration inhibitory factor (MIF), matrix metalloproteinase 14 (MMP14), plasminogen activator urokinase receptor (PLAUR), prostaglandin-endoperoxide synthase 2 (PTGS2), and ras-related C3 botulinum toxin substrate 1 (RAC1). The method further involves administering to the selected subject, an inhibitor of liver pre-metastatic niche (LPMN) formation in an amount effective to inhibit metastatic liver disease in the subject.

Another aspect of the present invention is directed to a kit suitable for prognosing metastatic liver disease. This kit comprises reagents suitable for detecting exosomal levels of one or more markers of metastatic liver disease selected from the group consisting of Annexin A1 (ANXA1), CD44, CD47, cadherin 1 (CDH1), filamin A (FLNA), high mobility group box 1 (HMGB1), integrin β3 (ITGB3), lectin galactoside-binding soluble 1 (LGALS1), lectin galactoside-binding soluble 3 (LGALS3), macrophage migration inhibitory factor (MIF), matrix metalloproteinase 14 (MMP14), plasminogen activator urokinase receptor (PLAUR), prostaglandin-endoperoxide synthase 2 (PTGS2), and ras-related C3 botulinum toxin substrate 1 (RAC1).

Another aspect of the present invention is directed to a kit suitable for prognosing metastatic liver disease. This kit comprises detection reagents suitable for measuring expression levels of one or more markers of pre-metastatic niche formation selected from the group consisting of matrix metallopeptidase 9 (MMP9), S100 protein B (S100B), S100 protein A8 (S100A8), connective tissue growth factor (CTGF), endothelin-1 (EDN1), platelet-derived growth factor-B (PDGFB), C—C motif chemokine 2 (CCL2), fibroblast growth factor-2 (FGF2), hepatocyte growth factor (HGF), interleukin-1 (IL-1A and IL-1B), interleukin-6 (IL-6), insulin-like growth factor-1 (IGF1), transforming growth factor beta (TGFβ) and vascular endothelial growth factor (VEGF).

Described herein is a detailed analysis of the sequential steps involved in liver pre-metastatic niche formation in the context of pancreatic cancer metastasis. Exosomes derived from both malignant, pre-malignant, and non-malignant pancreatic lesions play a key role in liver pre-metastatic niche initiation. Selective uptake of exosomes by Kupffer cells (KCs) in the liver causes activation of fibrotic pathways, and the establishment of a pro-inflammatory milieu that ultimately supports metastasis. Specifically, exosomal macrophage migration inhibitory factor (MIF) induces the release of transforming growth factor β (TGFβ) by KCs, which, in turn, promotes fibronectin (FN) production by hepatic stellate cells (hStCs). FN deposits subsequently promote the arrest of bone marrow-derived macrophages and neutrophils in the liver, completing the formation of the pre-metastatic niche. MIF knockdown prevents all sequential steps in liver pre-metastatic niche formation and, as a result, blocks exosome-induced PDAC metastasis. Importantly, MIF is elevated in plasma exosomes isolated from a mouse model of pancreatic cancer (PKCY mice) bearing either pancreatic intraepithelial neoplasia (PanIN) or PDAC lesions. Moreover, MIF is also highly expressed in plasma exosomes isolated from PDAC patients whose disease progressed post diagnosis relative to patients with no evidence of disease five years post diagnosis and to healthy control subjects. These observations indicate that exosomal MIF is a marker, as well as a functional component of PDAC liver metastasis. In summary, the studies described herein reveal a previously unknown pro-metastatic circuit through which PDAC-derived exosomes induce the formation of liver pre-metastatic niches that foster the development of metastatic disease.

BRIEF DESCRIPTION OF THE DRAWINGS

FIG. 1A is a representative electron microscope image of exosomes isolated from PAN02 conditioned media. Scale bar, 100 nm. FIG. 1B shows an evaluation of liver metastasis by liver weight (grams) in mice pre-educated with exosomes isolated from a PKCY-mouse model tumor-derived primary cell line (PKCY) or a KPC-mouse model tumor-derived primary cell line (R6560B) before intra-splenic injection with PAN02 cells. Control tumor-bearing mice educated with PBS (TU); n=4 (TU and PKCYexo+TU) and n=3 (R6560Bexo+TU) mice from one experiment. **$P<0.01$,*$P<0.05$, N.S. stands for not significant by ANOVA. Scale bar, 1 cm. Flow cytometric quantification of the frequency of liver and lung cells incorporating PKH67-labeled exosomes is shown in FIG. 1C. Exosomes were isolated from normal pancreas (NP), PAN02, PKCY, and R6560B cells; n=4 (NP) and n=5 (R6560B) mice from one experiment, and n=7 (PAN02) and n=8 (PKCY) mice pooled from two experiments. Statistical source data is described infra in the Examples. **$P<0.01$ by ANOVA. FIG. 1D shows the percentage of PKH67-labeled exosome$^+$ liver cells expressing CD11b and F480 markers (KCs). Exosomes were isolated from human (BxPC-3 and HPAF-II) and murine (R6560B) PDAC cell lines; n=4 (BxPC-3 and HPAF-II) and n=5 (R6560B) mice from one experiment. FIG. 1E is a fluorescence microscopy analysis of PKH67-labeled exosomes (green) and αSMA$^+$ cells, S100A$^+$ fibroblasts, CD31$^+$ endothelial cells, or EpCAM$^+$ epithelial cells (red). Arrows point to fluorescent signal indicating exosome uptake. Scale bars, 50 μm. FIG. 1F shows an analysis of canonical pathways of genes upregulated by Kupffer cells following in vitro education with BxPC-3 exosomes or PBS treatment. The list is comprised of genes related to liver fibrosis. Data was obtained from one experiment performed in triplicate. All data are represented as mean±s.e.m.

FIG. 2A is an evaluation of liver metastasis by liver weight (grams) in mice injected intra-splenically with PAN02 cells (TU, for tumor bearing) following pre-education with phosphate-buffered saline (PBS) or PAN02 exosomes (Exo). Percentage of mCherry$^+$ PAN02 cells in the liver was measured by immunofluorescence (left panels; n=4 mice were pooled from two independent experiments) and livers were weighed (right panel; n=9 (CTL) and n=8 (TU and Exo+TU) mice were pooled from three independent experiments) at day 21 post-PAN02 cell injection. Representative liver images are shown. $P<0.01$ by two-tailed t-test (middle panel), *$P<0.05$ by ANOVA (right panel). Scale bars, immunofluorescence: 200 µm, whole organ images: 1 cm. FIG. 2B shows an evaluation of liver metastasis by liver weight (grams) in mice pre-educated with PBS, exosomes from PAN02 cells, or normal pancreas (NP) prior to intra-splenic injection of PAN02 cells; n=4 (TU) and n=5 (PAN02exo+TU and NPexo+TU) mice from one experiment. P<0.01 by ANOVA. Scale bar, 1 cm. FIG. 2C is a fluorescence microscopy analysis of PKH67-labeled exosome incorporation (green) by F4/80$^+$ Kupffer cells (red). Exosomes were isolated from NP, PAN02, and PKCY cells. Scale bars, 50 µm. Representative flow cytometric profiles of CD11b and F4/80 expression in liver cells treated with unlabeled exosomes or with PKH67-labeled NP or PDAC-derived exosomes (PAN02 and PKCY) are shown in FIG. 2D. Quantification of PKH67-positive liver cells (upper panel) and of PKH67-positive liver cells expressing CD11b and F4/80 (lower panel). For NP, n=4 mice from one experiment; n=7 (PAN02) and n=8 (PKCY) mice pooled from two experiments. *P<0.01, **P<0.01, *P<0.05 by ANOVA. An analysis of canonical pathways enriched in genes upregulated by Kupffer cells following in vitro education with PAN02 or NP exosomes is shown in FIG. 1E. The list is comprised of genes related to liver fibrosis. Data were obtained from one experiment assessing three biologically independent samples. All data are represented as mean±s.e.m.

FIG. 3A shows immunofluorescence quantification in arbitrary units (A.U.) of vitronectin, tenascin C, collagen I and fibronectin (FN) expression in liver after education with PAN02 exosomes (Exo) or PBS (CTL); n=4 mice pooled from two experiments. The data are represented as mean±s.e.m. ***P<0.001 by two-tailed t-test. Scale bars, 200 µm. FIG. 3B shows a fluorescence microscopy analysis of FN expression in αSMA$^+$ hStCs in livers of mice educated with PAN02 exosomes. Line scan for histogram calculation is shown. Scale bars, 50 µm.

FIG. 4A is a fluorescence microscopy analysis showing the lack of co-localization of FN expression with CD31$^+$ endothelial cells in the livers of mice educated with PAN02 exosomes. Scale bar, 50 µm. FIG. 4B shows immunofluorescence quantification of αSMA and FN expression in arbitrary units (a.u.) in the livers of mice educated with PBS (CTL), normal pancreas (NP), PKCY, or R6560B exosomes; n=4 (CTLαSMA; PKCY αSMA; R6560B αSMA and FN) and n=5 (CTL FN; NP αSMA and FN; PKCY FN) mice from one experiment. Scale bars, 150 µm.*P<0.001; N.S. stands for not significant by ANOVA. FIG. 4C shows immunofluorescence quantification of the frequency of F4/80$^+$ cell recruited to the livers of mice educated with PBS (CTL), normal pancreas (NP), PKYC, or R6560B exosomes; n=4 (NP and R6560B) and n=5 (CTL and PKCY) mice from one experiment. Scale bars, 150 µm. P<0.01; N.S. stands for not significant by ANOVA. All data are represented as mean±s.e.m.

FIG. 5A show immunofluorescence quantification of FN expression in arbitrary units (A.U.) (see immunofluorescence images, left panels, and top right graph) and F4/80$^+$ cell frequency in the livers of mice during the course of PAN02 exosome education (bottom right graph); n=4 mice from one experiment. P<0.01, *P<0.001 by ANOVA relative to control (day 0). Scale bars, 100 µm. FIG. 5B shows immunofluorescence quantification of the frequency of bone marrow (BM)-derived F4/80$^+$ (upper, left panels) and Gr1$^+$ (lower, left panels) cells in the liver following transplantation of GFP$^+$ BM from mice educated with PBS (CTL) or PAN02 exosomes (Exo); n=4 (F4/80) and n=3 (Gr1) mice from one experiment. **P<0.01, *P<0.05 by two-tailed t-test. Scale bars, 50 µm. All data are represented as mean±s.e.m.

FIG. 8A is immunofluorescence based quantification of αSMA (left column) and FN (center column) expression and F4/80$^+$ cell frequency (right column) in livers of FN-conditional knockout mice. Cre$^{-/-}$Fn$^{fl/fl}$ (CRE$^-$) and Cre$^{+/-}$Fn$^{fl/fl}$ (CRE$^+$) mice were tamoxifen-treated (TMX) and educated with PAN02 exosomes (Exo). Control PBS-educated livers (CTL): n=3 (CTL F4/80), n=4 (CTL αSMA, FN), n=6 (CRE$^+$ F4/80), n=7 (CRE$^-$ αSMA, F4/80), and n=8 (CRE$^-$ FN; CRE$^+$ αSMA, FN) mice from two experiments. *P<0.001, P<0.01 by ANOVA. FIG. 8B is a graph evaluating liver metastasis by liver weight (grams) in tumor-free mice (CTL), PBS-educated mice injected intra-splenically with PAN02 cells (TU), and tumor-bearing CRE$^-$ and CRE$^+$ mice TMX-treated during Exo education; n=4 (CTL), n=6 (CRE$^-$ and CRE$^+$), and n=10 (TU) mice from three experiments. ***P<0.001, *P<0.05 by ANOVA. FIG. 8C is a graph evaluating liver metastasis in TMX-treated CRE versus CRE$^+$ mice injected intra-splenically with PAN02 cells (TU); n=4 (CRE$^+$) and n=5 (CRE$^-$) mice from one experiment. FIG. 8D is an immunofluorescence based quantification of αSMA (left column) and FN (center column) expression and F4/80$^+$ cell frequency (right column) in mice transiently depleted of CD11b$^+$ cells using a diphtheria toxin (DT)-inducible system during PAN02 exosomes (Exo) education. Control PBS-educated livers (CTL): n=3 (CTL F4/80), n=4 (CTL αSMA, FN; DTR$^-$ αSMA), n=7 (DTR$^-$ FN, F4/80; DTR$^+$αSMA, FN), and n=9 (DTR$^+$ F4/80) mice from two experiments. *P<0.001, P<0.01 by ANOVA. FIG. 8E is a graph evaluating of liver metastasis in tumor-free mice (CTL), PBS-educated mice injected intra-splenically with PAN02 cells (TU), and tumor-bearing CD11b-DTR$^-$ or -DTR$^+$ mice DT-treated during Exo education; n=5 (CTL), n=6 (DTR$^-$), n=9 (DTR$^+$), and n=10 (TU) mice pooled from three experiments. ***P<0.001,

**P<0.01 by ANOVA. FIG. 8F is a graph evaluating liver metastasis in mice transiently depleted of CD11b+ cells and injected intra-splenically with PAN02 cells; n=4 (DTR−) and n=5 (DTR+) mice from one experiment. All data are represented as mean±s.e.m. N.S. for not significant by two-tailed t-test. Scale bars, immunofluorescence: 200 µm, whole organ: 1 cm.

FIG. 10A is a western blot analysis of MIF levels in cells and in exosomes (Exo) of non-infected parental PAN02 cells (WT), PAN02 cells infected with control shRNA (shCTL), MIF knockdown (shMIF), a second construct of MIF knockdown (shMIF(2)), and R6560B cells. FIG. 10B (left panel) shows flow cytometric quantification of PKH67-labeled exosome incorporation by CD11b+ F4/80+ liver cells (KCs), represented as a percentage of all PKH67+ cells; n=4 (WT and shMIF) and n=5 (shCTL and shMIF(2)) mice from one experiment. FIG. 10B (right panel) shows exosome protein quantification, represented as microgram (µg) per 10$^6$ exosomes; n=3 (shCTL, shMIF, and shMIF(2)) and n=4 (WT) independent exosome isolations from in vitro cell culture. N.S. stands for not significant by ANOVA. FIG. 10C shows size distribution analysis of PAN02 exosomes by NanoSight. FIG. 10D shows immunofluorescence quantification of mCherry+ PAN02 cells 24 hours after their intra-splenic injection into mice previously educated for three weeks with parental PAN02 exosomes (Exo) or PAN02shMIF exosomes (shMIF exo). Arrows in representative images indicate PAN02 cells. Control animals were educated with PBS (TU); n=4 mice per cohort from one experiment. **P<0.01 by ANOVA. Scale bars, 100 µm. All data are represented as mean±s.e.m.

FIG. 11A is a panel of representative images and quantification of pre-metastatic niche markers in livers educated with PAN02 exosomes (Exo), PAN02shCTL exosomes (shCTLexo), PAN02shMIF exosomes (shMIFexo and shMIF(2)exo) or PBS control (CTL). Immunofluorescence analysis shows frequency of TGFβ-expressing F4/80+ cells, αSMA and FN expression as well as F4/80+ cell frequency. Inset shows TGFβ+/F4/80+ cell; n=3 (CTL F4/80), n=4 (CTL TGFβ, αSMA, FN; Exo TGFβ; all shCTL; shMIF TGFβ; all shMIF(2), n=6 (Exo F4/80; shMIF F4/80), n=7 (Exo αSMA, FN; shMIF αSMA, FN) mice pooled from two experiments. *P<0.001, P<0.001 by ANOVA. Scale bars, 100 µm. FIG. 11B is a graph evaluating liver metastasis by liver weight (grams) in tumor-free mice (CTL), mice injected intra-splenically with PAN02 cells either pre-educated with PBS (TU), with PAN02 exosomes (Exo+TU), with PAN02 exosomes in combination with A83-01 (Exo+A83-01+TU), or with PAN02shMIF exosomes (shMIFexo+TU); n=4 (Exo+A83-01+TU), n=5 (CTL, TU, Exo+TU, and shMIFexo+TU) mice pooled from two experiments. **P<0.01, *P<0.05 by ANOVA. Scale bar, 1 cm. FIG. 11B is a evaluation of liver metastasis in mice injected intra-splenically with PAN02 cells either pre-educated with PBS (TU), with exosomes isolated from PAN02 cells infected with control shRNA (shCTLexo+TU) or shMIF(2) (shMIF (2)exo+TU) lentiviral vectors; n=4 (shCTLexo+TU), n=5 (shMIF(2)exo+TU) and n=6 (TU) mice from one experiment. *P<0.01 by ANOVA. Scale bar, 1 cm. Enzyme-linked immune assay (ELISA) reveals increased levels of MIF (picogram per 10$^8$ exosomes) in exosomes isolated from patients with pancreatic ductal adenocarcinoma (PDAC) with progression of disease post-diagnosis (POD) compared to PDAC patients with no evidence of disease 5 years post-diagnosis (NED) and to healthy controls (CTL), but not PDAC patients with liver metastasis (LM) as shown in FIG. 11D; n=10 (NED), n=12 (POD), n=15 (CTL) and n=18 (LM) patients. All patient samples were analyzed once as part of three independent ELISA assays. P<0.01 by ANOVA. All data are represented as mean±s.e.m FIGS. 12A-12B show liver pre-metastatic niche formation and increased exosomal MIF levels precede pancreatic ductal adenocarcinoma lesion development in PKCY mice.

FIGS. 19A-19J are a comprehensive list of Kupffer cell genes that are upregulated >1.5-fold by mouse PAN02 exosomes as compared to normal pancreas exosomes (left), and Kupffer cell genes that are upregulated >1.5-fold by BxPC-3 exosomes as compared to PBS (right).

DETAILED DESCRIPTION OF THE INVENTION

Figures 1A, 1B, 1C, 1D, 1E, 1F:
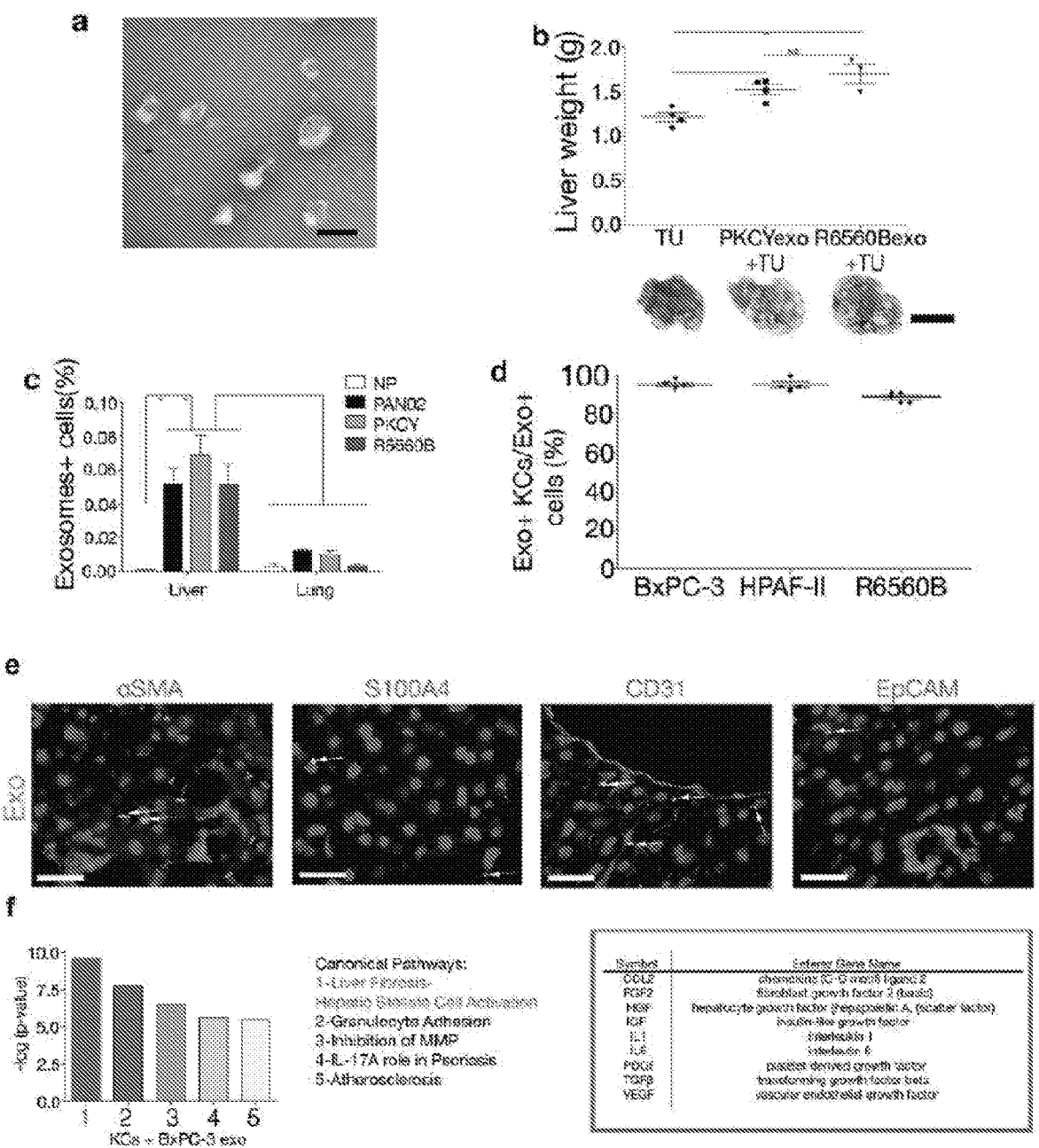
FIGS. 1A-1F show the morphological and functional characterization of pancreatic ductal adenocarcinoma exosomes.

A first aspect of the present invention is directed to a method of identifying a subject having or at risk of developing metastatic liver disease. This method involves measuring, in a sample isolated from the subject, exosomal levels of one or more markers of metastatic liver disease selected from the group consisting of Annexin A1 (ANXA1), CD44, CD47, cadherin 1 (CDH1), filamin A (FLNA), high mobility group box 1 (HMGB1), integrin β3 (ITGB3), lectin galactoside-binding soluble 1 (LGALS1), lectin galactoside-binding soluble 3 (LGALS3), macrophage migration inhibitory factor (MIF), matrix metalloproteinase 14 (MMP14), plasminogen activator urokinase receptor (PLAUR), prostaglandin-endoperoxide synthase 2 (PTGS2), and ras-related C3 botulinum toxin substrate 1 (RAC1). The measured exosomal levels of the one or more markers of metastatic liver disease are compared to exosomal levels of the one or more markers of metastatic liver disease in a control sample. The method further involves identifying the subject as having or at risk of developing liver metastases when the subject has increased exosomal levels of the one or more markers of metastatic liver disease relative to control levels of the one or more markers of metastatic liver disease.

In accordance with this and all aspects of the invention, metastatic liver disease encompasses any disease that spreads from one organ or site in the body, i.e., the primary site of disease, to the liver. Metastatic liver disease typically involves, but is not limited to, the spread of malignant or pre-malignant tumor or cancer cells from a primary tumor site (i.e., primary cancer cells) to the liver. Virtually all gastrointestinal cancers have the potential to metastasize to the liver.

As used herein, "subject" refers to any animal which may be at risk for metastatic liver disease. In one embodiment, the subject is a mammal. Exemplary mammalian subjects include, without limitation, humans, non-human primates, dogs, cats, rodents (e.g., mouse, rat, guinea pig), horses, cattle and cows, sheep, and pigs.

In one embodiment, the subject at risk for metastatic liver disease is a subject having a primary tumor. For example, a subject at risk for metastatic liver disease is a subject having a gastrointestinal tract cancer. Gastrointestinal tract cancers include, without limitation, pancreatic cancer, colorectal cancer, intestinal cancer, stomach cancer, anal cancer, esophageal cancer, gallbladder cancer, and rectal cancer. Alternatively, the subject at risk for metastatic liver disease is a subject having lung or breast cancer. In another embodiment, the subject at risk for metastatic liver disease is a subject having leukemia or lymphoma (e.g., Hodgkin lymphoma). The subject at risk for metastatic liver disease maybe in complete or partial remission from the primary cancer or tumor. In another embodiment, the subject at risk for metastatic liver disease is not in complete or partial remission from the primary cancer or tumor.

In another embodiment, the subject at risk for metastatic liver disease is a subject having a pre-tumoral gastrointestinal lesion, such as, but not limited to pancreatitis, intraductal papillary mucinous neoplasia, pancreatic intraepithelial neoplasia, ulcerative colitis, Chron's disease, inflammatory bowel disease, colon polyps, rectal polyps, *Helicobacter pylori*-associated gastritis, Barrett's esophagus, gallstones, porcelain gallbladder, choledochal cysts, gallbladder polyps, and primary sclerosing cholangitis.

As described herein, exosomal levels of one or more markers of metastatic liver disease are measured to determine whether a subject has or is at risk of developing metastatic liver disease. The exosomal markers of metastatic liver disease identified herein are listed in Table 1 below by their Gene name, Protein name(s), UniProtKB (Universal Protein Resource Knowledge Base) identification number, and GenBank accession numbers. The mRNA and amino acid sequences for these metastatic liver disease markers are well known in the art and widely available to one of skill in the art via their UniProKB or GenBank records (accessible via their UniProtKB identification number or GenBank accession number), both of which are hereby incorporated by reference in their entirety.

TABLE 1

Exosomal Markers of Metastatic Liver Disease

| Gene Name | Protein Name | Alternative Names | UniProtKB Identification No. | GenBank Accession No. mRNA and amino acid sequence |
|---|---|---|---|---|
| ANXA1 | Annexin A1 | Annexin I<br>Annexin-1<br>Calpactin II<br>Calpactin-2<br>Chromobindin-9<br>Lipocortin I<br>Phospholipase A2 inhibitory protein p35 | P04083-1 | X05908 mRNA.<br>Translation: CAA29338.1.<br>BC001275 mRNA.<br>Translation: AAH01275.1.<br>BC035993 mRNA.<br>Translation: AAH35993.1. |
| CD44 | CD44 | CDw44<br>Epican<br>Extracellular matrix receptor III<br>GP90 lymphocyte homing/adhesion receptor<br>HUTCH-I<br>Heparan sulfate proteoglycan<br>X66733 mRNA.<br>Hermes antigen<br>Hyaluronate receptor | P16070<br>(19 isoforms)<br>P16070-1 thru<br>P16070-19 | M24915 mRNA.<br>Translation: AAA35674.1<br>M59040 mRNA.<br>Translation: AAA51950.1.<br>X55150 mRNA.<br>Translation: CAA38951.1.<br>X56794 mRNA.<br>Translation: CAA40133.1.<br>Translation: CAA47271.1. |

TABLE 1-continued

Exosomal Markers of Metastatic Liver Disease

| Gene Name | Protein Name | Alternative Names | UniProtKB Identification No. | GenBank Accession No. mRNA and amino acid sequence |
|---|---|---|---|---|
| CD47 | Leukocyte surface antigen CD47 | Phagocytic glycoprotein 1<br>Phagocytic glycoprotein I<br>Antigenic surface determinant protein OA3<br>Integrin-associated protein (IAP)<br>Protein MER6 | Q08722-1<br>Q08722-2<br>Q08722-3<br>Q08722-4 | X69398 mRNA.<br>Translation: CAA49196.1<br>Z25521 mRNA.<br>Translation: CAA80977.1<br>BT006907 mRNA.<br>Translation: AAP35553.1<br>AK289813 mRNA.<br>Translation: BAF82502.1 |
| CDH1 | Cadherin 1 | CAM 120/80<br>Epithelial cadherin (E-cadherin)<br>Uvomorulin<br>CD324 | P12830-1<br>P12830-2 | Z13009 mRNA.<br>Translation: CAA78353.1.<br>Z18923 mRNA.<br>Translation: CAA79356.1.<br>L08599 mRNA.<br>Translation: AAA61259.1.<br>AB025105 mRNA.<br>Translation: BAA88956.1.<br>AK290012 mRNA.<br>Translation: BAF82701.1<br>AK312551 mRNA.<br>Translation: BAG35448.1. |
| FLNA | Filamin A | Actin-binding protein 280 (ABP-280)<br>Alpha-filamin<br>Endothelial actin-binding protein<br>Filamin-1<br>Non-muscle filamin | P21333-1<br>P21333-2 | X53416 mRNA.<br>Translation: CAA37495.1.<br>GU727643 mRNA.<br>Translation: ADU87644.1.<br>AK090427 mRNA.<br>Translation: BAC03408.2.<br>AB593010 mRNA.<br>Translation: BAJ83965.1. |
| HMGB1 | High mobility group box 1 | High mobility group protein 1 (HMG-1) | P09429-1 | X12597 mRNA.<br>Translation: CAA31110.1.<br>D63874 mRNA.<br>Translation: BAA09924.1.<br>AY377859 mRNA.<br>Translation: AAQ91389.1.<br>AK291494 mRNA.<br>Translation: BAF84183.1.<br>AK122825 mRNA.<br>Translation: BAG53745.1.<br>CR749614 mRNA.<br>Translation: CAH18408.1. |
| ITGB3 | Integrin Beta 3 | | P05106-1<br>P05106-2<br>P05106-3 | J02703 mRNA.<br>Translation: AAA52589.1.<br>M20311 mRNA.<br>Translation: AAA60122.1.<br>M35999 mRNA.<br>Translation: AAA35927.1.<br>U95204 mRNA.<br>Translation: AAB71380.1.<br>BC127666 mRNA.<br>Translation: AAI27667.1.<br>BC127667 mRNA.<br>Translation: AAI27668.1. |
| LGALS1 | lectin, galactoside-binding, soluble, 1 | Galectin-1<br>14 kDa laminin-binding protein (HLBP14)<br>14 kDa lectin<br>Beta-galactoside-binding lectin L-14-I<br>Galaptin<br>HBL<br>HPL<br>Lactose-binding lectin 1<br>Putative MAPK-activating protein PM12<br>S-Lac lectin 1 | P09382-1 | X14829 mRNA.<br>Translation: CAA32938.1.<br>J04456 mRNA.<br>Translation: AAA36170.1.<br>X15256 mRNA.<br>Translation: CAA33328.1.<br>EU363770 mRNA.<br>Translation: ACA58297.1.<br>AB097036 mRNA.<br>Translation: BAC77389.1.<br>CR456511 mRNA.<br>Translation: CAG30397.1.<br>AK312161 mRNA.<br>Translation: BAG35095.1.<br>BT006775 mRNA.<br>Translation: AAP35421.1. |

TABLE 1-continued

Exosomal Markers of Metastatic Liver Disease

| Gene Name | Protein Name | Alternative Names | UniProtKB Identification No. | GenBank Accession No. mRNA and amino acid sequence |
|---|---|---|---|---|
| LGALS3 | lectin, galactoside-binding, soluble, 3 | 35 kDa lectin Carbohydrate-binding protein 35 (CBP 35) Galactose-specific lectin 3 Galactoside-binding protein (GALBP) IgE-binding protein L-31 Laminin-binding protein Lectin L-29 Mac-2 antigen | P17931 | M57710 mRNA. Translation: AAA35607.1. M35368 mRNA. Translation: AAA88086.1. M36682 mRNA. Translation: AAA36163.1. S59012 mRNA. Translation: AAB26229.1. AB006780 mRNA. Translation: BAA22164.1. AK314929 mRNA. Translation: BAG37435.1. CR456897 mRNA. Translation: CAG33178.1. |
| MIF | macrophage migration inhibitory factor | Glycosylation-inhibiting factor (GIF) L-dopachrome isomerase L-dopachrome tautomerase (EC:5.3.3.12) Phenylpyruvate tautomerase | P14174-1 | M25639 mRNA. Translation: AAA36315.1. L10612 mRNA. Translation: AAA35892.1. Z23063 mRNA. Translation: CAA80598.1. AF469046 mRNA. Translation: AAL78635.1. EF611126 mRNA. Translation: ABQ95571.1. CR456520 mRNA. Translation: CAG30406.1. AK311929 mRNA. Translation: BAG34870.1. |
| MMP14 | matrix metalloproteinase 14 (MMP-14) | MMP-X1 Membrane-type matrix metalloproteinase 1 (MT-MMP 1) Membrane-type-1 matrix metalloproteinase (MT1-MMP) | P50281 | D26512 mRNA. Translation: BAA05519.1. X83535 mRNA. Translation: CAA58519.1. Z48481 mRNA. Translation: CAA88372.1. U41078 mRNA. Translation: AAA83770.1. X90925 mRNA. Translation: CAA62432.1. AK291325 mRNA. Translation: BAF84014.1. |
| PLAUR | plasminogen activator, urokinase receptor | Urokinase plasminogen activator surface receptor (uPAR) Monocyte activation antigen Mo3 CD87 | Q03405-1 Q03405-2 Q03405-3 | X51675 mRNA. Translation: CAA35981.1. M83246 mRNA. Translation: AAA59862.1. X74039 mRNA. Translation: CAA52191.1. U09347 mRNA. Translation: AAA17978.1. U08839 mRNA. Translation: AAB60333.1. |
| PTGS2 | prostaglandin-endoperoxide synthase 2 | Prostaglandin G/H synthase 2 Cyclooxygenase-2 (COX-2) PHS II Prostaglandin H2 synthase 2 (PGH synthase 2 or PGHS-2 | P35354 | L15326 mRNA. Translation: AAA35803.1. M90100 mRNA. Translation: AAA58433.1. AY462100 mRNA. Translation: AAR23927.1. AK292167 mRNA. Translation: BAF84856.1. |
| RAC1 | ras-related C3 botulinum toxin substrate 1 | Cell migration-inducing gene 5 protein Ras-like protein TC25 p21-Rac1 | P63000-1 P63000-2 | M29870 mRNA. Translation: AAA36537.1. M31467 mRNA. Translation: AAA36544.1. AJ132694 mRNA. Translation: CAA10732.1. AF136373 mRNA. Translation: AAD30547.1. AY279384 mRNA. Translation: AAQ16632.1. AF498964 mRNA. Translation: AAM21111.1. BT007121 mRNA. Translation: AAP35785.1. |

In one embodiment, the expression level of at least one of the metastatic liver disease markers is measured and compared to a control expression level. Suitable "control" expression values are described infra. In one embodiment, the expression level of at least MIF is measured. In another embodiment, the exosomal expression levels of at least two of the markers are measured and compared to control values. In another embodiment, the exosomal expression levels of at least three of the markers are measured. In another embodiment, the exosomal expression levels of at least four of the markers are measured. In another embodiment the exosomal expression levels of at least 4, 5, 6, 7, 8, 9, 10, 11, 12, 13, or 14 of the markers are measured in a sample and compared to corresponding control values. In one embodiment, the expression levels of at least one, at least two, or at least three of the metastatic markers selected from ANXA1, FLNA, LGALS3, and MIF are measured. In another embodiment, the expression levels of at least ANXA1, FLNA, LGALS3, and MIF are measured.

In accordance with the present invention, exosomal levels of the one or more markers of metastatic liver disease are measured. "Exosomes" are microvesicles released from a variety of different cells, including cancer cells (i.e., "cancer-derived exosomes"). These small vesicles (50-100 nm in diameter) derive from large multivesicular endosomes and are secreted into the extracellular milieu. The precise mechanisms of exosome release/shedding remain unclear; however, this release is an energy-requiring phenomenon, modulated by extracellular signals. Exosomes appear to form by invagination and budding from the limiting membrane of late endosomes, resulting in vesicles that contain cytosol and that expose the extracellular domain of membrane-bound cellular proteins on their surface.

In accordance with the methods of the present invention, exosomes can be isolated or obtained from most biological fluids including, without limitation, blood, serum, plasma, ascites, cyst fluid, pleural fluid, peritoneal fluid, cerebral spinal fluid, tears, urine, saliva, sputum, lymph fluid, fluid of the respiratory, intestinal and genitourinary tracts, breast milk, intra-organ system fluid, or combinations thereof. In one embodiment, the exosomes are isolated or obtained from a gastrointestinal tract fluid, including, but not limited to, pancreatic juice, pancreatic duct fluid, intestinal juice, bile duct fluid, portal vein fluid, lymphatic fluid, and peritoneal fluid.

An enriched population of exosomes can be obtained from a biological sample using methods as described herein or otherwise known in the art. For example, exosomes may be concentrated or isolated from a biological sample using size exclusion chromatography, density gradient centrifugation, differential centrifugation (Raposo et al. "B lymphocytes secrete antigen-presenting vesicles," *J Exp Med* 183 (3): 1161-72 (1996), which is hereby incorporated by reference in its entirety), anion exchange and/or gel permeation chromatography (for example, as described in U.S. Pat. No. 6,899,863 to Dhellin et al., and U.S. Pat. No. 6,812,023 to Lamparski et al., which are hereby incorporated by reference in their entirety), sucrose density gradients or organelle electrophoresis (for example, as described in U.S. Pat. No. 7,198,923), magnetic activated cell sorting (MACS) (Taylor et al., "MicroRNA signatures of tumor-derived exosomes as diagnostic biomarkers of ovarian cancer" *Gynecol Oncol* 110(1): 13-21 (2008), which is hereby incorporated by reference in its entirety), nanomembrane ultrafiltration (Cheruvanky et al., "Rapid isolation of urinary exosomal biomarkers using a nanomembrane ultrafiltration concentrator," *Am J Physiol Renal Physiol* 292(5): F1657-61 (2007), which is hereby incorporated by reference in its entirety), immunoaffinity capture using lectins or antibodies against exosomal markers such as CD63, CD81, EpCAM or Rab5, affinity purification, microfluidic separation, or combinations thereof.

Exosomes isolated from a bodily fluid can be enriched for those originating from a specific cell type, for example, pancreas, stomach, intestine, bladder, kidney, colorectal, prostate, esophagus, or the liver. Because the exosomes often carry surface molecules such as antigens from their donor cells, surface molecules may be used to identify, isolate and/or enrich for exosomes from a specific donor cell type. In this way, the expression levels of metastatic liver disease markers can be measured in exosomes originating from a desired cell population. In one embodiment, tumor (malignant and non-malignant) exosomes carry tumor-associated surface antigens and may be detected, isolated and/or enriched via selection for these specific tumor-associated surface antigens. For example, the cell surface proteoglycan, glypican-1 (GPC1), which is a marker of exosomes derived from pancreatic tumors (Melo et al., "Glypican-1 Identified Cancer Exosomes and Detects Early Pancreatic Cancer," Nature 523(7559):177-82 (2015), which is hereby incorporated by reference in its entirety), can be used to enrich for pancreatic cancer derived exosomes. Alternatively, the epithelial-cell-adhesion-molecule (EpCAM), which is a surface antigen specifically expressed on exosomes from carcinomas of lung, colorectal, breast, prostate, head and neck, and hepatic origin (Balzar et al., "The Biology of the 17-1A Antigen (Ep-CAM)," *J Mol Med* 77(10): 699-712 (1999); Went et al. "Frequent EpCam Protein Expression in Human Carcinomas," *Hum Pathol* 35(1): 122-8 (2004), which are hereby incorporated by reference in their entirety) can be utilized to enrich for exosomes from these tumor types. In yet another example, the surface antigen is CD70, carcinoembryonic antigen (CEA), EGFR, EGFRvIII and other variants, Fas ligand, TRAIL, transferrin receptor, p38.5, p97 and HSP72. Alternatively, tumor specific exosomes may be characterized by the lack of surface markers, such as the lack of CD80 and CD86 expression.

The isolation of exosomes from specific cell types can be accomplished, for example, by using antibodies, aptamers, aptamer analogs or molecularly imprinted polymers specific for a desired surface antigen. In one embodiment, the surface antigen is specific for a cancer type. In another embodiment, the surface antigen is specific for a cell type which is not necessarily cancerous. One example of a method of exosome separation based on cell surface antigen is provided in U.S. Pat. No. 7,198,923, which is hereby incorporated by reference in its entirety. As described in, e.g., U.S. Pat. No. 5,840,867 to Toole and U.S. Pat. No. 5,582,981 to Toole, which are hereby incorporated by reference in their entirety, aptamers and their analogs specifically bind surface molecules and can be used as a separation tool for retrieving cell type-specific exosomes. Molecularly imprinted polymers also specifically recognize surface molecules as described in, e.g., U.S. Pat. Nos. 6,525,154, 7,332,553 and 7,384,589, which are hereby incorporated by reference in their entirety, and are a tool for retrieving and isolating cell type-specific exosomes.

Exosomal "expression levels" is intended to encompass production of any product by a gene including but not limited to transcription of mRNA and translation of polypeptides, peptides, and peptide fragments. Measuring or detecting expression levels encompasses assaying, measuring, quantifying, scoring, or detecting the amount, concentration, or relative abundance of a gene product. It is recognized that a method of evaluating expression of one type of gene product, such as a polypeptide, may not be suitable for assaying another type of gene product, such as a nucleic acid. It is recognized that methods of assaying a gene product include direct measurements and indirect measurements. One skilled in the art is capable of selecting an appropriate method of evaluating expression of a particular gene product.

In one embodiment, exosomal expression levels of the one or more markers of metastatic liver disease are measured using a nucleic acid detection assay. In one embodiment, the DNA levels are measure. In another embodiment, RNA, e.g., mRNA, levels are measured. RNA is preferably reverse-transcribed to synthesize complementary DNA (cDNA), which is then amplified and detected or directly detected. The detected cDNA is measured and the levels of cDNA serve as an indicator of the RNA or mRNA levels present in a sample. Reverse transcription may be performed alone or in combination with an amplification step, e.g., reverse transcription polymerase chain reaction (RT-PCR), which may be further modified to be quantitative, e.g., quantitative RT-PCR as described in U.S. Pat. No. 5,639,606, which is hereby incorporated by reference in its entirety.

In accordance with this embodiment, the exosomal fraction that is isolated from a bodily fluid of a subject can be pre-treated with DNase or RNase to eliminate or substantially eliminate any DNA located on the surface or outside of the exosomes. Without such pre-treatment, short nucleic acid fragments on the outside of the exosomes may remain and co-isolate with nucleic acids extracted from inside the exosomes. Thus, elimination of all or substantially all nucleic acids associated with the outside or surface of the exosomes by pre-treatment of with DNase and/or RNase, has the ability to enrich for internal exosomal nucleic acids (i.e., DNA or RNA).

It may be beneficial or otherwise desirable to extract DNA or RNA from the exosomes prior to or for analysis. DNA and RNA molecules can be isolated from an exosome and the concentration of each (i.e., total DNA or total RNA) quantified using any number of procedures, which are well-known in the art, the particular extraction procedure chosen based on the particular biological sample. In some instances, with some techniques, it may also be possible to analyze the nucleic acid without extraction from the exosome.

In one embodiment, the extracted nucleic acids, including DNA and/or RNA, are analyzed directly without an amplification step. Direct analysis may be performed with different methods including, but not limited to, nanostring technology (Geiss et al. "Direct Multiplexed Measurement of Gene Expression with Color-Coded Probe Pairs," *Nat Biotechnol* 26(3): 317-25 (2008), which is hereby incorporated by reference in its entirety). Nanostring technology enables identification and quantification of individual target molecules in a biological sample by attaching a color coded fluorescent reporter to each target molecule. This approach is similar to the concept of measuring inventory by scanning barcodes. Reporters can be made with hundreds or even thousands of different codes allowing for highly multiplexed analysis. In another embodiment, direct analysis can be performed using immunohistochemical techniques.

In another embodiment, it may be beneficial or otherwise desirable to amplify the nucleic acids of the exosome prior to detection/analysis. Methods of nucleic acid amplification, including quantitative amplification, are commonly used and generally known in the art. Quantitative amplification will allow quantitative determination of relative amounts of the various exosomal nucleic acids.

Nucleic acid amplification methods include, without limitation, polymerase chain reaction (PCR) (U.S. Pat. No. 5,219,727, which is hereby incorporated by reference in its entirety) and its variants such as in situ polymerase chain reaction (U.S. Pat. No. 5,538,871, which is hereby incorporated by reference in its entirety), quantitative polymerase chain reaction (U.S. Pat. No. 5,219,727, which is hereby incorporated by reference in its entirety), nested polymerase chain reaction (U.S. Pat. No. 5,556,773), self sustained sequence replication and its variants (Guatelli et al. "Isothermal, In vitro Amplification of Nucleic Acids by a Multienzyme Reaction Modeled after Retroviral Replication," *Proc Natl Acad Sci USA* 87(5): 1874-8 (1990), which is hereby incorporated by reference in its entirety), transcriptional amplification and its variants (Kwoh et al. "Transcription-based Amplification System and Detection of Amplified Human Immunodeficiency Virus type 1 with a Bead-Based Sandwich Hybridization Format," *Proc Natl Acad Sci USA* 86(4): 1173-7 (1989), which is hereby incorporated by reference in its entirety), Qb Replicase and its variants (Miele et al. "Autocatalytic Replication of a Recombinant RNA." *J Mol Biol* 171(3): 281-95 (1983), which is hereby incorporated by reference in its entirety), cold-PCR (Li et al. "Replacing PCR with COLD-PCR Enriches Variant DNA Sequences and Redefines the Sensitivity of Genetic Testing." *Nat Med* 14(5): 579-84 (2008), which is hereby incorporated by reference in its entirety) or any other nucleic acid amplification method known in the art. Depending on the amplification technique that is employed, the amplified molecules are detected during amplification (e.g., real-time PCR) or subsequent to amplification using detection techniques known to those of skill in the art. Suitable nucleic acid detection assays include, for example and without limitation, northern blot, microarray, serial analysis of gene expression (SAGE), next-generation RNA sequencing (e.g., deep sequencing, whole transcriptome sequencing, exome sequencing), gene expression analysis by massively parallel signature sequencing (MPSS), immune-derived colorimetric assays, and mass spectrometry (MS) methods (e.g., MassARRAY® System).

In another embodiment of the present invention, exosomal protein levels of the one or more markers of metastatic liver disease are measured. Exosomal protein levels can be measured using an immunoassay. Generally, an immunoassay involves contacting the exosomal sample from the subject with one or more binding reagents, e.g., an antibody, where each binding reagent is capable of binding to one of the one or more markers of metastatic liver disease. The binding reagent is coupled to a detectable label, either directly or indirectly. For example, an antibody can be directly coupled to a detectable label or indirectly coupled to a detectable label via a secondary antibody. The one or more labeled binding reagents bound to their respective marker of metastatic liver disease (i.e., a binding reagent-marker complex) in the sample is detected, and the amount of labeled binding reagent that is detected serves as an indicator of the amount or expression level of marker present in the sample. Immunoassays that are well known in the art and suitable for measuring exosomal protein levels of the one or markers of metastatic liver disease include, for example and without limitation, an immunohistochemical assay, radioimmunoassay, enzyme-linked immunosorbent assay (ELISA), immunoradiometric assay, gel diffusion precipitation reaction, immunodiffusion assay, in situ immunoassay, western blot, precipitation reaction, complement fixation assay, immunofluorescence assay, and immunoelectrophoresis assay.

In another embodiment, exosomal protein expression levels are measured using one-dimensional and two-dimensional electrophoretic gel analysis, high performance liquid chromatography (HPLC), reverse phase HPLC, Fast protein liquid chromatograph (FPLC), mass spectrometry (MS), tandem mass spectrometry, liquid crystal-MS (LC-MS) surface enhanced laser desorption/ionization (SELDI), MALDI, and/or protein sequencing.

The exosomal expression levels of the one or more markers of metastatic liver disease is compared to a "control" expression level of the same one or more markers to identify a subject as one that is at risk for metastatic liver disease. In one embodiment, the control expression level of a marker is the average expression level of the marker in exosomal samples taken from a cohort of healthy individuals (i.e., the average expression level in non-cancerous exosomal samples). In another embodiment, the control expression level is the average expression level of the marker in exosomal samples taken from individuals having a primary tumor, e.g., a gastrointestinal tumor, that never metastasized to the liver or other organ of the body. In another embodiment, the control expression level of a marker is the expression level of the marker in an exosomal sample taken from the subject being tested, but at an earlier time point (e.g., a pre-cancerous time point). In all of these embodiments, an increased expression level of the one or more markers of metastatic liver disease in the sample from the subject relative to the control exosomal expression level identifies the subject as having or at risk of developing metastatic liver disease.

An "increased expression level" refers to an expression level (i.e., protein or gene expression level) that is higher than the control level. For example, an increased expression level is at least 10%, at least 20%, at least 30%, at least 40%, at least 50%, at least 80%, at least 100%, at least 2-fold, at least 3-fold, at least 5-fold, at least 10-fold, at least 50-fold or at least 100-fold higher than the control expression level.

In another embodiment, the control expression level of a marker is the average expression level of the marker in exosomal samples taken from individuals having a primary tumor, e.g., a gastrointestinal tumor, that later metastasized. Alternatively, the control expression level of a marker is the average expression level of the marker in exosomal samples taken from individuals with metastatic liver disease. In accordance with this embodiment, when the exosomal expression level of a marker in the subject being tested is the same as the control expression level, the subject is identified as having or at risk of developing metastatic liver disease.

Another aspect of the present invention is directed to a method of identifying a subject having or at risk of developing metastatic liver disease. This methods involves measuring, in a liver cell sample isolated from the subject, expression levels of one or more markers of liver pre-metastatic niche formation selected from the group consisting of matrix metallopeptidase 9 (MMP9), S100 protein B (S100B), S100 protein A8 (S100A8), connective tissue growth factor (CTGF), endothelin-1 (EDN1), platelet-derived growth factor-B (PDGFB), C—C motif chemokine 2 (CCL2), fibroblast growth factor-2 (FGF2), hepatocyte growth factor (HGF), interleukin-1 (IL-1A and IL-1B), interleukin-6 (IL-6), insulin-like growth factor-1 (IGF1), transforming growth factor beta (TGFβ) and vascular endothelial growth factor (VEGF). The measured expression levels of the one or more markers of liver pre-metastatic niche formation are compared to expression levels of the one or more markers of liver pre-metastatic niche formation in a control sample and the subject is identified as having or at risk of developing liver metastases when the subject has increased expression levels of the one or more markers of liver pre-metastatic niche formation relative to control expression levels of the one or more markers of liver pre-metastatic niche formation.

The one or more markers of liver pre-metastatic niche formation can be measured independently or in combination with the one or more exosomal markers of metastatic liver disease as described supra to identify a subject having or at risk of developing liver metastases. As described herein, these markers of liver pre-metastatic niche formation include the gene products (i.e., mRNA or protein) that are upregulated in the Kupffer cells of the liver as a result of exosomal education. A subset of the identified markers of liver pre-metastatic niche formation identified herein are listed in Table 2 below by their Gene name, Protein name(s), UniProtKB (Universal Protein Resource Knowledge Base) identification number, and GenBank accession numbers. The mRNA and amino acid sequences for these pre-metastatic niche formation markers are well known in the art and widely available to one of skill in the art via their UniProtKB or GenBank records (accessible via their UniProtKB identification number or GenBank accession number), both of which are hereby incorporated by reference in their entirety. Additional markers of liver pre-metastatic niche formation (i.e., liver cell genes that are upregulated >1.5 fold upon exosome education) are listed in FIGS. 19A-19J. The methods of the present invention encompass looking at any one or more of the markers of liver pre-metastatic niche formation listed in FIGS. 19A-19J alone or in combination with the markers identified in Tables 1 and 2.

TABLE 2

Markers of Liver Pre-metastatic Niche Formation

| Gene Name | Protein Name | Alternative Names | UniProtKB Identification No. | GenBank Accession No. mRNA and amino acid sequence |
|---|---|---|---|---|
| MMP9 | Matrix metallopeptidase 9 | 92 kDa gelatinase 92 kDa type IV collagenase Gelatinase B (GELB) | P14780 | J05070 mRNA. Translation: AAA51539.1. AK313137 mRNA. Translation: BAG35956.1. BC006093 mRNA. Translation: AAH06093.1. |
| S100B | S100 protein B | S-100 protein beta chain S-100 protein subunit beta S100 calcium-binding protein B | P04271 | CR542123 mRNA. Translation: CAG46920.1. BC001766 mRNA. Translation: AAH01766.1. |

TABLE 2-continued

Markers of Liver Pre-metastatic Niche Formation

| Gene Name | Protein Name | Alternative Names | UniProtKB Identification No. | GenBank Accession No. mRNA and amino acid sequence |
|---|---|---|---|---|
| S100A8 | S100 protein A8 | Calgranulin-A Calprotectin L1L subunit Cystic fibrosis antigen (CFAG) Leukocyte L1 complex light chain Migration inhibitory factor-related protein 8 (MRP-8) (p8) S100 calcium-binding protein A8 Urinary stone protein band A | P05109 | Y00278 mRNA. Translation: CAA68390.1. X06234 mRNA. Translation: CAA29580.1. AK291328 mRNA. Translation: BAF84017.1. CR407674 mRNA. Translation: CAG28602.1. |
| CTGF | connective tissue growth factor | | Q5M8T4 | BC087839 mRNA. Translation: AAH87839.1. |
| EDN1 | Endothelin-1 | Preproendothelin-1 (PPET1) | P05305 | Y00749 mRNA. Translation: CAA68718.1. S56805 mRNA. Translation: AAB25760.1. |
| PDGFB | platelet-derived growth factor subunit B | PDGF-2 Platelet-derived growth factor B chain Platelet-derived growth factor beta polypeptide Proto-oncogene c-Sis | P01127 | X02811 mRNA. Translation: CAA26579.1. X02744 mRNA. Translation: CAA26524.1. M12783 mRNA. Translation: AAA60553.1. |
| CCL2 | C-C motif chemokine 2 | HC11 Monocyte chemoattractant protein 1 Monocyte chemotactic and activating factor (MCAF) Monocyte chemotactic protein 1 (MCP-1) Monocyte secretory protein JE Small-inducible cytokine A2 | P13500 | M24545 mRNA. Translation: AAA18164.1. M28226 mRNA. Translation: AAA60309.1. S71513 mRNA. Translation: AAB20651.1. |
| FGF2 | fibroblast growth factor-2 | Basic fibroblast growth factor (bFGF) Heparin-binding growth factor 2 (HBGF-2) | P09038 | J04513 mRNA. Translation: AAA52531.1. J04513 mRNA. Translation: AAA52532.1. J04513 mRNA. Translation: AAA52533.1. |
| HGF | hepatocyte growth factor | Hepatopoietin-A Scatter factor (SF) | P14210 | M29145 mRNA. Translation: AAA52650.1. X16323 mRNA. Translation: CAA34387.1. M60718 mRNA. Translation: AAA52648.1. |
| IL1A | Interleukin-1 alpha | IL-1 alpha Hematopoietin-1 | P01583 | X02531 mRNA. Translation: CAA26371.1. X02851 mRNA. Translation: CAA26604.1. X56086 mRNA. Translation: CAA39566.1. M28983 mRNA. Translation: AAA59134.1. |
| IL1B | Interleukin-1 beta | Catabolin | P01584 | K02770 mRNA. Translation: AAA36106.1. X02532 mRNA. Translation: CAA26372.1. M15330 mRNA. Translation: AAA59135.1. |

TABLE 2-continued

Markers of Liver Pre-metastatic Niche Formation

| Gene Name | Protein Name | Alternative Names | UniProtKB Identification No. | GenBank Accession No. mRNA and amino acid sequence |
|---|---|---|---|---|
| IL-6 | interleukin-6 | B-cell stimulatory factor 2 (BSF-2) CTL differentiation factor (CDF) Hybridoma growth factor Interferon beta-2 (IFN-beta-2) | P05231 | X04430 mRNA. Translation: CAA28026.1. M14584 mRNA. Translation: AAA52728.1. X04602 mRNA. Translation: CAA28268.1. |
| IGF | Insulin-like growth factor I | Mechano growth factor (MGF) Somatomedin-C | P05019 | M11568 mRNA. Translation: AAA52539.1. M37484 mRNA. Translation: AAA52789.1. X57025 mRNA. Translation: CAA40342.1. |
| VEGF (VEGFA) | vascular endothelial growth factor A (VEGF-A) | Vascular permeability factor (VGF) | P15692 | M32977 mRNA. Translation: AAA35789.1. M27281 mRNA. Translation: AAA36807.1. X62568 mRNA. Translation: CAA44447.1. AJ010438 mRNA. Translation: CAA09179.1. |

In one embodiment, the expression level of at least one of the pre-metastatic niche formation markers is measured and compared to a control expression level. In another embodiment, the expression levels of at least two of the markers are measured and compared to control values. In another embodiment, the expression levels of at least three of the markers are measured. In another embodiment, the expression levels of at least four of the markers are measured. In another embodiment the expression levels of at least 4, 5, 6, 7, 8, 9, 10, 11, 12, 13, or 14 of the markers are measured in a sample and compared to corresponding control values.

The expression level of the one or more markers of liver pre-metastatic niche formation is compared to a "control" expression level of the same one or more markers to identify a subject as one that is at risk for metastatic liver disease. In one embodiment, the control expression level of a marker is the average expression level of the marker in liver samples taken from a cohort of healthy individuals (i.e., the average expression level in non-cancerous liver samples). In another embodiment, the control expression level is the average expression level of the marker in liver samples taken from individuals having a primary tumor, e.g., a gastrointestinal tumor that never metastasized to the liver or other organ of the body. In another embodiment, the control expression level of a marker is the expression level of the marker in a liver sample taken from the subject being tested, but at an earlier time point (e.g., a pre-cancerous time point). In all of these embodiments, an increased expression level of the one or more markers of liver pre-metastatic niche formation in the sample from the subject relative to the control exosomal expression level identifies the subject as having or at risk of developing metastatic liver disease.

As described above, an "increased expression level" refers to an expression level (i.e., protein or gene expression level) that is higher than the control level. For example, an increased expression level is at least 10%, at least 20%, at least 30%, at least 40%, at least 50%, at least 80%, at least 100%, at least 2-fold, at least 3-fold, at least 5-fold, at least 10-fold, at least 50-fold or at least 100-fold higher than the control expression level.

In another embodiment, the control expression level of a marker is the average expression level of the marker in liver samples taken from individuals having a primary tumor, e.g., a gastrointestinal tumor, that later metastasized. Alternatively, the control expression level of a marker is the average expression level of the marker in liver samples taken from individuals with metastatic liver disease. In accordance with this embodiment, when the exosomal expression level of a marker in the subject being tested is substantially the same as the control expression level, the subject is identified as having or at risk of developing metastatic liver disease.

Suitable methods for measuring gene and protein expression levels of the one or more markers of liver pre-metastatic niche formation are described supra.

Another aspect of the present invention is directed to a method of inhibiting metastatic liver disease in a subject. This method involves selecting a subject having increased exosomal expression levels of one or more markers of metastatic liver disease relative to control exosomal expression levels of the one or more markers of metastatic liver disease. The markers of metastatic liver disease are selected from the group consisting of Annexin A1 (ANXA1), CD44, CD47, cadherin 1 (CDH1), filamin A (FLNA), high mobility group box 1 (HMGB1), integrin β3 (ITGB3), lectin galactoside-binding soluble 1 (LGALS1), lectin galactoside-binding soluble 3 (LGALS3), macrophage migration inhibitory factor (MIF), matrix metalloproteinase 14 (MMP14), plasminogen activator urokinase receptor (PLAUR), prostaglandin-endoperoxide synthase 2 (PTGS2), and ras-related C3 botulinum toxin substrate 1 (RAC1). This method further involves administering to the selected subject, an inhibitor of liver pre-metastatic niche (LPMN) formation in an amount effective to inhibit metastatic liver disease in the subject.

In an alternative embodiment, the method involves selecting a subject having increased liver cell expression levels of one or more markers of liver pre-metastatic niche formation relative to control liver cell expression levels of the one or more markers of liver pre-metastatic niche formation. The markers of liver pre-metastatic niche formation are selected from the group consisting matrix metallopeptidase 9 (MMP9), S100 protein B (S100B), S100 protein A8 (S100A8), connective tissue growth factor (CTGF), endothelin-1 (EDN1), platelet-derived growth factor-B (PDGFB), C—C motif chemokine 2 (CCL2), fibroblast growth factor-2 (FGF2), hepatocyte growth factor (HGF), interleukin-1 (IL-1A and IL-1B), interleukin-6 (IL-6), insulin-like growth factor-1 (IGF1), transforming growth factor beta (TGFβ) and vascular endothelial growth factor (VEGF)

In accordance with this aspect of the present invention, the selected subject may also have a primary tumor or cancer, e.g., a gastrointestinal tract cancer, lung tumor, breast tumor, leukemia or lymphoma. In one embodiment, the primary tumor or cancer is in partial remission or complete remission. In another embodiment, the primary cancer or tumor is not in remission. As described supra, gastrointestinal tract cancers, include, without limitation, pancreatic cancer, intestinal cancer, colorectal cancer, stomach cancer, anal cancer, esophageal cancer, gallbladder cancer, and rectal cancer.

The methods for detecting exosomal expression levels of the one or more markers of metastatic liver disease and liver cell expression levels of the one or more markers of pre-metastatic niche formation that are described supra are suitable for identifying subjects that are candidates for the administration of an LPMN inhibitor in accordance with this aspect of the present invention.

As described herein, the induction of liver pre-metastatic niche formation is caused by an increase in transforming growth factor β (TGF β) secretion from Kupffer cells, an upregulation of fibronectin production by hepatic stellate cells, and the recruitment of bone marrow-derived macrophages. All of these changes are orchestrated by the overexpression of MIF in tumor derived exosomes that are taken up by the Kupffer cells. Accordingly, suitable inhibitors of LPMN formation include MIF inhibitors, TGFβ inhibitors, fibronectin inhibitors, macrophage inhibitors, liver fibrosis inhibitors, and any combination of these aforementioned inhibitors.

In one embodiment, the LPMN formation inhibitor is a small molecule MIF antagonist. MIF is a major regulator of inflammation and mediator of the innate immune response. Therefore, MIF has been identified as a therapeutic target for the treatment of various inflammatory and autoimmune diseases. Current development of small molecule inhibitors of MIF has focused on rational structure based design targeting the tautomerase active site of MIF. There are several classes of small molecule MIF tautomerase inhibitors known in the art and suitable for use in accordance with this aspect of the present invention (see Garai and Lóránd, "Macrophage Migration Inhibitory Factor (MIF) Tautomerase Inhibitors as Potential Novel Anti-Inflammatory Agents: Current Developments," Curr. Med. Chem. 16: 1091-1114 (2009), which is hereby incorporated by reference in its entirety). These classes of small molecule MIF antagonists include, without limitation, (i) dopachrome derivatives (see e.g., the dopachrome analogues disclosed in Zhang and Bucala, "Inhibition of Macrophage Migration Inhibitory Factor (MIF) Tautomerase Activity by Dopachrome Analogs," Bioorg. Med. Chem Lett., 9:3193-8 (1999), which is hereby incorporated by reference in its entirety), (ii) acetaminophen derivatives (see e.g., N-acetyl-p-benzoquinone imine (NAPQI) and 3-hydroxy derivatives as disclosed by Senter et al., "Inhibition of Macrophage Migration Inhibitory Factor (MIF) Tautomerase and Biological Activities by Acetaminophen Metabolites," PNAS 99: 144-49 (2002) and U.S. Pat. No. 6,492,428 to Al-Abed et al., which are hereby incorporated by reference in their entirety), (iii) phenylpyruvic acid derivatives (see e.g., the enolacetates described in Haasbroek et al., "Enol Tautomer of the Acetate Ester of 3-methoxy-4-hydroxyphenylpyruvic acid: Crystallographic and NMR spectroscopic Evidence," J. Chem. Cryst., 28: 193-96 (1998), and Haasbroek et al., "Design and Synthesis of 2,4-difluorophenylpyruvic Acid and of its Azlactone Precursor for Macrophage Migration Inhibitory Factor (MIF) Tautomerase Activity," J. Mol. Struc. 690:89-94 (2004), which are hereby incorporated by reference in their entirety), (iv) substituted Schiff bases (see e.g., the substituted Schiff base condensation products disclosed in U.S. Pat. No. 6,599,938 to Al-Abed and Bucala, which is hereby incorporated by reference in its entirety), (v) isoxazoline derivatives including ISO-1 ((S,R)-3-(4-hydroxyphenyl)-4,5-dihydro-5-isoxazole acetic acid methyl ester), and the substituted isoxazoline ring systems described in U.S. Pat. No. 8,552,040 to Al-Abed, Cheng et al., "Critical Modifications of the ISO-1 Scaffold Improve its Potent Inhibition of Macrophage Migration Inhibitory Factor (MIF) Tautomerase Activity," Bioorg. Med. Chem. Lett., 16:3376-79 (2006), and Stojanovic et al., "In vitro, Ex vivo, and In vivo Immuno-pharmacological Activities of the Isoxazoline Compound VGX-1027: Modulation of Cytokine Synthesis and Prevention of Both Organ-Specific and Systemic Autoimmune Diseases in Murine Models," Clin. Immunol. 123: 311-23 (2007), which are hereby incorporated by reference in their entirety, (vi) cinnamates, see e.g. (E)-2-fluoro-p-hydroxycynnamate as disclosed by Taylor et al., "Crystal Structure of Macrophage Migration Inhibitory Factor Complexed with (E)-2-fluoro-p-hydroxycynnamate at 1.8 Å Resolution: Implications for Enzymatic Catalysis and Inhibition," Biochemistry 38: 7444-52 (1999), which is hereby incorporated by reference in its entirety, (vii) acetylenic compounds such as 2-oxo-3-pentynoate and 2-oxo-3-butynoate (see Johnson et al., "Inactivation of 4-oxalocrotonate Tautomerase by 2-oxo-3-pentynoate," Biochemistry 36: 15724-32 (1997) and Taylor et al., "Crystal Structure of 4-oxalocrotonate Tautomerase Inactivated by 2-oxo-3-pentynotate at 2.4 Å Resolution: Analysis and Implications for the Mechanism of Inactivation and Catalysis," Biochemistry 37: 14692-700 (1998), which are hereby incorporated by reference in their entirety), (viii) α,β unsaturated ketones and ketone bodies (1,3-diketones) (see Garai et al., "MIF Tautomerase Inhibitor Potency of α,β-unsaturated Cyclic Ketones," Int. Immunopharmacol. 7: 1741-6 (2007) and Garai et al., "Ketone Bodies Affect the Enzymatic Activity of Macrophage Migration Inhibitory Factor," Life Sci. 77:1375-80 (2005), which are hereby incorporated by reference in their entirety), (ix) plant derived compounds, including natural compounds belonging to phenyl propane and coumarin derivatives (see Garai et al., "Plant-derived Anti-Inflammatory Compounds Affect MIF Tautomerase Activity," Int. Immunopharmacol. 5:849-56 (2005), which is hereby incorporated by reference in its entirety), (v) curcumin and its derivatives (see Garai et al., "Plant-derived Anti-Inflammatory Compounds Affect MIF Tautomerase Activity," Int. Immunopharmacol. 5:849-56 (2005), which is hereby incorporated by reference in its entirety), and (vi) oxygen heterocycles such as 7-hydroxy-coumarins, 7-hydroxychromen-4-ones, 7-hydroxychroman-2,4-diones, and related flavonoids (see Orita et al., "Coumarin and Chromen-4-one Analogues as Tautomerase Inhibitors of Macrophage Migration Inhibitory Factor: Discovery and X-ray Crystallography," J. Med. Chem. 44: 540-47 (2001), which is hereby incorporated by reference in its entirety).

In another embodiment, suitable MIF inhibitors include factors which inhibit MIF release or which inhibit or neutralize MIF activity, such as MIF antisense RNA molecules and MIF monoclonal or polyclonal antibodies and antibody binding fragments and domains thereof. These MIF inhibitors are known in the art and described in, e.g., U.S. Patent Application Publication 2008/0317759 to Bucala and Chesney, which is hereby incorporated by reference in its entirety.

In another embodiment, the LPMN formation inhibitor is a fibronectin inhibitor, such as an inhibitory fibronectin binding peptide or an inhibitory fibronectin antibody. In one embodiment, the inhibitory fibronectin binding peptide is thrombospondin protein fragment, such as those described in U.S. Pat. No. 5,849,701 to Roberts et al., which is hereby incorporated by reference in its entirety. Other peptides suitable for inhibiting fibronectin polymerization and, subsequently, fibronectin deposition include bacterial adhesin derived peptides. Bacterial adhesin based peptides that bind fibronectin and inhibit polymerization include pUR4, $FNZ_{r2}$, and $FNBPA_{9-10}$ as shown in Table 2 below and disclosed in Chiang et al., "Fibronectin Is an Important Regulator of Flow-Induced Vascular Remodeling," *Arterioscler. Thromb. Vasc. Biol.* 29(7):1084-9 (2009), Tomasini-Johansson et al., "Peptide from Adhesin F1 Inhibits Fibronectin Matrix Assembly," *J. Biol. Chem.* 276:23430-23439 (2001), Ozeri et al., "A Two-Domain Mechanism for Group A Streptococcal Adherence Through Protein F to the Extracellular Matrix," *Embo J.* 15(5):989-998 (1996), Lindmark et al., "Fibronectin-Binding Protein of *Streptococcus equi* subsp. *Zooepidemicus*," *Infect. Immun.* 64(10):3993-3999 (1996), and Meenan et al., "The Tandem Beta-zipper Model Defines High Affinity Fibronectin-Binding Repeats within *Staphylococcus aureus* FNBPA," *J. Biol. Chem.* 282(35):25893-25902 (2007), which are hereby incorporated by reference in their entirety).

TABLE 3

Bacterial Adhesin Derived Fibronectin Binding Peptides

| | |
|---|---|
| pUR4 | KDQSPLAGESGETEYITEVYGNQQNPVDIDKKLP NETGFSGNMVETEDT (SEQ ID NO: 1) |
| FNZr2 | RNPHLMGIGGGLAGESGETTPKPGQTGGQGPVIETTEDTQ KGMSGQSGGTIESENTKKPEVMIGGQGQTIETTEDTQKGM SGQSGGTIESEDTKKP (SEQ ID NO: 2) |
| FNBPA 9-10 | YEQGGNIVDIDFDSVPQIHGQNKGNQSFEEDTEKDKPKYE HGGNIIDIDFDSVPHIHGFNKHTEIIEEDTNKDKP (SEQ ID NO: 3) |

Fibronectin binding proteins or polypeptides that are homologous to the bacterial adhesin peptides of Table 3 are also suitable for use in the methods of the present invention. Homologous proteins or polypeptides are preferably characterized by an amino acid sequence identity of at least about 60 percent, at least about 70 percent, at least 80 percent, at least 85 percent, at least 90 percent, or at least 95 percent as compared to the amino acid sequences of SEQ ID NOs 1-3 above.

Other fibronectin binding proteins and polypeptides that are suitable for use in the present invention include fibronectin-derived peptides that inhibit fibronectin polymerization, including the 70-kDa amino terminal fibronectin fragment described by Sottile et al., "Recombinant 70-kDa Protein from the Amino-Terminal Region of Rat Fibronectin Inhibits Binding of Fibronectin to Cells and Bacteria," *Protein Expr. Pur.* 1(2):104-110 (1990) and Sottile et al., "N-Terminal Type I Modules Required for Fibronectin Binding to Fibroblasts and to Fibronectin's III1 Module," *Biochem. J.* 323:51-60 (1997), which are hereby incorporated by reference in their entirety.

In another embodiment, the fibronectin inhibitor comprises an RGD containing peptide that blocks fibronectin by binding to its cell surface receptor, i.e., α5β1. Suitable RGD peptides that inhibit fibronectin are disclosed in, e.g., WO2008045252 to Cochran, WO1998056407 to Cleary, and U.S. Pat. No. 5,627,263 to Ruoslahti, which are hereby incorporated by reference in their entirety.

Antibodies, including monoclonal, polyclonal, and fragments thereof, that bind to fibronectin and inhibit its deposition directly or inhibit its polymerization are also suitable for use in the methods of the present invention. Chernousov et al., "Role of the I-9 and III-1 Modules of Fibronectin in Formation of an Extracellular Fibronectin Matrix," *J. Bio. Chem.* 266(17):10851-58 (1991), which is hereby incorporated by reference in its entirety, describes the isolation and characterization of the 9D2 antibody, which recognizes the first type III module of fibronectin and inhibits fibronectin polymerization and deposition. The 92D antibody and other antibodies, or antibody fragments thereof, directed to similar epitopes of fibronectin are suitable for use in the methods of the present invention. The L8 antibody, which recognizes the region spanning the type I-9 and type III-1 modules of fibronectin, also inhibits fibronectin deposition (Chernousov et al., "Role of the I-9 and III-1 Modules of Fibronectin in Formation of an Extracellular Fibronectin Matrix," *J. Bio. Chem.* 266(17):10851-58 (1991), which is hereby incorporated by reference in its entirety). The L8 antibody and other antibodies or antibody fragments thereof, recognizing similar epitopes of fibronectin are suitable for use in the methods of the present invention.

In another embodiment, the LPMN formation inhibitor is a TGFβ inhibitor. In one embodiment, the TGFβ inhibitor is a small molecule that antagonizes the TGFβ type I receptors, i.e., the activin receptor-like kinases (ALKs), and/or the TGFβ type II receptor. Exemplary TGFβ receptor antagonists known in the art include, but are not limited to those identified in Table 4 below as well as their derivatives and analogues thereof.

TABLE 4

TGFβ Receptor Antagonists

| Name | Chemical Name | Structure | Receptor Target |
|---|---|---|---|
| A83-01[1] | 3-(6-Methyl-2-pyridinyl)-N-phenyl-4-(4-quinolinyl)-1H-pyrazole-1-carbothioamide | 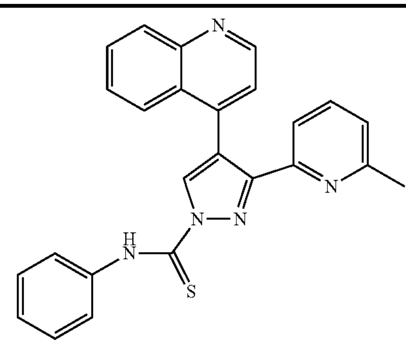 | ALK-5 |

TABLE 4-continued

TGFβ Receptor Antagonists

| Name | Chemical Name | Structure | Receptor Target |
|---|---|---|---|
| SB431542[2] | 4-[4-(1,3-benzodioxol-5-yl)-5-(2-pyridinyl)-1H-imidazol-2-yl]benzamide | 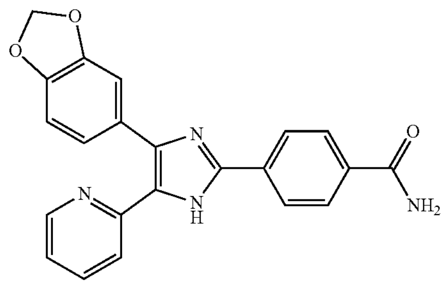 [SMILES: NC(=O)c1ccc(-c2nc(-c3ccc4c(c3)OCO4)c(-c3ccccn3)[nH]2)cc1] | ALK-4 ALK-5 ALK-7 |
| SB505124[3] | 2-[4-(1,3-Benzodioxol-5-yl)-2-(1,1-dimethylethyl)-1H-imidazol-5-yl]-6-methyl-pyridine | 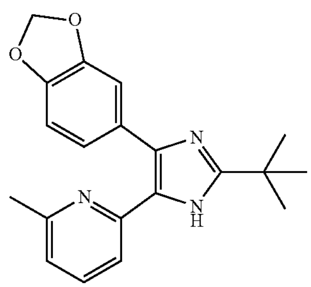 [SMILES: Cc1cccc(-c2[nH]c(C(C)(C)C)nc2-c2ccc3c(c2)OCO3)n1] | ALK-4 ALK-5 ALK-7 |
| SB525334[4] | 6-[2-(1,1-Dimethylethyl)-5-(6-methyl-2-pyridinyl)-1H-imidazol-4-yl]quinoxaline | 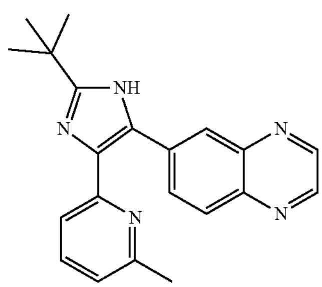 [SMILES: Cc1cccc(-c2nc(C(C)(C)C)[nH]c2-c2ccc3nccnc3c2)n1] | ALK-5 |
| D4476[5] | 4-[4-(2,3-Dihydro-1,4-benzodioxin-6-yl)-5-(2-pyridinyl)-1H-imidazol-2-yl]benzamide | 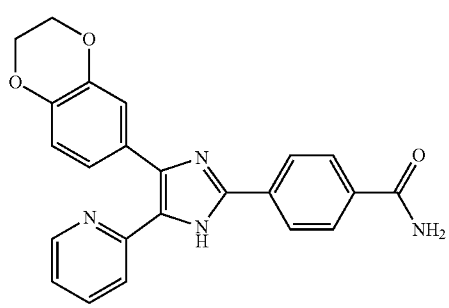 [SMILES: NC(=O)c1ccc(-c2nc(-c3ccc4c(c3)OCCO4)c(-c3ccccn3)[nH]2)cc1] | ALK-5 |
| GW788388[6] | 4-[4-[3-(2-Pyridinyl)-1H-pyrazol-4-yl]-2-pyridinyl]-N-(tetrahydro-2H-pyran-4-yl)-benzamide | 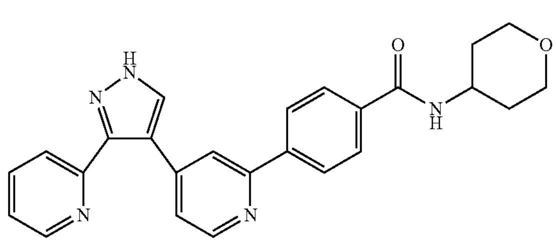 [SMILES: O=C(NC1CCOCC1)c1ccc(-c2cc(-c3c[nH]nc3-c3ccccn3)ccn2)cc1] | ALK5 |

TABLE 4-continued

TGFβ Receptor Antagonists

| Name | Chemical Name | Structure | Receptor Target |
|---|---|---|---|
| LY364947[7] | 4-[3-(2-Pyridinyl)-1H-pyrazol-4-yl]-quinoline | 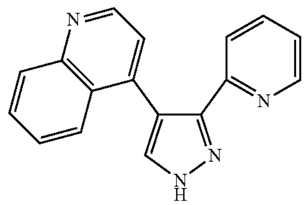 [SMILES: c1ccc(-c2n[nH]cc2-c2ccnc3ccccc23)nc1] | ALK5 |
| R268712[8] | 4-[2-Fluoro-5-[3-(6-methyl-2-pyridinyl)-1H-pyrazol-4-yl]phenyl]-1H-pyrazole-1-ethanol | 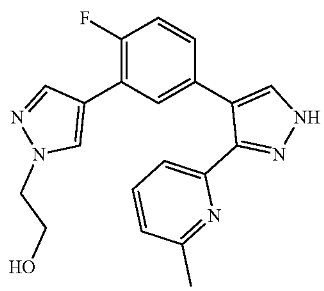 [SMILES: Cc1cccc(-c2n[nH]cc2-c2ccc(F)c(-c3cnn(CCO)c3)c2)n1] | ALK5 |
| SD208[9] | 2-(5-Chloro-2-fluorophenyl)-4-[(4-pyridyl)amino]pteridine | 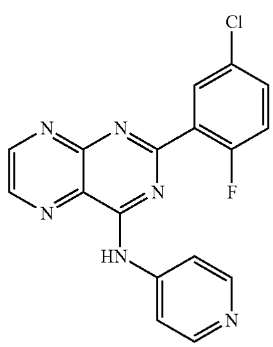 [SMILES: Fc1ccc(Cl)cc1-c1nc(Nc2ccncc2)c2nccnc2n1] | ALK5 |
| RepSox[10] | 2-(3-(6-Methylpyridine-2-yl)-1H-pyrazol-4-yl)-1,5-naphthyridine | 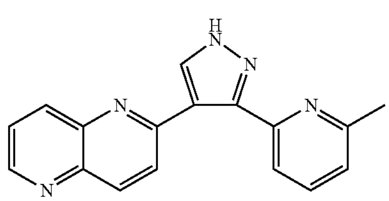 [SMILES: Cc1cccc(-c2n[nH]cc2-c2ccc3ncccc3n2)n1] | ALK5 |
| EW-7203 | (3-((5-([1,2,4]triazolo[1,5-a]pyridin-6-yl)-4-(6-methylpyridin-2-yl)thiazol-2-ylamino)methyl)benzonitrile) | | |
| LY2157299[11] Galunisertib | 4-[5,6-dihydro-2-(6-methyl-2-pyridinyl)-4H-pyrrolo[1,2-b]pyrazol-3-yl]-6-quinolinecarboxamide | 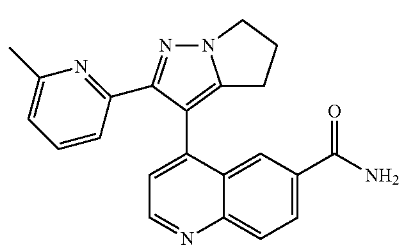 [SMILES: Cc1cccc(-c2nn3c(c2-c2ccnc4ccc(C(N)=O)cc24)CCC3)n1] | ALK5 |

TABLE 4-continued

TGFβ Receptor Antagonists

| Name | Chemical Name | Structure | Receptor Target |
|---|---|---|---|
| LY2109761[12] | 4-[5,6-dihydro-2-(2-pyridinyl)-4H-pyrrolo[1,2-b]pyrazol-3-yl]-7-[2-(4-morpholinyl)ethoxy]-quinoline | 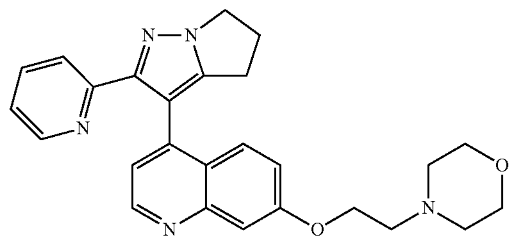 [SMILES: c1ccc(-c2nn3c(c2-c2ccnc4cc(OCCN5CCOCC5)ccc24)CCC3)nc1] | ALK5; TGFβII receptor |
| SM16 | | 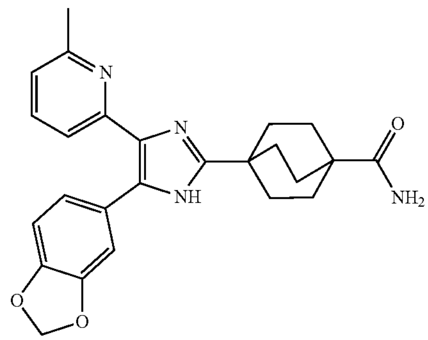 [SMILES: Cc1cccc(-c2nc(C34CCC(C(N)=O)(CC3)CC4)[nH]c2-c2ccc3c(c2)OCO3)n1] | ALK5 |

[1]Tojo et al., "The ALK-5 Inhibitor A-83-01 Inhibits Smad Signaling and Epithelial-to Mesenchymal Transition by Transforming Growth Factor-beta," *Cancer Sci.* 96(11): 791-800 (2005) and U.S. Patent Application Publication No. 20110160210 to Fleenor et al., which are hereby incorporated by reference in their entirety.
[2]Inman et al., "SB-431542 is a Potent and Specific Inhibitor of Transforming Growth Factor-beta Superfamily Type I Activin Receptor-like Kinase (ALK) Receptors ALK4, ALK5, and ALK7," *Mol. Pharmacol.* 62(1): 65-74 (2002), which is hereby incorporated by reference in its entirety.
[3]Byfield et al., "SB-505124 is a Selective Inhibitor of Transforming Growth Factor-β Type I Receptors ALK-4, ALK-5, and ALK-7," *Mol. Pharmacol.* 65: 744 (2004), which are hereby incorporated by reference in their entirety.
[4]Grygielko et al., "Inhibition of Gene Markers of Fibrosis with a Novel Inhibitor of Transforming Growth Factor-beta Type I Receptor Kinase in Puromycin-induced Nephritis," *J. Pharmacol. Exp. Ther.* 313(3): 943-51 (2005), which is hereby incorporated by reference in its entirety.
[5]Callahan et al "Identification of Novel Inhibitors of the Transforming Growth Factor β1 (TGF-β1) Type I Receptor (ALK5)," *J. Med. Chem.* 45: 999 (2002), which is hereby incorporated by reference in its entirety.
[6]Gellibert et al., "Discovery of 4-{4-[3-(pyridin-2-yl)-1H-pyrazol-4-yl]pyridin-2-yl}-N-(tetrahydro-2H-pyran-4-yl)benzamide (GW788388): a potent, selective, and orally active transforming growth factor-β type I receptor inhibitor," *J. Med. Chem.* 49: 2210 (2006), which is hereby incorporated by reference in its entirety.
[7]Sawyer et al., "Synthesis and activity of new aryl- and heteroaryl-substituted pyrazole inhibitors of the transforming growth factor-μ type I receptor kinase domain," *J. Med. Chem.* 46: 3953 (2003), which is hereby incorporated by reference in its entirety.
[8]Terashima et al, "R-268712, an orally active transforming growth factor-β type I receptor inhibitor, prevents glomerular sclerosis in a Thy1 nephritis model," *Eur. J. Pharmacol.* 734: 60 (2014), which is hereby incorporated by reference in its entirety.
[9]Uhl et al., "SD-208, a novel transforming growth factor β receptor I kinase inhibitor, inhibits growth and invasiveness and enhances immunogenicity of murine and human glioma cells in vitro and in vivo," *Cancer Res.* 64: 7954 (2004), which is hereby incorporated by reference in its entirety.
[10]Gellibert et al., "Identification of 1,5-naphthyridine derivatives as a novel series of potent and selective TGF-γ type I receptor inhibitors," *J. Med. Chem.* 47: 4494 (2004), which is hereby incorporated by reference in its entirety.
[11]PCT/US2006/025377 to Mundla et al, which is hereby incorporated by reference in its entirety.
[12]Li, et al., "Optimization of a dihydropyrrolopyrazole series of transforming growth factor-β type I receptor kinase domain inhibitors: Discovery of an orally bioavailable transforming growth factor-β receptor type I inhibitor as antitumor agent," *J Med Chem* 51(7): 2302-2306 (2008), which is hereby incorporated by reference in its entirety.

Another small molecule TGFβ inhibitor suitable for use in accordance with this aspect of the present invention is Halofuginone (Hfg). Hfg is a synthetic derivative of the plant alkaloid febrifugine, a traditional Chinese herbal medicine. Hfg increases expression of Smad7, an intracellular inhibitor of TGF-beta signaling (Juarez et al., "Halofuginone inhibits the establishment and progression of melanoma bone metastases," *Cancer Res.*, 72(23):6247-56 (2012), which is hereby incorporated by reference in its entirety).

Other small molecule inhibitors of TFGβ include any and all of the imidazo[2,1-b][1,3,4]thiadiazole derivatives disclosed in U.S. Pat. No. 8,389,554 to Hoelzemann et al., as well as the small molecule inhibitors of TGFβ signaling disclosed in U.S. Pat. No. 7,511,056 to Diefenbacher et al. and U.S. Patent Publication No. 20110160210 to Fleenor et al., which are hereby incorporated by reference in their entirety.

In another embodiment, the TFGβ inhibitor is an antibody, e.g., monoclonal, polyclonal, and fragments or antibody domains thereof, that bind to TFGβ and inhibit its signaling activity. Suitable TFGβ antibodies are known in the art and include, e.g., LY2382770, a neutralizing monoclonal TFGβ1 antibody, and 1D11, a pan-specific TGFβ neutralizing antibody. Other antibodies known to inhibit TFGβ activity or production that are suitable for use in the methods described herein are disclosed in U.S. Pat. No. 8,569,462 to Bedinger and U.S. Pat. No. 7,147,852 to Gilbertson, respectively, which are hereby incorporated by reference in their entirety.

In another embodiment, the TFGβ inhibitor is an inhibitory peptide. Suitable inhibitor TFGβ inhibitory peptides are known in the art and include, without limitation, P17 (Val Leu Ala Leu Tyr Asn Gln His Asn Pro Gly Ala Ser Ala; SEQ ID NO: 4) and P144 (Thr Ser Leu Asp Ala Ser Ile Ile Tip Ala Met Met; SEQ ID NO: 5) and related peptides described in U.S. Pat. No. 7,057,013 to Ezquerro, which is hereby incorporated by reference in its entirety.

In another embodiment, the TGFβ inhibitor is an inhibitory nucleic acid molecule, such as, but not limited to AP 11014. AP11014 is a TGFβ1 antisense oligonucleotide shown to significantly reduce TGFβ1 secretion in various cancer cell lines (Schlingensiepen et al., "The TGF-beta1 antisense oligonucleotide AP 11014 for the treatment of non-small cell lung, colorectal and prostate cancer: Preclinical studies," *J. Clin. Oncology,* 22(14S): 3132 (2004), which is hereby incorporated by reference in its entirety). Other TGFβ antisense oligonucleotides or inhibitory nucleic acid molecules known in the art can also be employed in the methods of the present invention.

In another embodiment, the LPMN formation inhibitor is a macrophage inhibitor that is capable of preventing macrophages from binding to fibronectin enriched hepatic sites. In one embodiment, the macrophage inhibitor is an antibody capable of binding to a macrophage cell membrane protein such as CSF-1, CD40, DR5, CD64, or the like. In one embodiment, the antibody is conjugated to an anti-tumor agent, e.g., a chemotherapeutic agent or an anti-tumor antibiotic. In this embodiment, the chemotherapeutic agent or other anti-tumor agent coupled to the antibody is delivered in a cell specific manner to induce cell death.

In another embodiment, the macrophage inhibitor is a small molecule. Small molecule macrophage inhibitors that are known in the art and are suitable for use in the methods described herein include, without limitation, doxycycline, GW2580 (5-[[3-Methoxy-4-[(4-methoxyphenyl)methoxy]phenyl]methyl]-2,4-pyrimidinediamine) (Conway et al, Inhibition of Colony-stimulating-factor-1 Signaling In vivo with the Orally Bioavailable cFMS Kinase Inhibitor GW2580," *PNAS* 102(44): 16078-83 (2005), which is hereby incorporated by reference in its entirety), etodolac (Gervais et al., "The Effect of the Non-steroidal Anti-inflammatory Drug Etodolac on Macrophage Migration In vitro and In vivo," *J. Immunopharmacol.* 6(2):205-14 (1984), which is hereby incorporated by reference in its entirety, and dexamethasone. In another embodiment, the macrophage inhibitor is a liposome containing clodronate. Such liposome specifically target and induce macrophage death (van Rooijen and Hendrikx, "Liposomes for Specific Depletion of Macrophages from Organs and Tissue," *Methods Mol. Biol.* 605: 189-203 (2010), which is hereby incorporated by reference in its entirety).

In another embodiment, the LPMN formation inhibitor is an inhibitor of liver fibrosis. As described herein exosomal education activates Kupffer cells and induces liver fibrosis pathways that facilitate liver metastasis. Accordingly, inhibitors of proteins that are known to promote liver fibrosis and are shown herein to be upregulated in Kupffer cells are also suitable for inhibiting LPMN formation. These proteins and their known inhibitors are listed in Table 5 below. In another embodiment, the inhibitor is an inhibitor of any one of the genes/proteins listed in FIGS. 19A-19J.

TABLE 5

Kupffer cell proteins involved in liver fibrosis that are induced by cancer cell exosomes and their known inhibitors

| Molecule | Inhibitors | Molecule | Inhibitors |
|---|---|---|---|
| Connective tissue growth factor (CTGF) | mAb FG-3019 | C-C motif chemokine 2 (CCL2) | CCR2 Antagonist (CAS 445479-97-0) |
| Endothelin (EDN) | Sulfisoxazole | Fibroblast growth factor-2 (FGF2), | Suramin sodium |
| | BQ-123, Sodium Salt | | PD 166866 |
| | BQ-610 | Hepatocyte growth factor (HGF) | SU11274 |
| | CI 1020 | | PHA-665752 |
| | Kendomycin | | JNJ38877605 |
| | BMS 182874 hydrochloride | | Ficlatuzumab |
| | Sclerotiorin | | Rilotumumab |
| | Zibotentan | | TAK-701 |
| | Bosentan | | AMG-208 |
| | Ambrisentan | | BMS-777607 |
| | Sitaxsentan Sodium | | Compound 1 (Amgen) |
| | PD 151,242 | | EMD 1214063/EMD 1204831 h224G11 |
| | Bosentan-d4 | | INC280 |
| | Macitentan | | JNJ38877605 |
| Platelet-derived growth factor (PDGF) | Imatinib mesylate | | Onartuzumab (MetMAb) MK-2461 |
| | Imatinib | | MK-8033 |
| | Tyrphostin A23 | | NK4 |
| | Tyrphostin AG 1295 | | PF4217903 |
| | Tyrphostin 9 | | PHA665752 |
| | AG 494 | | SGX126 |
| | Masitinib | | Tivantinib (ARQ 197) |
| | AP 24534 | | |
| | Motesanib Diphosphate | Interleukin-1 (IL-1) | Suramin sodium |
| | DMPQ dihydrochloride | | Methotrexate-methyl-d3 |
| | Oxindole I | | Methotrexate-methyl-d3, Dimethyl Ester |
| | AG-370 | | 7-Hydroxy Methotrexate-d3 |
| | RG-13022 | | Nilvadipine |
| | 3-(4-Isopropylbenzylidenyl)-indolin-2-one | | Diacerein |
| | VEGFR Tyrosine Kinase Inhibitor IV | | |

TABLE 5-continued

Kupffer cell proteins involved in liver fibrosis that are induced by cancer cell exosomes and their known inhibitors

| Molecule | Inhibitors | Molecule | Inhibitors |
|---|---|---|---|
|  | PP121 | Interleukin-6 (IL-6) | Galiellalactone |
|  | Sunitinib Malate |  |  |
|  | Pazopanib | Vascular endothelial growth factor (VEGF) | Suramin sodium |
|  | PD 161570 |  | NVP-BHG712 |
|  | Dovitinib, Free Base |  | Indole-3-acetamide |
|  | Tyrphostin 47 |  | Nintedanib esylate |
|  | 4,4'-Bis(4-aminophenoxy)biphenyl |  | Lenvatinib |
| MMP9 | GM 6001 |  | 5-Amino-2-methylindole |
|  | ARP 100 |  | Sulochrin |
|  | Actinonin |  |  |
|  | SB-3CT |  |  |
|  | MMP-9 Inhibitor I |  |  |
|  | MMP Inhibitor II |  |  |
|  | MMP-2/MMP-9 Inhibitor II |  |  |
| MMP9 (Cont) | Ageladine A, TFA |  |  |
|  | NNGH |  |  |
|  | MMP-2/MMP-9 Inhibitor V |  |  |
|  | Chlorhexidine, Dihydrochloride |  |  |
|  | MMP-2/MMP-9 Inhibitor I |  |  |
|  | MMP-9/MMP-13 inhibitor I |  |  |
|  | CP 471474 |  |  |
|  | MMP Inhibitor V |  |  |
|  | cis-ACCP |  |  |
|  | ARP 101 |  |  |
|  | MMP-9/MMP-13 Inhibitor II |  |  |
|  | 4-Aminobenzoyl-Gly-Pro-D-Leu-D-Ala hydroxamic acid |  |  |

In accordance with this aspect of the present invention, the LPMN formation inhibitor may be administered alone, in combination with one or more other LPMN formation inhibitors, and/or in combination with another inhibitor of metastatic disease progression, such as, a chemotherapeutic, a radiotherapeutic, an anti-angiogenic therapeutic, a stromal inhibitor, and an extracellular matrix protein inhibitor.

Suitable chemotherapeutic agents for combination therapies include, without limitation, alkylating agents (e.g., chlorambucil, cyclophophamide, CCNU, melphalan, procarbazine, thiotepa, BCNU, and busulfan), antimetabolites (e.g., methotrexate, 6-mercaptopurine, and 5-fluorouracil), anthracyclines (e.g., daunorubicin, doxorubicin, idarubicin, epirubicin, and mitoxantrone), antitumor antibiotics (e.g., bleomycin, monoclonal antibodies (e.g., Alemtuzumab, Bevacizumab, Cetuximab, Gemtuzumab, Ibritumomab, Panitumumab, Rituximab, Tositumomab, and Trastuxmab), platinums (e.g., cisplatin and oxaliplatin) or plant alkaloids (e.g., topoisomerase inhibitors, vinca alkaloids, taxanes, and epipodophyllotoxins).

Anti-angiogenic or anti-vasculogenic therapeutics suitable for use in combination with an LPMN formation inhibitor of the invention include, without limitation a vascular endothelial growth factor (VEGF) inhibitor, basic fibroblast growth factor (bFGF) inhibitor, vascular endothelial growth factor receptor (VEGFR) antagonist, platelet-derived growth factor receptor (PDGFR) antagonist, fibroblast growth factor receptor (FGFR) antagonist, Angiopoietin receptor (Tie-2) antagonist, epidermal growth factor receptor (EGFR, ErbB) antagonist, or any combination thereof. A number of suitable small molecule angiogenic inhibitors are known in the art and are under clinical development (see e.g., Wu et al., "Anti-Angiogenic Therapeutic Drugs for the Treatment of Human Cancer," *J Cancer Molecules* 4(2):37-45 (2008) and Bissell et al., "Why Don't We Get More Cancer? A Proposed Role of the Microenvironment in Restraining Cancer Progression," *Nat. Med.* 17(3):320-329 (2011), which are hereby incorporated by reference in their entirety). These angiogenic inhibitors include, without limitation, Endostatin (an endothelial cell proliferation and angiogenesis inhibitors), Gefitinib (an ErbB inhibitor), Lapatinib (a dual ErbB1/ErbB2 inhibitor), Erlotinib (HER1/EGFR inhibitor), Canertinib (a pan-ErbB inhibitor), Vatalanib (VEGF receptor inhibitor), Imatinib (multi-targeted inhibitor of Bcr-Abl, c-kit, and PDGF-R inhibitor), Sunitinib (multi-targeted inhibitor of VEGFR, PDGFR, Kit, Flt3, Tet and CSF1R), Sorafenib (multi-targeted inhibit of VEGFR and PDGFR), Pazopanib (a multi-targeted inhibitor of VEGFR-1, VEGFR-2, VEGFR-3, PDGF-α, PDGFR-β, and c-kit). Alternatively, the anti-vasculogenic therapeutic is a monoclonal antibody. Suitable antibody therapeutics include, without limitation, Bevacizumab (VEGF antibody), IMC-1C11 (VEGFR-2 antibody), mF4-31C1 (VEGFR-3 antibody), and Vitaxin (integrin $\alpha_v\beta_3$ antibody).

Suitable stromal inhibitors for use in the methods described herein are known in the art (see Bissell et al., "Why Don't We Get More Cancer? A Proposed Role of the Microenvironment in Restraining Cancer Progression," *Nat. Med.* 17(3):320-329 (2011), which is hereby incorporated by reference in its entirety) and include, without limitation, MK-2461 (a small molecule inhibit of c-MET kinase), Anastrazole (an aromatase inhibitor), AMD070 (a CXCR4 inhibitor), IPI-926 (a hedgehog pathway inhibitor), AVE1642 (a humanized monoclonal antibody targeting insulin-like growth factor-1 receptor), BGJ398 (a small molecule inhibitor of fibroblast growth factor receptors), Celecoxib (a COX-2 inhibitor), MK0822 (a cathepsin K inhibitor), Bortezomib (a 26S proteasome complex inhibitor), Zoledronate (a small-molecule pyrophosphate analog that inhibits the differentiation of myeloid cells and affects tumor-associated macrophages), Denosumab (a human monoclonal antibody the binds RANKL), and PG545, a heparan sulfate mimetic that inhibits heparanase activity.

Suitable extracellular matrix protein inhibitors include, without limitation, DX2400, an MMP-14 inhibitor; PEGPH20, a covalently modified form of hyaluronidase which catalyzes the degradation of the extracellular matrix component hyaluronan.

In another embodiment of the present invention, the LPMN inhibitor is administered as a part of an adjuvant therapy regime. In particular, this involves administration of the LPMN formation inhibitor alone or together with chemotherapy, hormone therapy, radiation therapy, immunotherapy, or a targeted therapy prior to and/or after surgery. In addition, the present invention may be used to treat patients after primary surgery who may not otherwise receive treatment, i.e. those patients with primary complete resection without evidence of residual or distant disease in order to prevent liver pre-metastatic niche formation and, therefore, metastatic spread.

Pharmaceutical compositions containing LPMN formation inhibitors suitable for use in the methods of the present invention can include a pharmaceutically acceptable carrier and optionally one or more other active agents packaged together in a suitable delivery vehicle. Suitable delivery vehicles include, but are not limited to viruses, bacteria, biodegradable microspheres, microparticles, nanoparticles, liposomes, collagen minipellets, and cochleates.

In practicing the methods of the present invention, the administering step is carried out to achieve inhibition of liver pre-metastatic niche formation and/or metastatic liver disease progression. Such administration can be carried out systemically or via direct or local administration. By way of example, suitable modes of systemic administration include, without limitation orally, topically, transdermally, parenterally, intradermally, intramuscularly, intraperitoneally, intravenously, subcutaneously, or by intranasal instillation, by intracavitary or intravesical instillation, intraocularly, intraarterialy, intralesionally, or by application to mucous membranes. Suitable modes of local administration include, without limitation, catheterization, implantation, direct injection, dermal/transdermal application, or portal vein administration to relevant tissues, or by any other local administration technique, method or procedure generally known in the art. The mode of affecting delivery of agent will vary depending on the type of therapeutic agent (e.g., an antibody, small molecule, or inhibitory nucleic acid or peptide molecule).

The agents of the present invention may be orally administered, for example, with an inert diluent, or with an assimilable edible carrier, or it may be enclosed in hard or soft shell capsules, or it may be compressed into tablets, or they may be incorporated directly with the food of the diet.

Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

When the LPMN formation inhibitors of the present invention are administered parenterally, solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt Effective doses of the compositions of the present invention, for the treatment of a primary tumor or metastatic disease vary depending upon many different factors, including type and stage of cancer, means of administration, target site, physiological state of the patient, other medications or therapies administered, and physical state of the patient relative to other medical complications. Treatment dosages need to be titrated to optimize safety and efficacy.

Another aspect of the present invention is directed to a kit suitable for prognosing metastatic liver disease that includes detection reagents suitable for measuring exosomal levels of one or more markers of metastatic liver disease using any of the detection/quantitation methods described supra. The markers of metastatic liver disease include, without limitation, annexin A1 (ANXA1), CD44, CD47, cadherin 1 (CDH1), filamin A (FLNA), high mobility group box 1 (HMGB1), integrin β3 (ITGB3), lectin galactoside-binding soluble 1 (LGALS1), lectin galactoside-binding soluble 3 (LGALS3), macrophage migration inhibitory factor (MIF), matrix metalloproteinase 14 (MMP14), plasminogen activator urokinase receptor (PLAUR), prostaglandin-endoperoxide synthase 2 (PTGS2), and ras-related C3 botulinum toxin substrate 1 (RAC1).

In one embodiment, the kit contains reagents to detect at least two markers of metastatic liver disease, at least three markers of metastatic liver disease, at least four markers of metastatic liver disease, at least five markers of metastatic liver disease, or at least 6, 7, 8, 9, 10, 11, 12, 13, or all 14 of the markers of metastatic liver disease.

In one embodiment, the detection reagents of the kit include oligonucleotide primers or probes suitable for measuring the expression of nucleic acid transcripts of the one or more markers of metastatic liver disease by quantitative PCR. In another embodiment, the detection reagents of the kit are oligonucleotide probes suitable for measuring the expression of nucleic acid transcripts of the one or more markers of metastatic liver disease using a nucleic acid hybridization assay, e.g., microarray detection. The kit may include detection reagents for detecting the exosomal expression of at least 1, 2, 3, 4, 5, 6, 7, 8, 9, 10, 11, 12, 13, or all 14 markers of metastatic liver disease. In one embodiment, the kit includes oligonucleotide primers or probes suitable for measuring the expression of MIF. In another embodiment, the kit includes oligonucleotide primers or probes suitable for measuring the expression of ANXA1. In another embodiment, the kit includes oligonucleotide primers or probes suitable for measuring the expression of FLNA. In another embodiment, the kit includes oligonucleotide primers or probes suitable for measuring the expression of LGALS3. In yet another embodiment, the kit includes oligonucleotide primers or probes suitable for measuring any combination of MIF, ANXA1, FLNA, and LGALS3. Oligonucleotide primers suitable for qPCR detection and oligonucleotide probes suitable for nucleic acid hybridization based detection can readily be designed based on the mRNA sequences of the metastatic liver disease markers which are known in the art.

In another embodiment, the detection reagents of the kits are antibodies (e.g., polyclonal or monoclonal) or antibody binding fragments thereof that are suitable for detecting and measuring exosomal levels of the one or more markers of metastatic liver disease using any of the immunoassays described supra. In one embodiment, the kit contains reagents suitable for carrying out an enzyme-linked immunosorbent assay (ELISA), e.g., a solid support coated with antibodies suitable for binding to the one or more markers of metastatic disease, detection antibodies and wash reagents. The kit may include reagents for detecting exosomal protein levels of at least 1, 2, 3, 4, 5, 6, 7, 8, 9, 10, 11, 12, 13, or all 14 markers of metastatic liver disease.

The kit of the present invention may further include detection reagents suitable for measuring expression levels of one or more markers of pre-metastatic niche formation. These markers pre-metastatic niche formation include, without limitation matrix metallopeptidase 9 (MMP9), S100 protein B (S100B), S100 protein A8 (S100A8), connective tissue growth factor (CTGF), endothelin-1 (EDN1), platelet-derived growth factor-B (PDGFB), C—C motif chemokine 2 (CCL2), fibroblast growth factor-2 (FGF2), hepatocyte growth factor (HGF), interleukin-1 (IL-1A and IL-1B), interleukin-6 (IL-6), insulin-like growth factor-1 (IGF1), transforming growth factor beta (TGFβ) and vascular endothelial growth factor (VEGF).

In another aspect of the present invention, the kit suitable for prognosing metastatic liver disease comprises detection reagents suitable for measuring expression levels of one or more markers of pre-metastatic niche formation using any of the detection/quantitation methods described supra. The one or more markers of pre-metastatic niche formation include, without limitation, matrix metallopeptidase 9 (MMP9), S100 protein B (S100B), S100 protein A8 (S100A8), connective tissue growth factor (CTGF), endothelin-1 (EDN1), platelet-derived growth factor-B (PDGFB), C—C motif chemokine 2 (CCL2), fibroblast growth factor-2 (FGF2), hepatocyte growth factor (HGF), interleukin-1 (IL-1A and IL-1B), interleukin-6 (IL-6), insulin-like growth factor-1 (IGF1), transforming growth factor beta (TGFβ) and vascular endothelial growth factor (VEGF).

In one embodiment, the kit contains reagents to detect at least two markers of pre-metastatic niche formation, at least three markers of pre-metastatic niche formation, at least four markers of pre-metastatic niche formation, at least five markers of pre-metastatic niche formation, or at least 6, 7, 8, 9, 10, 11, 12, 13, or 14 of the markers of pre-metastatic niche formation. Suitable detection reagents, e.g., oligonucleotide primers, probes, and antibodies are described supra.

Kits provided herein may comprise a carrier, package or container that is compartmentalized to receive one or more container such as vials, tubes, and the like. A kit provided herein may comprise additional containers comprising materials desirable from a commercial, clinical or user standpoint, including but not limited to, buffers, diluents, filters, needles, syringes, and package inserts with instructions for use. A kit may also contain positive or negative controls and may provide a known sample to be used as a predetermined standard or control. A kit may provide information pertaining to a predetermined standard or control such as information pertaining to a predetermined range.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

EXAMPLES

Material and Methods for Examples

Cells.

Primary cultures of murine pancreatic ductal adenocarcinomas (PKCY) were obtained by dissociating cells from tumours of a 20-week-old Pdx1 Cre transgenic mouse (Gu et al., "Direct Lineage Tracing Reveals the Ontogeny of Pancreatic Cell Fates During Mouse Embryogenesis," *Mech. Dev.* 120: 35-43 (2003), which is hereby incorporated by reference in its entirety) in which a Rosa$^{YFP}$ allele is expressed concurrently with pancreas-specific mutations in p53 and Kras, referred to as PKCY mice (Rhim et al., "EMT and Dissemination Precede Pancreatic Tumor Formation," Cell 148:349-361 (2012), which is hereby incorporated by reference in its entirety). The murine pancreatic tumour cell line with high metastatic potential to the liver, R6560B, was isolated from tumours of a Pdx1-Cre transgenic mouse (Gu et al., "Direct Lineage Tracing Reveals the Ontogeny of Pancreatic Cell Fates During Mouse Embryogenesis," Mech. Dev. 120: 35-43 (2003), which is hereby incorporated by reference in its entirety) with pancreas-specific mutations in p53 and Kras and was generously provided by D. L. Bajor (Vonderheide laboratory, University of Pennsylvania). The C57Bl/6 murine pancreatic adenocarcinoma cell line PAN02 (also identified as Panc 02) was purchased from the DTP, DCTD Tumor Repository, NIH. MIF knockdown PAN02 cells were generated by using MIF shRNA lentiviral particle infection, generating the PAN02 variants shMIF (sc-37138-V, Santa Cruz) and shMIF(2) (iV042354, abmGood). As a control, PAN02 cells were infected with control shRNA lentiviral particles-A (sc-108080, Santa Cruz). In all cases, infected cells were selected with puromycin according to the manufacturer's instructions. For several experiments, exosomes were isolated from human PDAC cell lines BxPC-3 and HPAF-II (ATCC). For in vitro education of human Kupffer cells (Life Technologies) with healthy normal pancreas-derived exosomes (NP), PAN02, or BxPC-3 exosomes, cells were maintained in culture for 14 days, with media containing 0 or 5 μg ml$^{-1}$ of exosomes, replenished every other day. Cells were cultured in RPMI supplemented with 10% exosome-depleted FBS (FBS, Gibco) and penicillin-streptomycin, and maintained in a humid incubator with 5% $CO_2$ at 37° C. FBS was depleted of bovine exosomes by ultracentrifugation at 100,000 g for 70 min (min). In some experiments, normal pancreas exosomes were obtained by culturing 25 pancreata isolated from healthy 4-6-week-old mice in 3 ml of FBS-free RPMI for 12 hr.

Exosome Isolation, Characterization and Analyses.

Isolation of exosomes for mass spectrometry and all other experiments was done by ultracentrifugation. Exosome preparation was verified by electron microscopy. Supernatant fractions collected from 72-h cell cultures or plasma samples were pelleted by centrifugation at 500 g for 10 min. The supernatant was centrifuged at 12,000 g for 20 min. Exosomes were then collected by centrifugation at 100,000 g for 70 min. The exosome pellet was resuspended in 20 ml of phosphate-buffered saline (PBS) and collected by ultracentrifugation at 100,000 g for 70 min (Beckman Ti70). Exosome size and particle number were analyzed using the LM10 or DS500 nanoparticle characterization system (NanoSight) equipped with a blue laser (405 nm). MIF levels in exosomes were measured by ELISA (ab100594, Abcam for human samples; ABIN415583, Antibodies Online for mouse samples), using 2 μg of exosomes per 100 μl of sample diluent, in duplicate reactions, according to the manufacturer's instructions.

Proteomics.

Mass spectrometry analyses of exosomes were performed using 10 μg of exosomal protein. Samples were denatured using 8M urea, reduced using 10 mM dithiothreitol, and alkylated using 100 mM iodoacetamide. This was followed by proteolytic digestion with endoproteinase LysC (Wako Chemicals) overnight at room temperature, and subsequent digestion with trypsin (Promega) for 5 h at 37° C. The digestion was quenched with formic acid and the resulting peptide mixtures were desalted using in-house-made C18 Empore (3M) StAGE tips. Samples were dried and solubilized in the sample loading buffer containing 2% acetonitrile and 2% formic acid. Approximately 3-5 μg of each sample was analyzed by reversed-phase nano-LC-MS/MS (Ultimate 3000 coupled to QExactive, Thermo Scientific). Following loading on the C18 trap column (5 μm beads, Thermo Scientific) at a flow rate of 3 μl min$^{-1}$, peptides were separated using a 75-μm-inner-diameter C18 column (3 μm beads Nikkyo Technos) at a flow rate of 200 nl min$^{-1}$, with a gradient increasing from 5% Buffer B (0.1% formic acid in acetonitrile)/95% Buffer A (0.1% formic acid) to 40% Buffer B/60% Buffer A, over 140 min. All LC-MS/MS experiments were performed in data-dependent mode. Precursor mass spectra were recorded in a 300-1,400 m/z mass range at 70,000 resolution, and 17,500 resolution for fragment ions (lowest mass: m/z 100). Data were recorded in profile mode. Up to 20 precursors per cycle were selected for fragmentation and dynamic exclusion was set to 45 s. Normalized collision energy was set to 27. Data were extracted and searched against Uniprot complete Human or Mouse proteome databases (January 2013) concatenated with common contaminants using Proteome Discoverer 1.4 (Thermo Scientific) and Mascot 2.4 (Matrix Science). All cysteines were considered alkylated with acetamide. Amino-terminal glutamate to pyroglutamate conversion, oxidation of methionine, and protein N-terminal acetylation were allowed as variable modifications. Data were first searched using fully tryptic constraints. Matched peptides were filtered using a Percolator-based 1% false discovery rate. Spectra not being matched at a false discovery rate of 1% or better were re-searched allowing for semi-tryptic peptides. The average area of the three most abundant peptides for a matched protein was used to gauge protein amounts within and in between samples.

Exosome Treatment and Labelling.

Five micrograms of total exosomal protein was injected into the retro-orbital venous sinus in a total volume of 100 μl PBS. For education experiments, mice received 5 μg of exosomes every other day, 3 times a week. For exosome-tracking experiments, purified exosomes were fluorescently labelled using PKH67 membrane dye (Sigma). Labelled exosomes were washed in 20 ml of PBS, collected by ultracentrifugation, and resuspended in PBS. In experiments involving evaluation of exosome incorporation, labelled exosomes were injected 24 h before tissue collection and analysis for exosome$^+$ cells was conducted by flow cytometry or immunofluorescence. For exosome-tracking experiments, 5 μg of non-tumour exosomes from normal pancreas were used as controls. Unlabeled exosomes were used as controls of signal specificity. For education experiments, retro-orbital injection of PBS or normal pancreata exosomes was used in control groups.

Illumina Strand-Specific RNA Sequencing.

To analyze the genes whose expression was altered in human KC cells as a result of in vitro education with normal pancreas, PAN02, or BxPC-3 exosomes, total RNA was isolated using the RNeasy Mini Kit (QIAGEN). Experiments were performed in triplicate. Illumina sequencing libraries were constructed by following a modified strand-specific RNA-Seq protocol (Zhong et al., "High Throughput Illumina Strand-Specific RNA Sequencing Library Preparation," Cold Spring Harb. Protoc. 2011: 940-949 (2011), which is hereby incorporated by reference in its entirety). The library was then PCR amplified with TruSeq-indexed PCR primers and sequenced using the Illumina HiSeq2000 platform (Weill Cornell Medical College).

Human Studies.

Human studies were approved by the Weill Cornell Medical College, Institution Review Board no. 0604008488. Human peripheral blood samples were obtained from control healthy subjects and PDAC patients with liver metastasis or from patients without longstanding liver metastasis (approximately 5 years) at Weill Cornell Medical College, Oslo University Hospital, Memorial Sloan Kettering Cancer Center, and University of Nebraska Medical Center, all pathologically confirmed. All individuals provided informed consent for blood donation on approved institutional protocols. Blood was collected in purple-top tubes containing EDTA, and centrifuged at 500 g for 10 min. Plasma exosomes were isolated as described above in the Exosome Isolation, Characterization and Analyses section.

Mouse Strains and Treatments.

All mouse work was performed in accordance with institutional, IACUC, and AAALAS guidelines, animal protocol no. 0709-666A. Six-week-old C57Bl/6 female mice were used for all animal experiments. For CD11b$^+$ cell depletion, B6.FVB-Tg-(ITGAM-DTR) mice (Jackson Laboratories, stock 006000) were injected intraperitoneally with 150 ng of diphtheria toxin diluted in 100 µl of PBS every other day during the second week of exosome education. As a control, wild-type C57Bl/6 mice received a similar regimen of treatment. CD11b$^+$ cell depletion from the liver was verified by immunofluorescence or flow cytometry for F4/80$^+$ cells and CD11b$^+$ F4/80$^+$ cells, respectively.

To generate inducible FN knockout mice, we crossed B6; 129-Gt(ROSA)26SOR$^{tm1(cre/ERT2)Tyj}$/J mice expressing tamoxifen-sensitive Cre under the Gt(Rosa)26 or promoter (Jackson Laboratories, stock 008463) with mice homozygous for a floxed allele of fibronectin (Fn$^{fl/fl}$, generously provided by R. Fässler, Max Planck Institute of Biochemistry) (Sakai et al., "Plasma Fibronectin Supports Neuronal Survival and Reduces Brain Injury Following Transient Focal Cerebral Ischemia but is Not Essential for Skin-Wound Healing and Hemostasis," *Nat. Med.* 7:324-330 (2001), which is hereby incorporated by reference in its entirety). Cre$^{-/-}$Fn$^{fl/fl}$ mice were then maintained by breeding to Fn$^{fl/fl}$ mice. Both Cre$^{+/-}$Fn$^{fl/fl}$ (CRE$^+$) and Cre$^{-/-}$Fn$^{fl/fl}$ (CRE$^-$) control mice were treated with intraperitoneal injections of 40 µg of tamoxifen (Sigma) per gram of mouse weight (diluted in 100 µl of olive oil) every other day for a total of 3 doses, during the second week of PAN02 exosome education. For verification of Fn deletion, liver FN expression was evaluated by immunofluorescence.

For evaluation of liver pre-metastatic niche formation in a spontaneous mouse model of PDAC, we used the p53- and Kras-driven mouse model of pancreatic cancer (Rhim et al., "EMT and Dissemination Precede Pancreatic Tumor Formation," *Cell* 148:349-361 (2012), which is hereby incorporated by reference in its entirety), termed PKCY. PKCY mice were evaluated at different ages, during the early and late stages of PanIN lesions (4-6 and 8-11 weeks, respectively), and at the PDAC stage (16-20 weeks). As controls, livers isolated from mice that do not develop pancreatic lesions (Cre transgenic lacking activating TP53 and Kras mutations, referred to here as CY) were used.

For systemic TGFβ receptor inhibition, mice were treated with intraperitoneal injections of A83-01 (Santa Cruz). Mice were administered 10 µg of A83-01 (diluted in 100 µl of dimethylsulphoxide) per gram of mouse weight for a total of 9 doses, every other day, for the three weeks of PAN02 exosome education.

Liver Metastasis Studies.

To analyze the role of exosome education in tumour metastasis, 6-8-week-old C57Bl/6 female mice pre-educated with PDAC-derived exosomes were injected intrasplenically with 1×10$^6$ PAN02 mCherry cells resuspended in 30 µl of Matrigel (Corning) as previously described (Little et al., "Novel Immunocompetent Murine Models Representing Advanced Local and Metastatic Pancreatic Cancer," *J. Surg. Res.* 176:359-366 (2012); Suemizu et al., "A Versatile Technique for the In Vivo Imaging of Human Tumor Xenografts Using Near-Infrared Fluorochrome-Conjugated Macromolecule Probes," *PLoS ONE* 8:e82708 (2013); Morikawa et al., "In Vivo Selection of Highly Metastatic Cells From Surgical Specimens of Different Primary Human Colon Carcinomas Implanted Into Nude Mice," *Cancer Res.* 48:1943-1948 (1988), which are hereby incorporated by reference in their entirety). Either 24 h or 21 days later, mice were euthanized and livers were analyzed for metastatic lesions by counting mCherry$^+$ cells by fluorescence microscopy or measuring liver weights. All animals were monitored for abnormal tissue growth or ill effects according to AAALAS guidelines and euthanized if excessive deterioration of animal health was observed.

GFP Bone Marrow Transplantation.

Bone marrow transplantation was performed by reconstituting the bone marrow of lethally irradiated (950 rads) C57Bl/6 female 6-week-old mice through retro-orbital injection of 5×10$^6$ total bone marrow cells isolated from eGFP transgenic mice (Jackson Laboratory). After 4 weeks, the eGFP bone marrow-reconstituted C57Bl/6 mice were educated with PBS or PAN02 exosomes for 21 days.

Tissue Processing and Immunofluorescence.

For histological analysis, tissues were dissected and fixed in a mix of 2% PFA and 20% sucrose solution overnight, and then embedded in Tissue-tek O.C.T. (Electron Microscopy Sciences). Blocks were frozen in a dry ice and ethanol bath. For immunofluorescence, 6 µm O.C.T. tissue cryosections were stained with antibodies against F4/80 (14-4801-85, 1:100, eBioscience), fibronectin (sc59826, 1:50, Santa Cruz), αSMA (CBL171, 1:500, EMD Millipore), Gr-1 (ab25377, 1:50, Abcam), CD31 (sc59906, 1:100, Santa Cruz), S100A4 (ab27957, 1:100, Abcam), epCAM (sc59906, 1:50, Santa Cruz) and TGFβ (ab66043, 1:100, Abcam). In some experiments, ECM evaluation was done by using antibodies directed against collagen I (ab6308, 1:100, Abcam), vitronectin (sc15332, 1:100, Santa Cruz) and tenascin C (ab6346, 1:100, Abcam). Secondary antibodies conjugated to Alexa Fluor 488, 555 or 594 were used (a11007, a11001 or a21424, respectively, 1:1,000, Life Technologies). GFP and mCherry' cells were detected by their intrinsic signal. Fluorescent images were obtained using a Nikon confocal microscope (Eclipse TE2000U) and analyzed using Nikon software (EZ-C1 3.6). FN and αSMA expression were quantified using ImageJ Software (NIH) by determining the ratio between the areas of FN and DAPI staining, expressed in arbitrary units (a.u.).

SDS-PAGE and Western Blot.

Equal amounts of cell lysate or exosome lysate were resuspended in 1.5× Laemmli buffer, subsequently incubated at 95° C. for 5 min and centrifuged in a microcentrifuge at 13,000 g. for 5 min. Samples were separated on a Novex 4-12% Bis-Tris Plus Gel (Life Technologies), and transferred onto a PVDF membrane (Millipore). The membrane was activated in 100% methanol and rinsed with double-distilled H$_2$O (ddH$_2$O) before transfer.

After transfer, membranes were processed for Ponceau red staining. For that, PVDF membranes were rinsed in ddH$_2$O and immersed in 100% methanol for 5 s. Membranes were dried for 15 min on Whatman paper and reactivated in 100% methanol for 5 s. Reactivated membranes were rinsed in ddH$_2$O and incubated with Ponceau red solution (BIO-RAD) for 3 min. The de-stained membranes were then used further for antibody incubations in ready-to-use Odyssey blocking buffer (OBB, Li—COR, Part No. 927-40000) and blocked for 1 h at room temperature. Primary anti-MIF antibody (ab175189, 1:1,500, Abcam) was diluted in OBB containing 0.1% Tween-20, and incubated overnight at 4° C. Membranes were then washed 4× (5 min each) with TBS containing 0.1% Tween-20 (TBS-T) at room temperature. Secondary antibodies conjugated to anti-rabbit IRDye 800CW (Li—COR, 1:20,000) were diluted in OBB containing 0.1% Tween-20 and 0.01% SDS. Membranes were incubated with secondary antibody solutions for 1 h at room temperature with boxes wrapped in aluminium foil to prevent light exposure.

Afterwards membranes were washed 4 times (5 min each) with TBS-T at room temperature in the dark, and then briefly rinsed 2 times (2 min each) in PBS before scanning Membranes were scanned and analyzed using an OdysseyH IR scanner using OdysseyH imaging software 3.0. Scan settings were lowest image quality, 42 µm resolution, auto intensity for both 700 and 800 channels with no offset.

Flow Cytometry Analysis.

For labelled exosome tracking and phenotypic analysis of murine organs, femurs were flushed and livers were mechanically dissociated, and single-cell suspensions were filtered through a 40 µm strainer. Cells were washed in PBS with 1% BSA and incubated with anti-CD11b-PerCP-Cyanine5.5 (clone M1/70, 1:100, BD Biosciences) and anti-F4/80-APC (clone BM8, 1:100, eBioscience) antibodies at predetermined saturating concentrations. PKH67-labelled exosome-positive cells were detected using blue laser excitation and 488 nm emission. Data for 1,000,000 cells were acquired on a BD FACS Canto cytometer with Diva software (BD) and were analyzed using FlowJo software (TreeStar).

Statistical and Pathway Analysis.

Error bars in graphical data represent means±s.e.m. Statistical significance was determined using a two-tailed Student's t-test or by ANOVA. P<0.05 was considered statistically significant. Statistical analyses were performed using GraphPad Prism software. Pathway analyses were performed using Ingenuity IPA software (Ingenuity Systems). No statistical method was used to predetermine sample size. The experiments were not randomized, and the investigators were not blinded to allocation during experiments and outcome assessment.

Accession Codes.

The raw sequencing data for human Kupffer cells treated in vitro with PAN02 or normal pancreas exosomes or BxPC-3 exosomes have been deposited in the GEO database under accession number GSE66876. The raw data for proteomic analysis of PAN02 tumour exosomes have been deposited in the FigShare database.

Figures 2A, 2B, 2C, 2D, 2E:
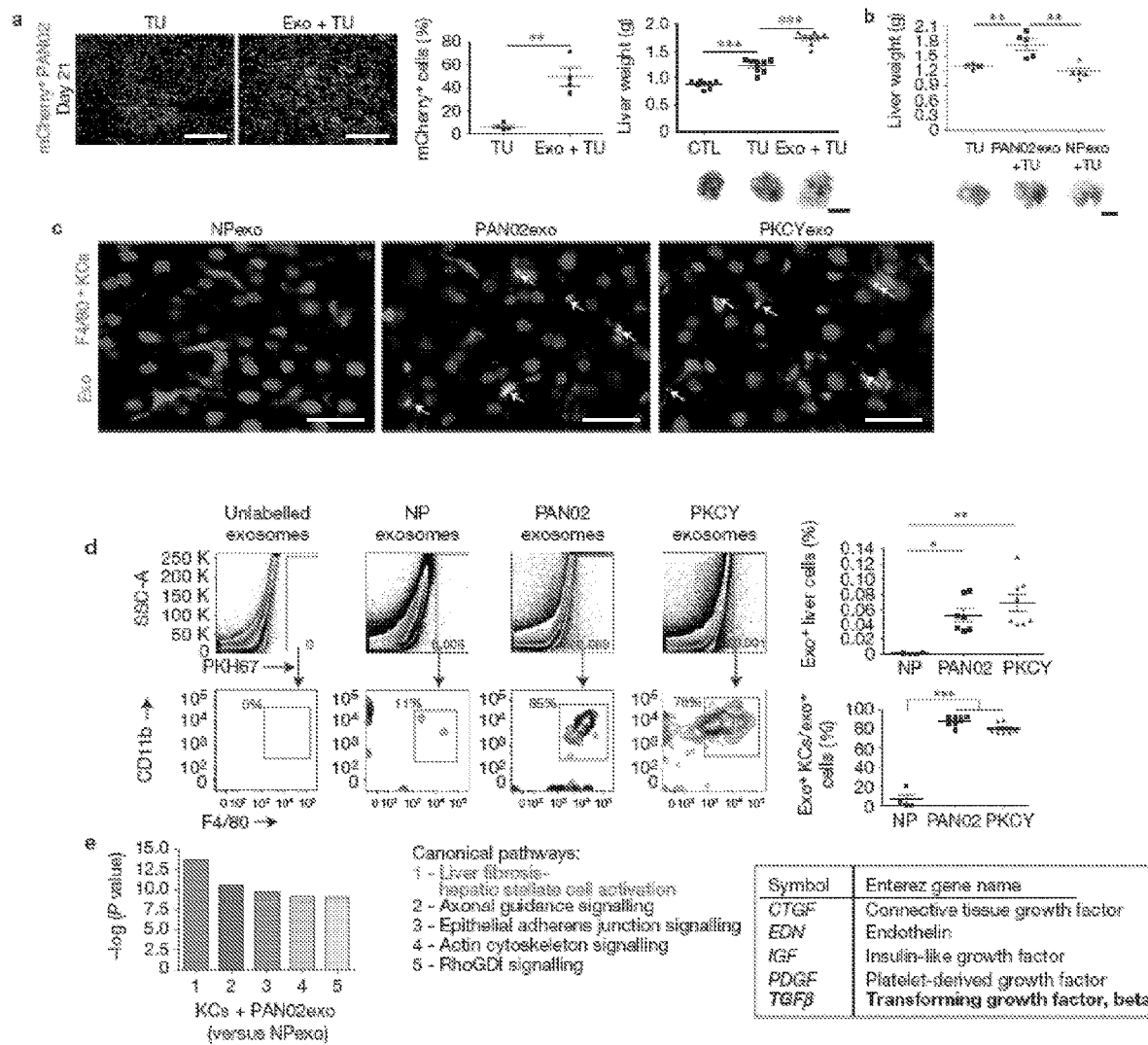
FIGS. 2A-2E show pancreatic ductal adenocarcinoma-derived exosomes target and activate Kupffer cells, induce liver fibrosis pathways, and increase liver metastasis.

Example 1—Pancreatic Ductal Adenocarcinoma-Derived Exosomes Preferentially Fuse with Kupffer Cells and Enhance Metastatic Burden in Liver To determine if PDAC-derived exosomes play a role in liver metastasis, an experimental model of intra-splenic injection of PAN02 murine PDAC cells (Corbett et al., "Induction and Chemotherapeutic Response of Two Transplantable Ductal Adenocarcinomas of the Pancreas in C57BL/6 Mice," Cancer Res. 44:717-726 (1984); Little et al., "Novel Immunocompetent Murine Models Representing Advanced Local and Metastatic Pancreatic Cancer," J. Surg. Res. 176:359-366 (2012), which are hereby incorporated by reference in their entirety) was used. This model typically generates metastases restricted to the liver. The structure of PAN02-derived exosomes was first analyzed by electron microscopy, which revealed a typical exosome structure and size of approximately 100 nm (FIG. 1A). Naïve, wild-type mice were injected retro-orbitally every other day for three weeks with 5 µg of PAN02-derived exosomes in a process defined as "education" (Peinado et al. "Melanoma Exosomes Educate Bone Marrow Progenitor Cells Toward a Pro-Metastatic Phenotype Through MET," Nature Med. 18:883-891 (2012), which is hereby incorporated by reference in its entirety). After exosome education, mCherry+ PAN02 cells were injected intra-splenically (into the portal circulation) and the incidence of liver metastasis was analyzed. Exosome education increased macrometastatic burden 21 days after injection, as demonstrated by quantification of mCherry+ cells (FIG. 2A, left and middle panels) and by measurement of liver weight (FIG. 2A, right panel). A control cohort educated with exosomes isolated from conditioned media of primary cultures of normal pancreas tissue from tumor-free mice (NP) did not cause an increase in metastatic burden (FIG. 2B). Furthermore, education with exosomes derived from two additional murine PDAC cell lines isolated from tumors developed in the KPC (Hingorani et al., "Trp53R172H and KrasG12D Cooperate to Promote Chromosomal Instability and Widely Metastatic Pancreatic Ductal Adenocarcinoma in Mice," Cancer Cell 7:469-483 (2005), which is hereby incorporated by reference in its entirety) and PKCY (Rhim et al., "EMT and Dissemination Precede Pancreatic Tumor Formation," Cell 148:349-361 (2012), which is hereby incorporated by reference in its entirety) mouse models (hereon referred to as R6560B and PKCY, respectively) resulted in increased liver metastatic burden, as assessed 3 weeks after injection of PAN02 cells (FIG. 1B). These data suggest that PDAC-derived exosomes may support early tumor cell engraftment and metastasis by conditioning metastatic organs with favorable microenvironments (i.e., pre-metastatic niches).

The cells that uptake tumor exosomes in the liver following retro-orbital injection of labeled PDAC-derived exosomes in naïve mice were evaluated. Fluorescently labeled exosomes isolated from several PDAC models were used, including PAN02, PKCY and R6560B, as well as human BxPC-3 and HPAF-II PDAC cells. The frequency of exosome positive cells in a million cells from each organ was analyzed. Although PDAC-derived exosomes first circulate through the lung due to the retro-orbital injection methodology, they were more frequently represented in the liver than in the lung (FIG. 1C). In addition, over 80% of liver cells that uptake exosomes were F4/80+ or F4/80+CD11b+, a phenotype consistent with Kupffer cells (KCs) (FIGS. 2C, 2D and FIG. 1D). In contrast, control exosomes isolated from healthy normal mouse pancreas were not efficiently incorporated by KCs or other tissues analyzed (FIGS. 2C, 2D and FIG. 1C). Importantly, PDAC exosomes failed to fuse with other cells in the liver microenvironment, such as αSMA+ cells, S100A4+ fibroblasts, CD31+ endothelial cells, or EpCAM+ epithelial cells (FIG. 1E). Therefore, our data suggest that KCs are the predominant cell type that uptakes PDAC-derived exosomes and likely responsible for promoting the initial steps of liver pre-metastatic niche formation.

To further define mechanisms involved in liver pre-metastatic niche formation by KCs, human KCs were educated with PAN02 or BxPC-3 exosomes in vitro and gene expression analysis was performed by mRNA sequencing. Of more than 300 canonical pathways, the liver fibrosis pathways—particularly those associated with the upregulation of genes encoding soluble factors such as MMP9, S100B, S100A8, CTGF, EDN, IGF, PDGF, and TGFβ (FIG. 2E and FIG. 1F)—were the most highly expressed and over-represented.

Figures 3A, 3B:
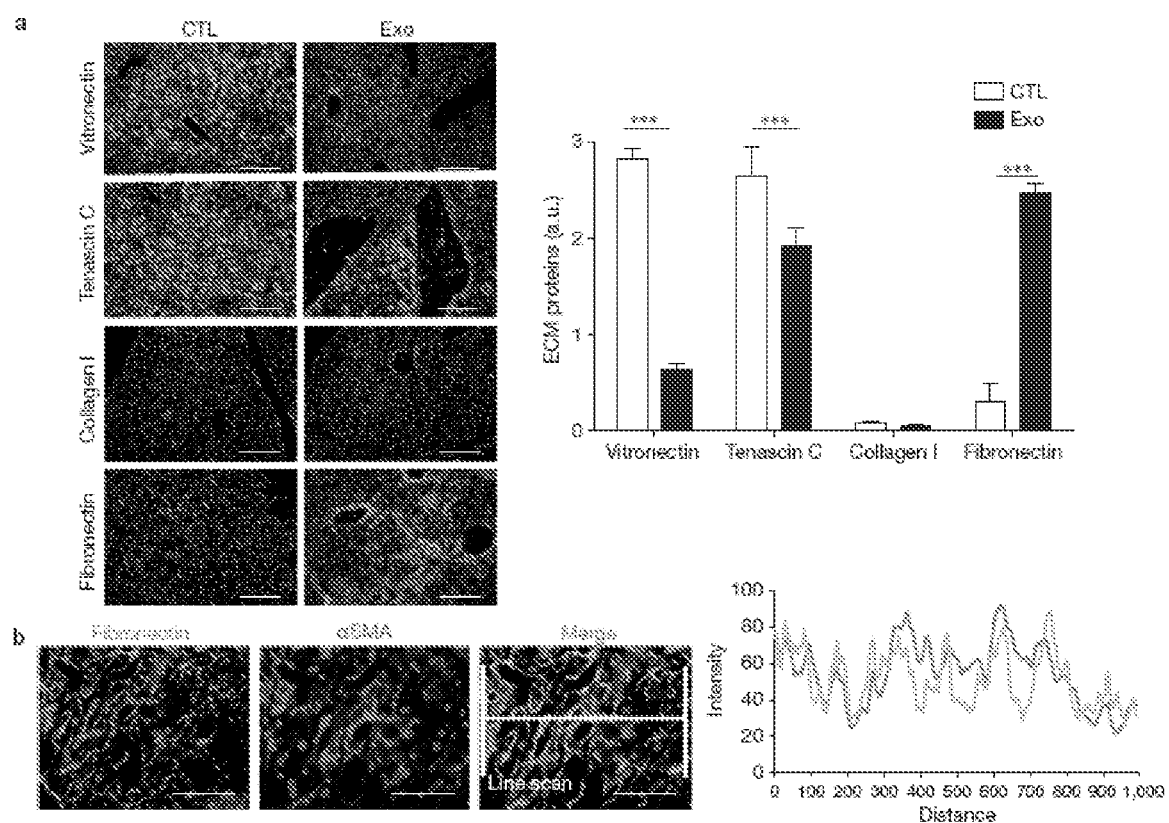
FIGS. 3A-3B depict the role of pancreatic ductal adenocarcinoma-derived exosome education in extracellular matrix component expression and liver pre-metastatic niche formation.
Figures 4A, 4B, 4C:
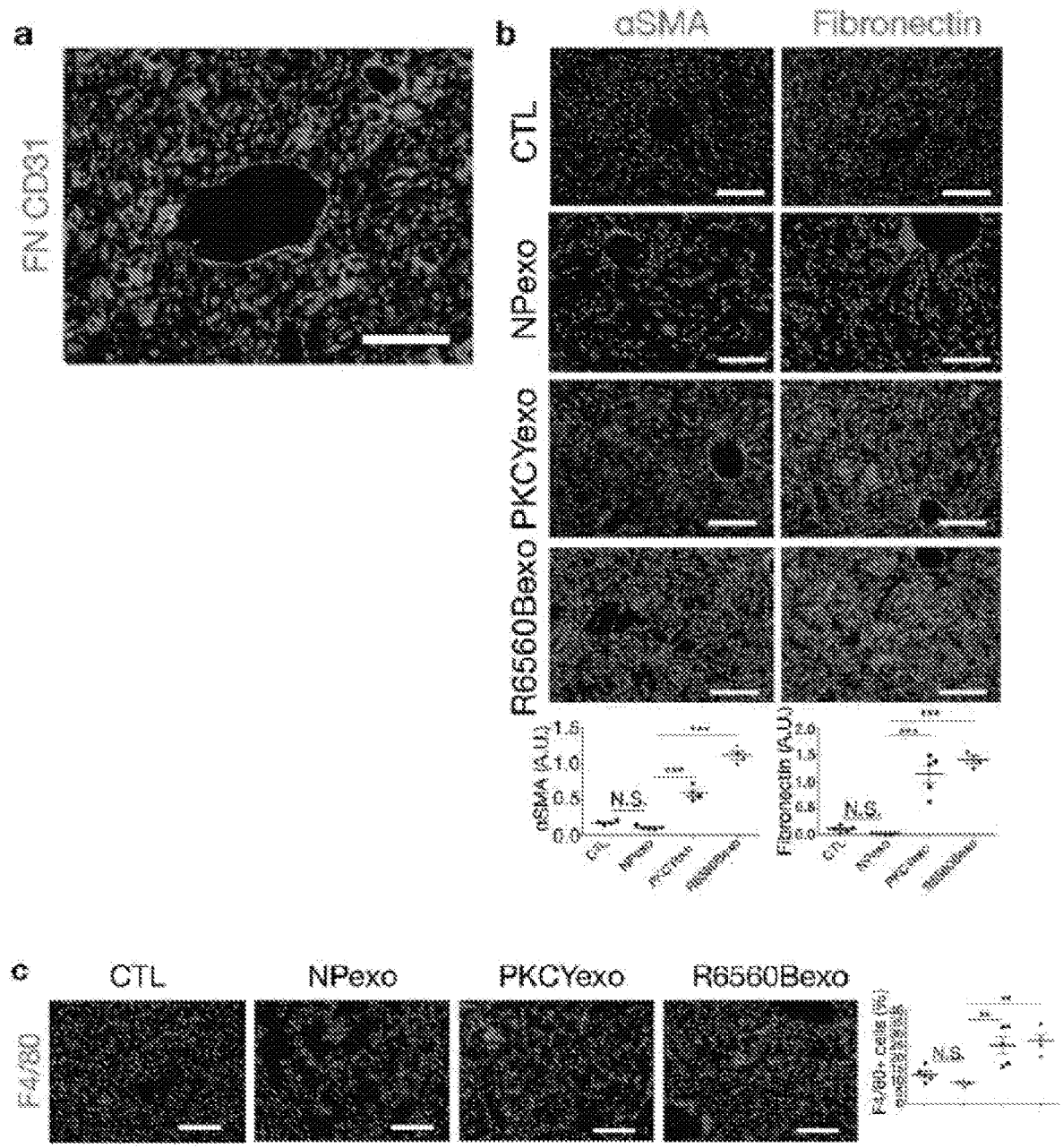
FIGS. 4A-4C show pancreatic ductal adenocarcinoma-derived exosomes induce αSMA and FN expression and increase F4/80$^+$ cell frequency in the liver and migration of BM-derived macrophages to the liver.

Example 2—Fibronectin Upregulation by Hepatic Stellate Cells is Important for Liver Pre-Metastatic Niche Formation by Pancreatic Ductal Adenocarcinoma-Derived Exosomes To determine how PDAC-derived exosomes elicit a fibrotic liver microenvironment, the changes in expression of different extracellular matrix (ECM) proteins following PAN02 exosome education were examined by immunofluorescence. A downregulation of vitronectin and tenascin C, a stable but minimal expression level of collagen type I, and a marked increase in fibronectin (FN) expression were observed (FIG. 3A). Next the source of FN upregulation by PDAC-derived exosomes was investigated by co-staining sections of pre-metastatic livers with antibodies against FN and CD31 or αSMA. A predominant population of αSMA$^+$ FN$^+$ cells was found in FN-enriched areas of educated livers, but there was a lack of FN and CD31 co-staining (FIG. 3A), suggesting that activated hepatic stellate cells (hStCs) produced most of the FN (FIG. 3B). In contrast to education with NP-derived exosomes, education of naïve mice with PKCY or R6560B cell-derived exosomes also increased αSMA and FN expression in the liver (FIG. 4B). These results demonstrate an induction of FN production by hStCs and support the hypothesis that PDAC-derived exosomes can establish a fibrotic liver pre-metastatic niche.

Figures 5A, 5B:
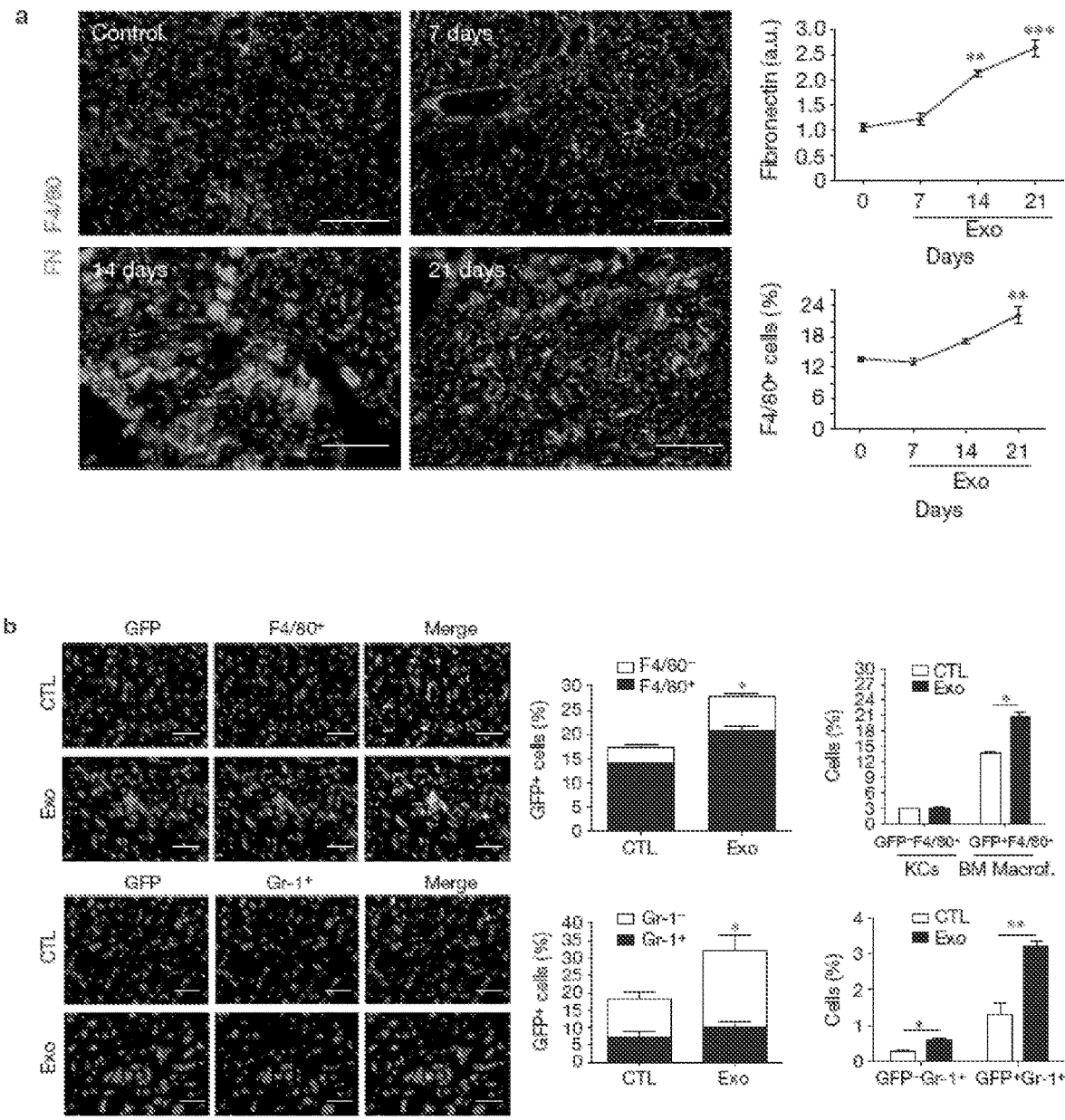
FIGS. 5A-5B shows that pancreatic ductal adenocarcinoma-derived exosomes induce fibronectin expression and migration of bone marrow-derived cells to the liver.

Example 3—Pancreatic Ductal Adenocarcinoma-Derived Exosomes Induce Bone Marrow-Derived Cell Migration to Liver To evaluate if PDAC-derived exosomes play a role in preparing the liver microenvironment for the arrival of metastatic cells by eliciting macrophage recruitment, wild-type mice were educated with exosomes isolated from PAN02, PKCY, or R6560B cells. Interestingly, PDAC exosomes, but not NP exosomes, were sufficient to increase the frequency of macrophage marker F4/80-expressing cells in the liver (FIG. 4A and FIG. 4C). A detailed time course analysis during the three-week PAN02 exosome education showed a significant increase in FN levels as early as the second week of exosome education. By the third week of education, a significant and sustained increase in the levels of F4/80$^+$ cells was observed in the liver compared to livers that had not been educated (FIG. 5A). Moreover, to determine if the increase in macrophage frequency was the result of bone marrow (BM)-derived macrophage recruitment, GFP-expressing BM cells were transplanted into irradiated wild-type C57Bl/6 mice, followed by PAN02 exosome education and F4/80 immunostaining. An overall increase in GFP$^+$ cells was observed in the liver after exosome education, with approximately 67% of these cells being F4/80$^+$ (FIG. 5B, upper panels). Importantly, the GFP$^-$ F4/80$^+$ population, likely composed of liver resident KCs, remained unchanged after PAN02 exosome education (FIG. 5B, upper-right panel). Furthermore, a smaller subset, approximately 30% of the GFP$^+$ cells, was positive for the myeloid differentiation marker Gr-1, and this population also increased in the liver following PAN02 exosome education (FIG. 5B, lower panels). These results indicate that PAN02 exosome education promotes recruitment of BM-derived cells to the liver, including F4/80$^+$ macrophages and, to a lesser extent, Gr-1$^+$ neutrophils.

Figure 6:
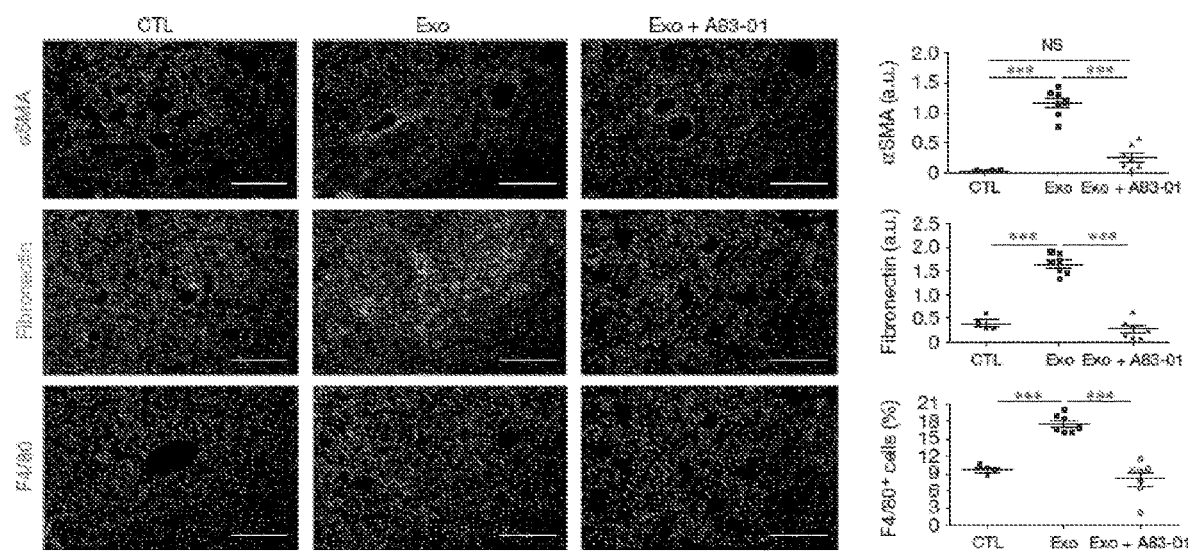
FIG. 6 shows TGFβ signaling induces fibronectin upregulation and macrophage recruitment to the liver pre-metastatic niche. Immunofluorescence quantification of FN and αSMA expression in arbitrary units (A.U.) (top and center panels) and F4/80$^+$ cells (bottom panels) in livers of mice educated with PBS (CTL), PAN02 exosomes alone (Exo), or in combination with the TGFβ receptor inhibitor A83-01 (Exo+A83-01); n=4 (CTL) and n=7 (Exo and Exo+A83-01) mice pooled from two experiments. The data are represented as mean±s.e.m. ***P<0.001, N.S. stands for not significant by ANOVA. Scale bars, 200 µm.
Figure 7:
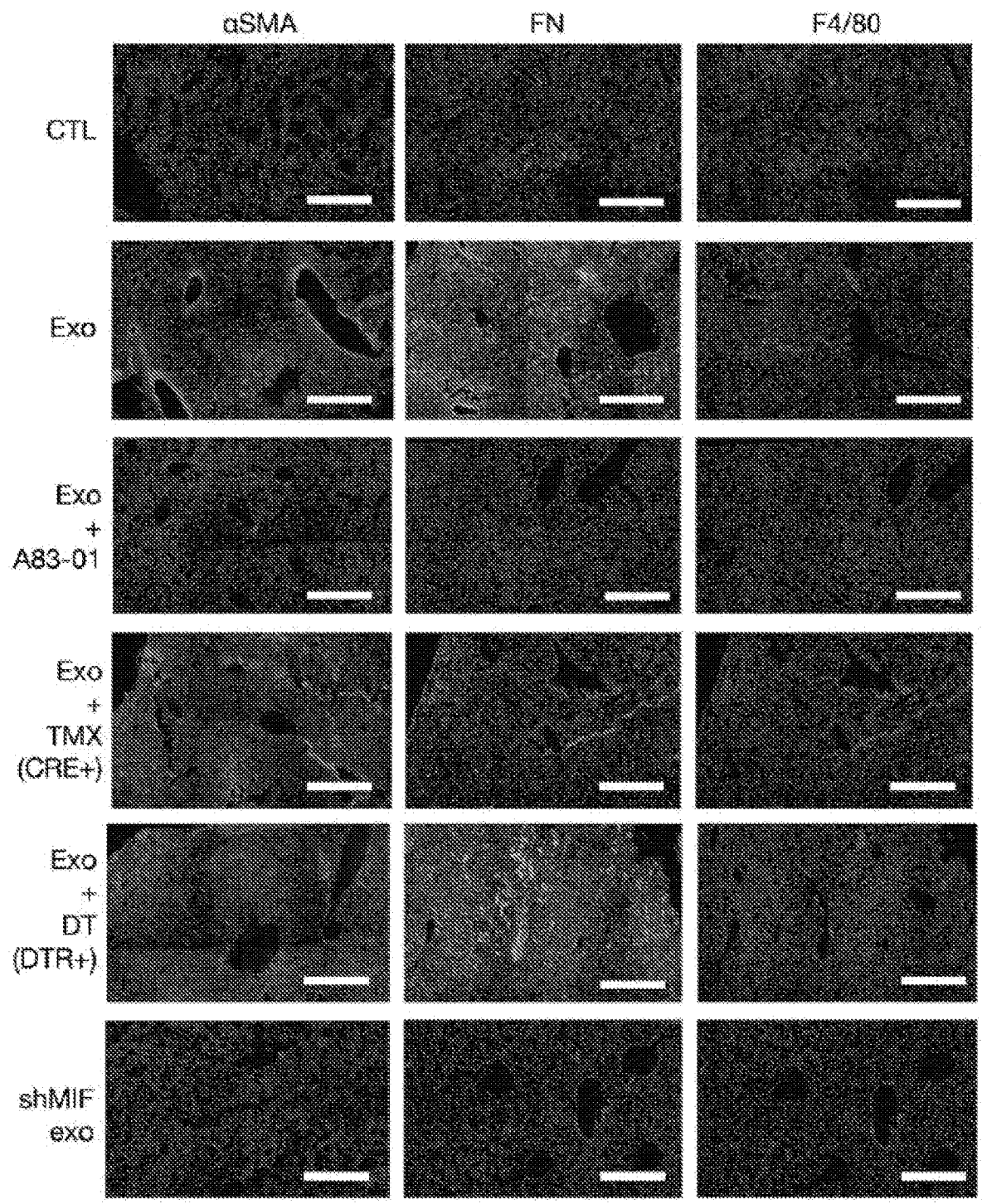
FIG. 7 is a low magnification overview of αSMA (left column), FN (middle column) and F4/80 (right column) expression in the liver of mice educated with PBS (CTL), PAN02 exosomes (Exo), Exo in combination with the TGFβR inhibitor A83-01 (Exo+A83-01), Exo in combination with tamoxifen in the FN conditional knockout mouse model (Exo+TMX (CRE$^+$), Exo in combination with Diphtheria toxin (DT) in the CD11b-DTR (Exo+DT(DTR$^+$), and Exo derived from MIF knockdown pancreatic cancer cells (shMIF Exo). Scale bars, 500 µm.

Example 4—Macrophage Recruitment to the Liver Pre-Metastatic Niche Follows TGFβ Signaling-Induced Fibronectin Upregulation Upon KC education with PDAC-derived exosomes in vitro, TGFβ was among the most highly upregulated soluble factor related to liver fibrosis and hStCs activation (60-148% increase) produced by KCs (FIG. 2E and FIG. 1F). TGFβ mediates fibrogenesis by inducing hStC activation and myofibroblast differentiation, leading to ECM protein production (Achyut & Yang, "Transforming Growth Factor-Beta in the Gastrointestinal and Hepatic Tumor Microenvironment," *Gastroenterology* 141:1167-1178 (2011); Hayashi & Sakai, "Biological Significance of Local TGF-Beta Activation in Liver Diseases," *Frontiers Physiol.* 3:12 (2012); Wight & Potter-Perigo, "The Extracellular Matrix: An Active or Passive Player in Fibrosis? *American Journal of Physiology Gastrointestinal and Liver Physiology* 301:G950-955 (2011); Gressner et al.," "Roles of TGF-Beta in Hepatic Fibrosis," *Frontiers in Bioscience: A Journal and Virtual Library* 7:d793-807 (2002); Cong et al., "Cell Signals Influencing Hepatic Fibrosis," *Int. J. Hepatol.* 2012:158547 (2012), which are hereby incorporated by reference in their entirety). It was hypothesized that KC-derived TGFβ might be responsible for inducing FN production by hStCs (Kawelke et al., "Fibronectin Protects From Excessive Liver Fibrosis by Modulating the Availability of and Responsiveness of Stellate Cells to Active TGF-Beta," *PloS one* 6:e28181 (2011); Xu et al., "Gene Expression and Synthesis of Fibronectin Isoforms in Rat Hepatic Stellate Cells. Comparison With Liver Parenchymal Cells and Skin Fibroblasts," *J. Pathol.* 183:90-98 (1997), which are hereby incorporated by reference in their entirety). Consistent with this hypothesis, treatment with a TGF-beta type I receptor inhibitor (A83-01) (Tojo et al., "The ALK-5 Inhibitor A-83-01 Inhibits Smad Signaling and Epithelial-to-Mesenchymal Transition by Transforming Growth Factor-Beta," *Cancer Sci.* 96:791-800 (2005), which is hereby incorporated by reference in its entirety) during the three-week course of PAN02 exosome education reduced the frequency of αSMA$^+$ hStCs, FN deposition, and F4/80$^+$ macrophage migration to the liver (FIG. 6 and FIG. 7). Thus, FN deposition and macrophage recruitment are both TGFβ-dependent steps that occur during liver pre-metastatic niche formation.

Figures 8A, 8B, 8C:
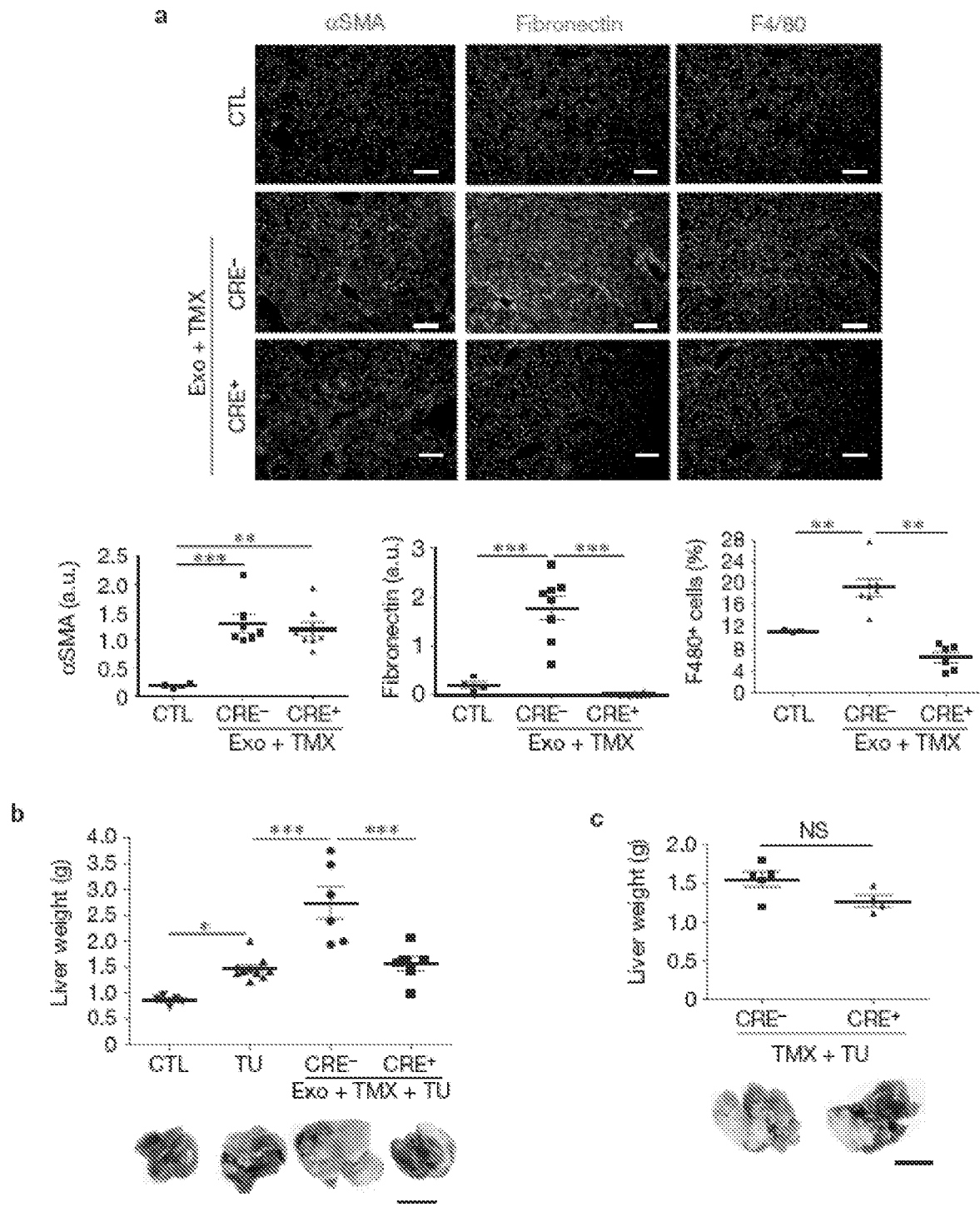
FIGS. 8A-8F depict the roles of fibronectin and macrophages in PAN02 exosome-mediated liver pre-metastatic niche formation.

To further define the sequential events involved in liver pre-metastatic niche development, a conditional FN knock-out murine model was used in which tamoxifen-driven Cre recombinase expression depletes FN during PAN02 exosome education. It was verified that FN deposition in the liver was reduced to control Rosa-CreER$^-$; Fn$^{fl/fl}$ levels upon tamoxifen treatment of Rosa-CreER$^+$; Fn$^{fl/fl}$, while αSMA expression was not affected (FIG. 8). Interestingly, FN depletion led to a reduction in the frequency of F4/80$^+$ macrophages in the liver, demonstrating that FN deposition is required to increase macrophage frequency in the pre-metastatic liver (FIG. 8A). To test if FN depletion plays a functional role in PDAC liver metastasis, PAN02 cells were intra-splenically injected into tamoxifen-treated Rosa- CreER$^+$; Fn$^{fl/fl}$ and control (Rosa-CreER$^-$; Fn$^{fl/fl}$) mice educated with PAN02 exosomes. Consistent with the hypothesis that FN plays a critical role in liver pre-metastatic niche formation, FN depletion during the three-week PAN02 exosome education step reverted the pro-metastatic phenotype to resemble livers harvested from PBS-educated PAN02 tumor bearing mice (FIG. 8B). Of note, reduction of FN levels in non-educated mice using the same system did not affect baseline liver metastasis (FIG. 8C). These results confirm that FN is required for PDAC exosome mediated liver pre-metastatic niche formation.

Figures 8D, 8E, 8F:
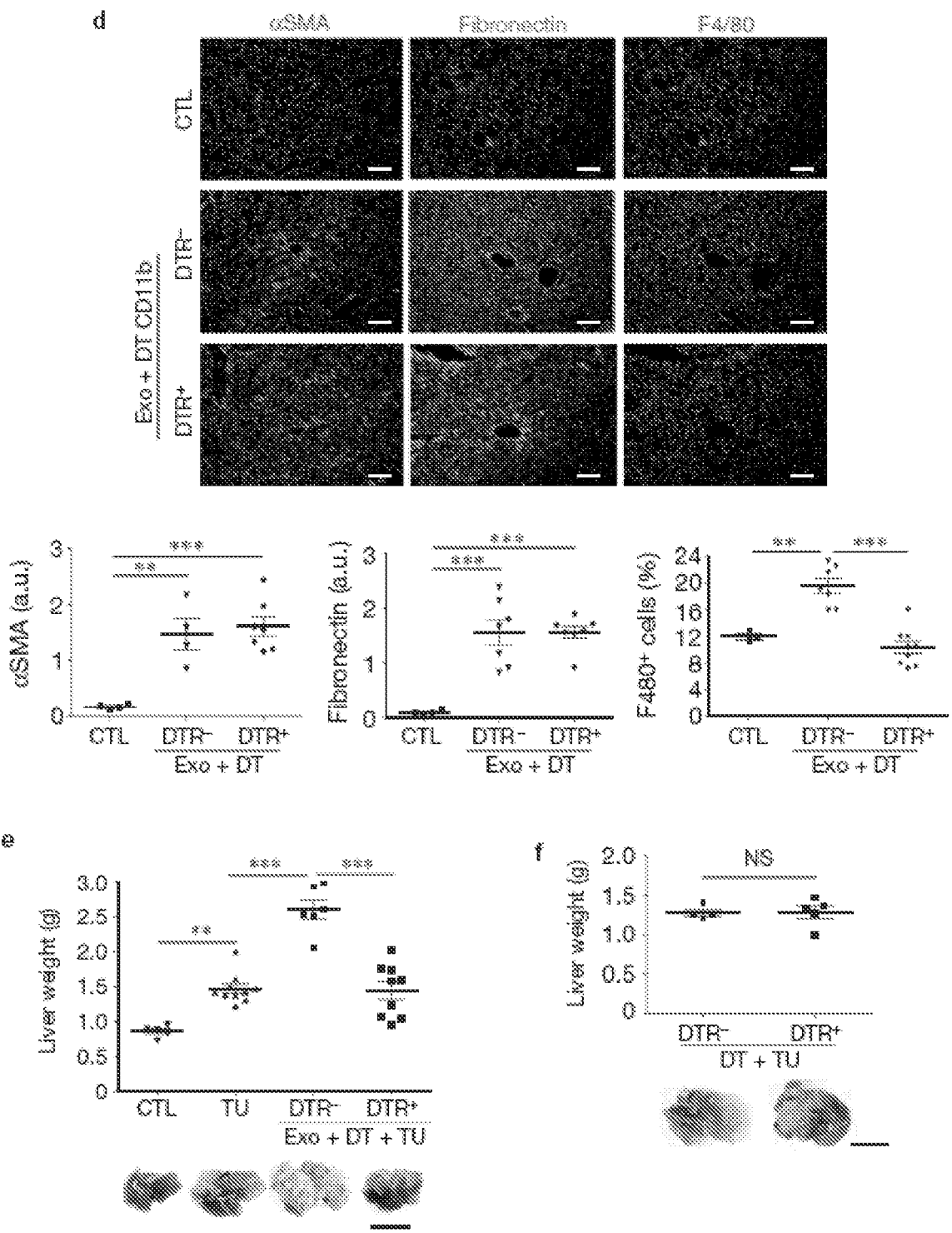
Figure 9:
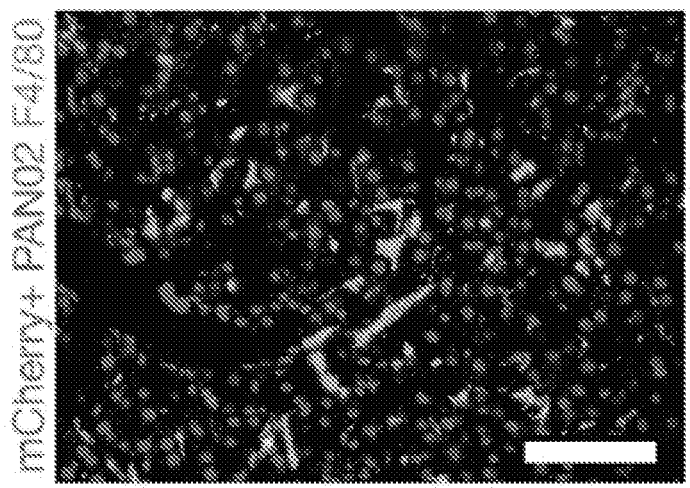
FIG. 9 shows metastatic pancreatic cells localize adjacent to liver macrophages. Fluorescence microscopy analysis of F4/80+ staining and mCherry+ PAN02 cell localization in early metastatic lesions of mice educated with PAN02 exosomes reveals close association between metastatic cells and liver macrophages. Scale bar, 150 µm.

Example 5—Macrophage Ablation Blocks the Pro-Metastatic Effect of Pancreatic Ductal Adenocarcinoma-Derived Exosomes in the Liver Bone-marrow macrophages are recruited to the liver during the early stages of exosome-mediated liver pre-metastatic niche formation. Therefore, whether macrophages present in the liver pre-metastatic niche are physically associated with liver metastatic lesions was investigated. To this end, disseminated PAN02 cells were tracked in the liver of mice educated for three weeks with PAN02 exosomes, 24 hours after splenic injection. Metastatic cells localized adjacent to F4/80$^+$ macrophages (FIG. 9). Next, whether macrophages are required for liver pre-metastatic niche formation was determined. To distinguish between direct effects of FN deposition and FN-mediated effects on liver F4/80$^+$ cell frequency during PAN02 exosome-mediated liver pre-metastatic niche formation and liver metastasis, a diphtheria toxin (DT)-inducible system that transiently depletes CD11b$^+$ cells (including macrophages and neutrophils) expressing the DT receptor (DTR) (Duffield et al., "Selective Depletion of Macrophages Reveals Distinct, Opposing Roles During Liver Injury and Repair," *J. Clin. Invest.* 115:56-65 (2005), which is hereby incorporated by reference in its entirety) was used. DT treatment during the second week of PAN02 exosome education significantly reduced the frequency of F4/80$^+$ macrophages without affecting αSMA$^+$ hStC or FN levels in the liver (FIG. 8D and FIG. 7). The effects of macrophage depletion on metastatic progression was examined by injecting PAN02 cells into exosome-educated mice depleted of CD11b$^+$ cells. Macrophage depletion was sufficient to revert the effects of PAN02 exosome education on liver metastasis (FIG. 8E). Of note, reduction of macrophage levels in non-educated mice using the same approach did not alter baseline liver metastasis (FIG. 8F). Taken together, these results suggest that macrophages are required for liver pre-metastatic niche-dependent metastasis formation.

Figures 10A, 10B:
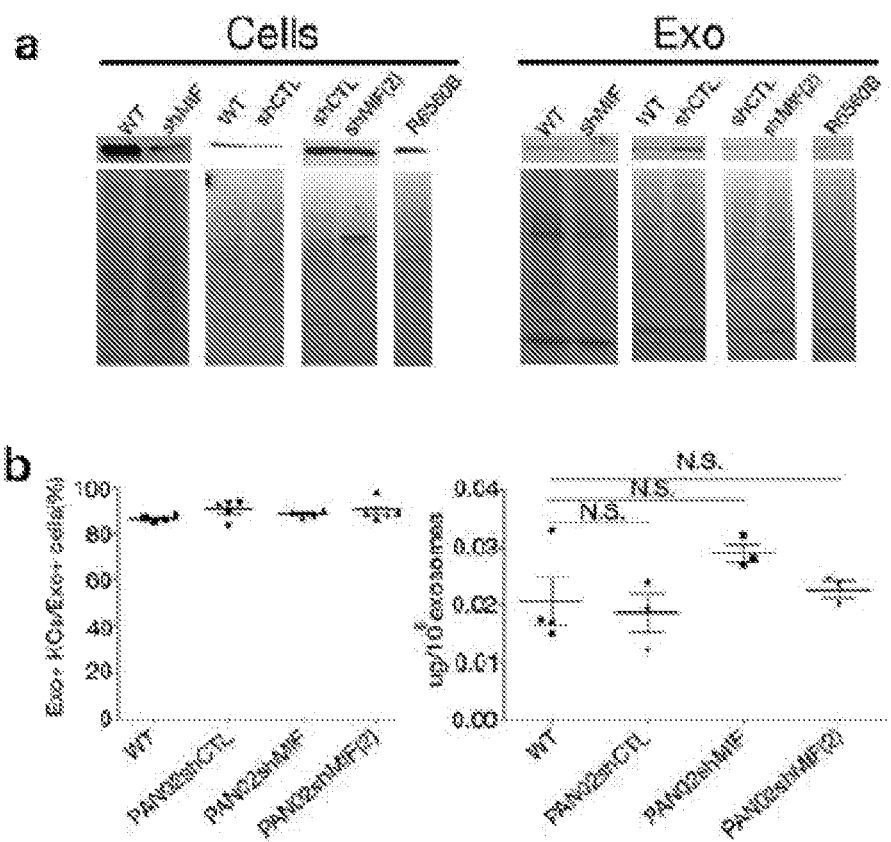
FIGS. 10A-10D show an evaluation of MIF knockdown exosome uptake by KCs in vivo and the functional consequences on hStC activation and early metastasis.
Figures 10C, 10D:
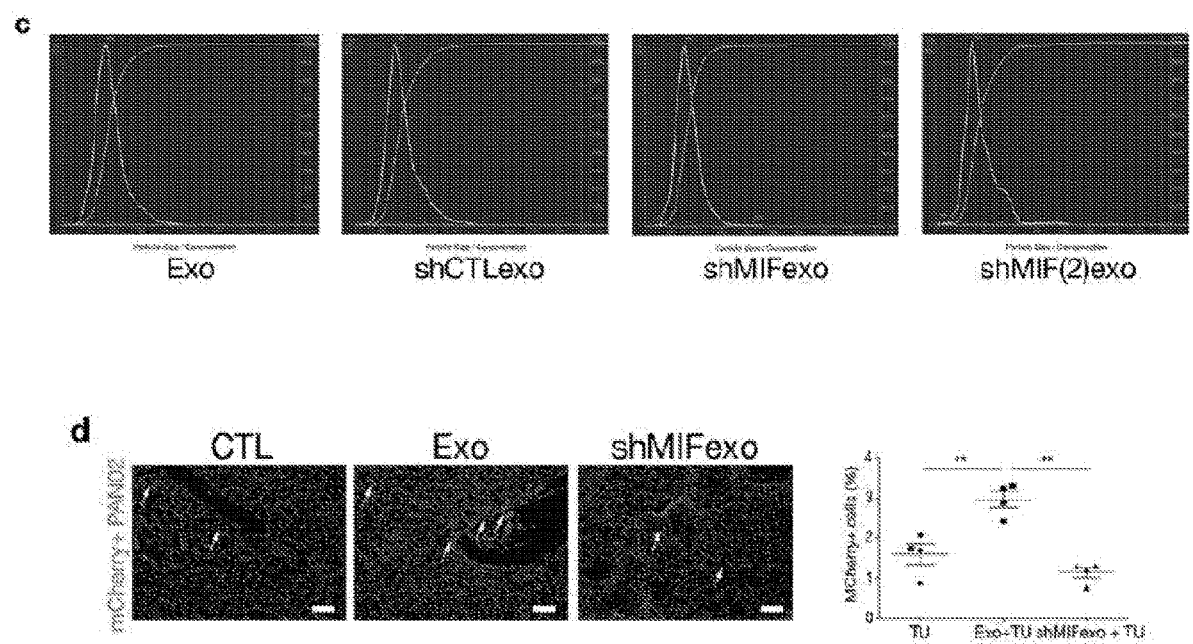
Figure 11A:
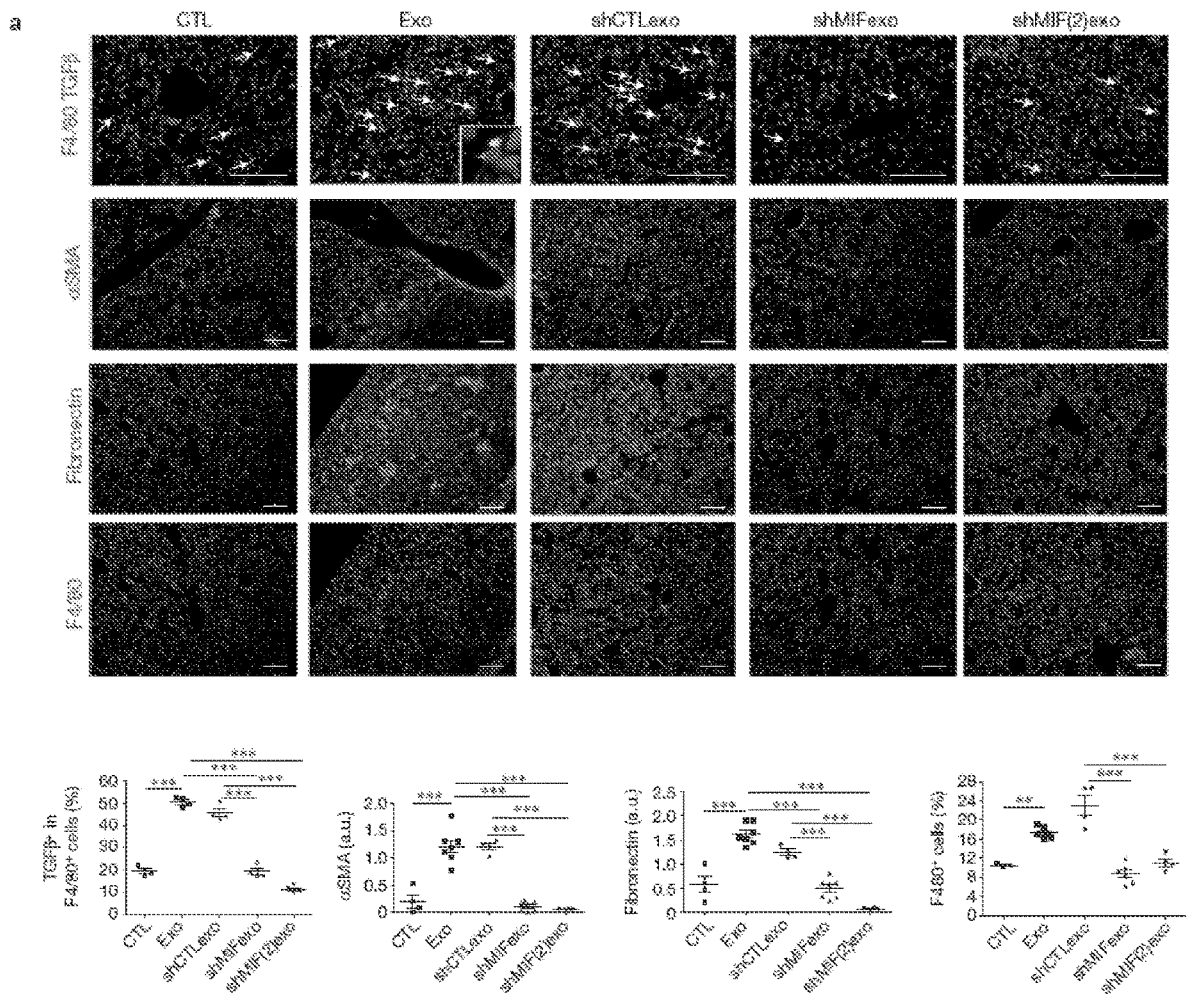
FIGS. 11A-11D show MIF-expressing PAN02 exosomes induce liver pre-metastatic niche formation.

Example 6—MIF Depletion in Pancreatic Ductal Adenocarcinoma-Derived Exosomes Inhibits Liver Pre-Metastatic Niche Initiation To gain insight into the mechanisms through which PDAC-derived exosomes promote KC activation and subsequent liver pre-metastatic niche formation, pancreatic exosome mass spectrometry data was mined for potential inflammatory mediators. Among the candidates with previously described roles in either or both macrophage activation and inflammatory modulation, macrophage migration inhibitory factor (MIF) was found to be highly expressed in PDAC-derived exosomes. MIF knockdown in PAN02 cells did not affect exosome size, quantity of protein per exosome, or the binding of these exosomes to liver CD11b$^+$ F4/80$^+$ cells (FIGS. 10A-10C). However, the effects of MIF knockdown on liver pre-metastatic niche formation were striking, as evidenced by a pronounced reduction of TGFβ expression in F4/80$^+$ cells and of αSMA in hStCs (FIG. 11A and FIG. 7). Moreover, MIF knockdown decreased both FN deposition and F4/80$^+$ macrophage frequency (FIG. 11A and FIG. 7). Additionally, a reduction in tumor cell retention after 24 hours was observed in mice educated with PAN02 MIF knockdown exosomes, compared to control PAN02 exosomes (FIG. 10D). These results suggest that MIF orchestrates the sequential events in PDAC-derived exosome-induced liver pre-metastatic niche formation.

Figures 11B, 11C, 11D:
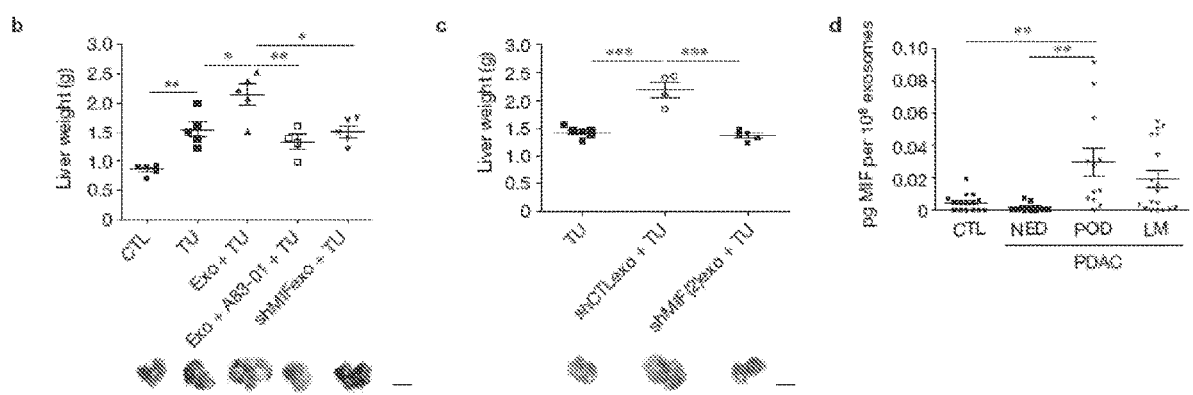

To further evaluate the functional role of exosomal MIF in liver metastatic progression, the consequences of intrasplenic injection of PAN02 cells into non-educated mice versus pre-educated mice that were treated with either PAN02 or PAN02 MIF knockdown exosomes for three weeks were compared. In addition to preventing KC education and the sequential steps in liver pre-metastatic niche induction by PAN02 exosomes (FIG. 11A), and analogous to TGFβ1R signaling inhibition by A83-01 (FIG. 6), MIF knockdown also reduced the ability of PAN02 exosomes to promote liver metastasis (FIGS. 11B and 11C). Control lentiviral vectors did not alter the effects of PAN02 exosomes on liver pre-metastatic niche formation (FIGS. 11A and 11C). Collectively this data demonstrates that exosomal MIF is mediating the increase in metastatic burden observed upon PDAC-derived exosome education.

To determine the clinical relevance of these findings, the variation in MIF levels between exosomes isolated from plasma samples of control healthy subjects and PDAC patients with liver metastasis, with either no evidence of disease five years post diagnosis (NED) or progression of disease post diagnosis (POD) was determined. POD patients expressed significantly higher exosomal MIF levels compared to NED patients and healthy control subjects, indicating that exosomal MIF can be used as a biomarker of PDAC prognosis. A trend toward lower MIF levels was apparent in exosomes isolated from PDAC patients with liver metastasis versus those with POD, although the difference between patient groups was not statistically significant (FIG. 11D). Taken together, these findings indicate that MIF-expressing exosomes are essential for liver pre-metastatic niche initiation and efficient liver metastasis.

Figures 12A, 12B:
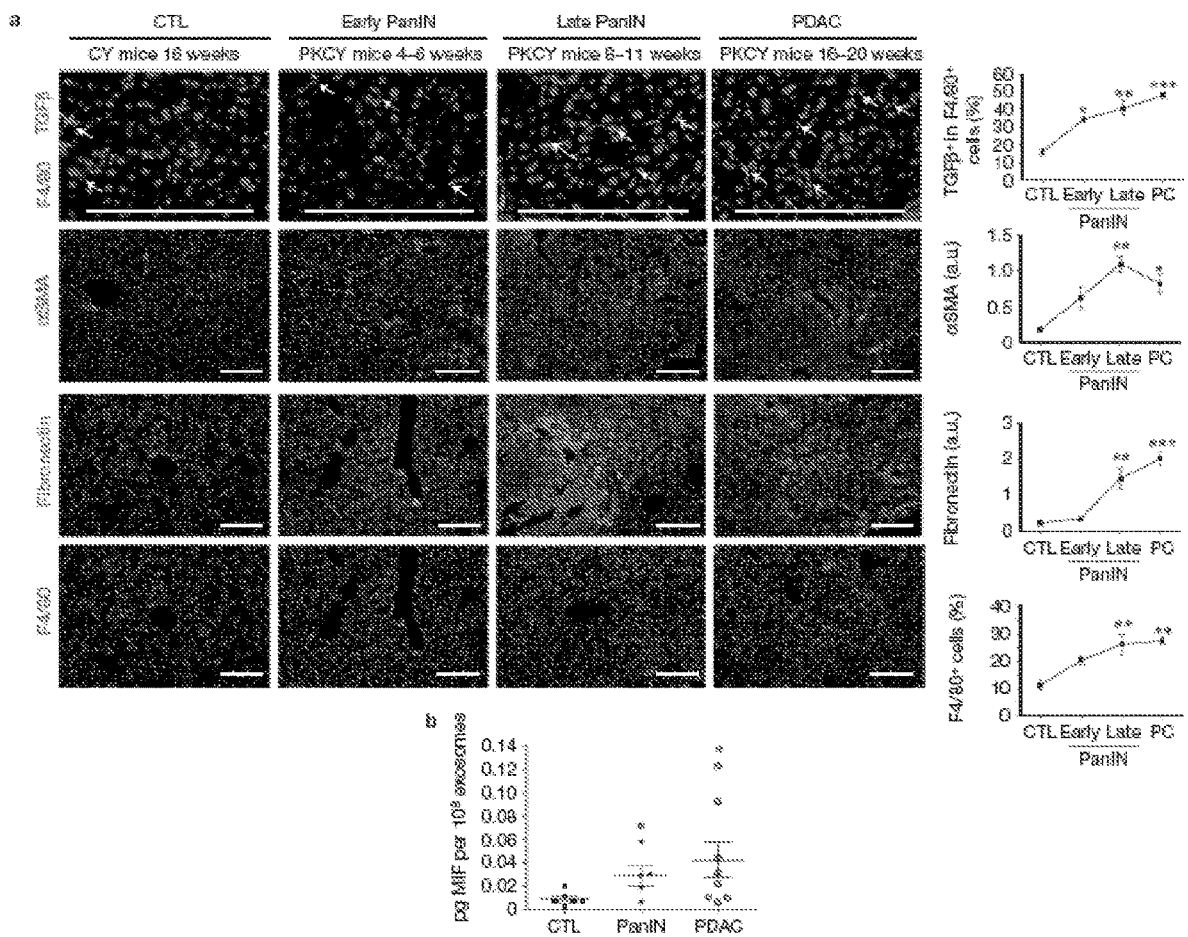
FIG. 12A depicts immunofluorescence quantification of αSMA and FN expression in arbitrary units (A.U.) and F4/80+ cell frequency in livers of control CY mice at 16 weeks (wks) (CTL), PKCY mice at early and late PanIN phases (4-6 and 8-11 wks, respectively), and PDAC livers (16-20 wks). Upregulation of αSMA, FN, and increased frequency of F4/80+ cells can be observed starting at the PanIN stages; n=4 (all CTL; all early PanIN; all late PanIN; PDAC TGFβ and αSMA) and n=5 (PDAC FN and F4/80) mice pooled from three experiments. *P<0.001, P<0.01, *P<0.05 by ANOVA when compared to CTL. Scale bars, 200 µm.
FIG. 12B shows levels of MIF in exosomes isolated from plasma of CY and PKCY mice, at PanIN (both early and late) and PDAC stages measured by ELISA; n=5 (PanIN), n=6 (CTL), and n=8 (PDAC) mice plasma samples pooled from two experiments. *P<0.05 by ANOVA when compared to CTL. All data are represented as mean±s.e.m.

Example 7—Liver Pre-Metastatic Niche Formation Precedes the Establishment of Pancreatic Ductal Adenocarcinoma Lesions To further characterize changes in the liver niche during metastatic progression, the livers of PKCY mice that develop PDAC with reproducible kinetics were analyzed, starting with "early" PanIN (Pancreatic Intraepithelial Neoplasia) lesions at 4-6 weeks, more advanced PanINs at 8-11 weeks, and invasive cancers at 16-20 weeks that metastasizes to the liver (Rhim et al., "EMT and Dissemination Precede Pancreatic Tumor Formation," *Cell* 148:349-361 (2012), which is hereby incorporated by reference in its entirety). Livers isolated from mice that do not develop pancreatic lesions (Cre transgenic mice lacking activating p53 Kras mutations, from hereon referred to as CY mice) were used as controls. An increase in αSMA$^+$ cells (6-fold), FN accumulation (7-fold), and an infiltration of F4/80$^+$ cells (2-fold) in PKCY mice was found at the late PanIN stage (FIG. 12A). Next, TGFβ expression levels were evaluated during pancreatic cancer progression in PKCY mice. Importantly, it was found that TGFβ was upregulated in KCs during the early PanIN stage (2-fold), suggesting that PDAC-derived exosomes play a role during the pre-tumoral stages of liver pre-metastatic niche formation (FIG. 12A). Finally, to determine whether exosomal MIF protein levels correlate with the progression of pancreatic lesions, exosomes isolated from the plasma of PKCY mice were evaluated at different stages of pancreatic lesion progression. MIF levels were increased in exosomes from mice with PDAC when compared to exosomes from healthy control mice (FIG. 12B). Interestingly, the increase in exosomal MIF levels was already detectable in exosomes isolated from mice with PanIN lesions (early or late stage) (FIG. 12B). Collectively, these results demonstrate that changes in MIF levels in PDAC-derived exosomes reflect liver pre-metastatic niche formation during pre-malignant stages of PDAC metastatic progression.

Figure 14:
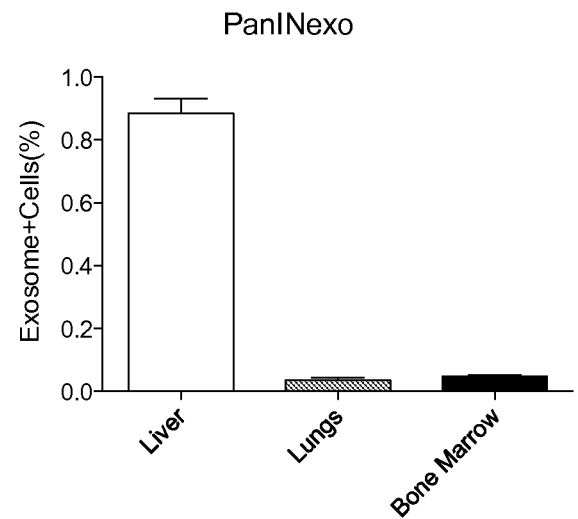
FIG. 14 is a graph showing in vivo distribution of exosomes isolated from the mouse pancreatic intraepithelial neoplasia (PanIN) primary cultures to the liver, lungs, and bone marrow.
Figure 15:
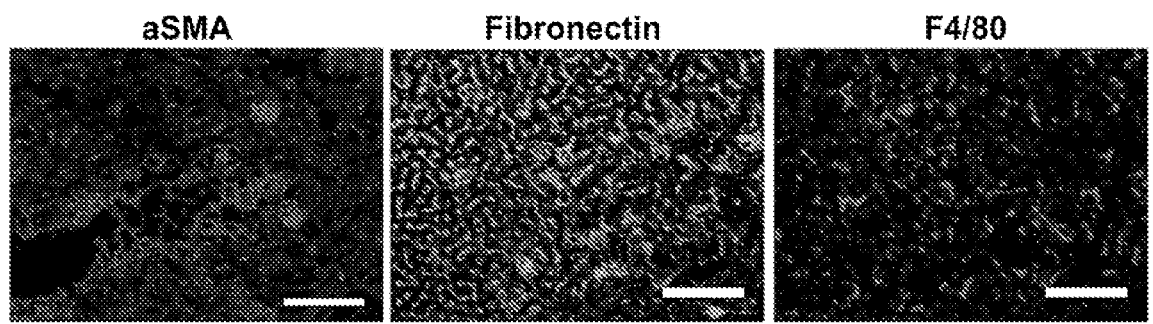
FIG. 15 is a panel of immunofluorescence images showing in vivo liver pre-metastatic niche formation by exosomes isolated from murine PanIN primary cultures.

Consistent with these results, FIG. 14 shows that in mice educated with murine PanIN exosomes (exosomes isolated prior to the pancreatic carcinoma stage), the exosomes preferentially migrate to the liver, where >90% of the liver cells incorporating PanIN exosomes are $CD11b^+/F4/80^+$ Kupffer cells. The PanIN exosomes are capable of inducing pre-metastatic liver formation as indicated by the increase in αSMA expression, fibronectin accumulation, and infiltration of F4/80+ cells in the liver of the educated mice (see FIG. 15).

Discussion of Examples 1-7

Figure 13:
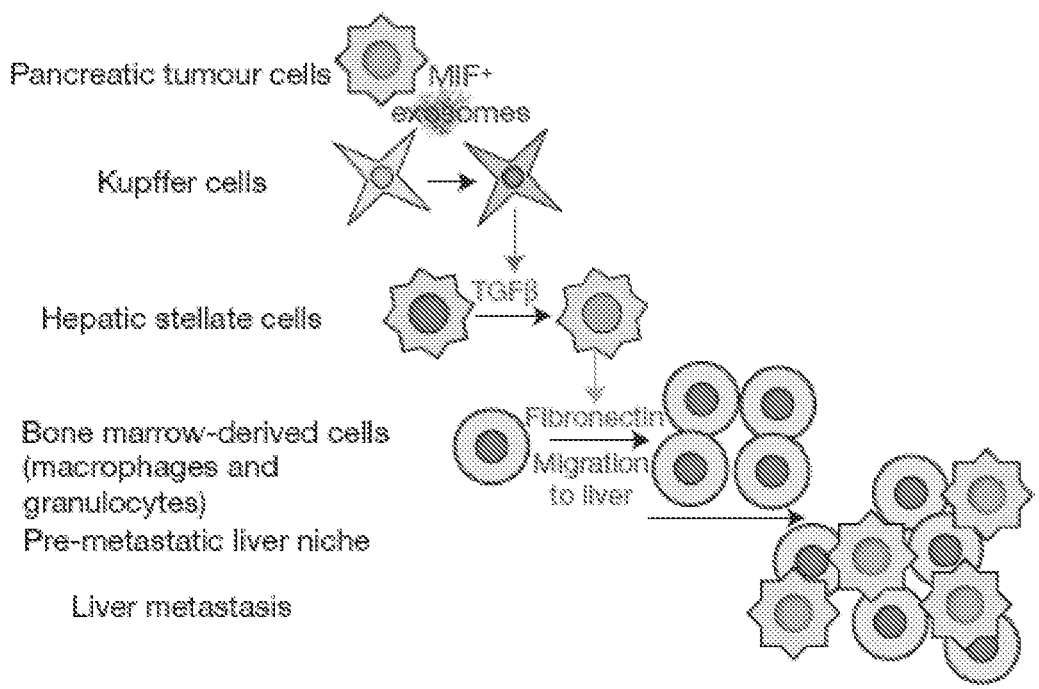
FIG. 13 is a model for the sequential steps in liver pre-metastatic niche formation induced by pancreatic ductal adenocarcinoma-derived exosomes. Education with MIF+ PDAC-derived exosomes, which bind predominantly to Kupffer cells in the liver, induces TGFβ production by these cells. TGFβ activates hStCs, which in turn upregulate FN. Bone marrow-derived cells (i.e. macrophages) bind to FN-enriched hepatic sites, ultimately leading to liver pre-metastatic niche formation.

Circulating exosomes can be used as biological markers for pancreatic cancers (Arscott & Camphausen, "EGFR Isoforms in Exosomes as a Novel Method for Biomarker Discovery in Pancreatic Cancer," *Biomark. Med.* 5:821 (2011); Lau et al., "Role of Pancreatic Cancer-Derived Exosomes in Salivary Biomarker Development," *J. Biol. Chem.* 288:26888-26897 (2013), which are hereby incorporated by reference in their entirety). However, the cellular and molecular mechanisms through which PDAC-derived exosomes affect metastasis have yet to be determined. Here, delineated for the first time, are the sequential steps of liver pre-metastatic niche formation by PDAC-derived exosomes. PDAC-derived exosomes induce TGFβ signaling in KCs, leading to activation of hStCs and ECM remodeling. In turn, FN accumulation promotes an influx of BM-derived macrophages (and potentially neutrophils) to the liver, providing a favorable niche for liver metastasis (FIG. 13). Importantly, this stepwise progression was also demonstrated in a spontaneous murine model of pancreatic cancer, the PKCY mouse model, in which key early liver pre-metastatic niche features (such as hStC activation, FN accumulation, and macrophage recruitment to the liver) are already evident during the PanIN stages.

Unbiased mass spectrometry analysis of PDAC-derived exosome protein cargo led to the identification of MIF as a candidate mediator of liver education. Although one study has described MIF as an anti-fibrotic factor in a chemically induced liver fibrosis model (Heinrichs et al., "Macrophage Migration Inhibitory Factor (MIF) Exerts Antifibrotic Effects in Experimental Liver Fibrosis via CD74," *Proc. Nat'l. Acad. Sci. U.S.A.* 108:17444-17449 (2011), which is hereby incorporated by reference in its entirety), MIF is a well-known mediator of liver inflammation and fibrosis, of BM cell recruitment to the liver and liver metastasis, and furthermore MIF tissue and plasma levels correlate with PDAC aggressiveness (Barnes et al., "Macrophage Migration Inhibitory Factor Contributes to Ethanol-Induced Liver Injury by Mediating Cell Injury, Steatohepatitis, and Steatosis," *Hepatology* 57:1980-1991 (2013); Funamizu et al., "Macrophage Migration Inhibitory Factor Induces Epithelial to Mesenchymal Transition, Enhances Tumor Aggressiveness and Predicts Clinical Outcome in Resected Pancreatic Ductal Adenocarcinoma," *International J. Cancer. Journal International du Cancer* (2012); Nanji et al., "Macrophage Migration Inhibitory Factor Expression in Male and Female Ethanol-Fed Rats," *Journal of Interferon & Cytokine Research: The Official Journal of the International Society for Interferon and Cytokine Research* 21:1055-1062 (2001); Shin et al., "Stromal Cell-Derived Factor-1 alpha and Macrophage Migration-Inhibitory Factor Induce Metastatic Behavior in CXCR4-Expressing Colon Cancer Cells," *International J. Mol. Med.* 30:1537-1543 (2012); Zhang et al., "Macrophage Migration Inhibitory Factor Expression Correlates With Inflammatory Changes in Human Chronic Hepatitis B Infection," *Liver International: Official Journal of the International Association for the Study of the Liver* 25:571-579 (2005), which are hereby incorporated by reference in their entirety). The data presented herein show that MIF-positive PDAC exosomes bind preferentially to the liver, delivering their cargo specifically to Kupffer cells. This exosome-mediated transport of MIF is distinct from the circulation of this protein in a soluble form, as it permits highly specific and enhanced delivery of MIF to Kupffer cells. Thus, soluble MIF levels could not predict the ability of this protein to bind to Kupffer cells and induce liver pre-metastatic niche formation.

The functional experiments in murine models of pancreatic ductal adenocarcinoma demonstrate that exosomal MIF upregulation is an early event during cancer progression and can be detected in plasma-derived exosomes isolated from mice with pre-tumoral pancreatic lesions. Importantly, high exosomal MIF levels were present in plasma from patients with stage I PDAC, prior to liver metastasis, indicating its potential prognostic value. In contrast, exosomal MIF levels had a bimodal distribution in patients with established liver metastatic disease. The presence of low exosomal MIF levels in a subset of PDAC patients with liver metastasis indicates that MIF-dependent mechanisms may be more important during earlier stages of liver metastasis. Taken together, these observations indicate that exosomal MIF levels can serve as an early biomarker for liver pre-metastatic niche formation and a prognostic factor for metastatic risk in patients with pre-tumoral lesions, such as pancreatitis, PanINs, intra-ductal papillary mucinous neoplasms (IPMNs), and pre-metastatic PDACs. Moreover, these results also indicate that high MIF levels may be an indicator of risk for liver pre-metastatic niche formation and liver metastasis in other gastrointestinal tract tumors, such as colorectal and gastric cancer. MIF inhibition by either small molecules or neutralizing antibodies has been shown to prevent macrophage activation, TGFβ expression, and tissue fibrosis (Adamali et al., "Macrophage Migration Inhibitory Factor Enzymatic Activity, Lung Inflammation, and Cystic Fibrosis," *Am. J. Respiratory Crit. Care Med.* 186:162-169 (2012); Kobayashi et al., "Prevention of Lethal Acute Hepatic Failure by Antimacrophage Migration Inhibitory Factor Antibody in Mice Treated With Bacille Calmette-Guerin and Lipopolysaccharide," *Hepatology* 29:1752-1759 (1999); Yaddanapudi et al., "Control of Tumor-Associated Macrophage Alternative Activation by Macrophage Migration Inhibitory Factor," *J. Immunol.* 190:2984-2993 (2013); Chen et al., "ISO-1, a Macrophage Migration Inhibitory Factor Antagonist, Inhibits Airway Remodeling in a Murine Model of Chronic Asthma," *Mol. Med.* 16:400-408 (2010), which are hereby incorporated by reference in their entirety).

High levels of TGFβ in patients with pancreatic cancers is associated with poor prognosis (Javle et al., "Biomarkers of TGF-Beta Signaling Pathway and Prognosis of Pancreatic Cancer," *PloS one* 9:e85942 (2014), which is hereby incorporated by reference in its entirety). Anti-TGFβ compounds have shown efficacy in preclinical and clinical studies (Ellermeier et al., "Therapeutic Efficacy of Bifunctional siRNA Combining TGF-Beta1 Silencing With RIG-I Activation in Pancreatic Cancer," *Cancer Res.* 73:1709-1720 (2013); Gaspar et al., "Inhibition of Transforming Growth Factor Beta Signaling Reduces Pancreatic Adenocarcinoma Growth and Invasiveness," *Mol. Pharmacol.* 72:152-161 (2007), which are hereby incorporated by reference in their entirety), suppressing liver metastasis by acting on both incoming tumor cells and the liver microenvironment (Melisi et al., "LY2109761, a Novel Transforming Growth Factor Beta Receptor Type I and Type II Dual Inhibitor, as a Therapeutic Approach to Suppressing Pancreatic Cancer Metastasis," *Mol. Cancer Therapeutics* 7:829-840 (2008), which is hereby incorporated by reference in its entirety). However, systemic TGFβ inhibition carries a substantial risk for patients as this pathway is implicated in multiple homeostatic processes and may also have tumor-suppressor functions depending on the tumor stage and stromal activation status (Pickup et al., "The Roles of TGFbeta in the Tumour Microenvironment," *Nature Reviews. Cancer* 13:788-799 (2013); Ijichi et al., "Aggressive Pancreatic Ductal Adenocarcinoma in Mice Caused by Pancreas-Specific Blockade of Transforming Growth Factor-Beta Signaling in Cooperation with Active Kras Expression," *Genes & Development* 20:3147-3160 (2006); Hezel et al., "TGF-Beta and Alphavbeta6 Integrin Act in a Common Pathway to Suppress Pancreatic Cancer Progression," *Cancer Re.* 72:4840-4845 (2012), which are hereby incorporated by reference in their entirety). Although the data presented herein suggest that targeting TGFβ signaling may be beneficial for preventing liver pre-metastatic niche formation, given the context-dependent roles of TGFβ, its potential anti-tumorigenic effects need to be excluded before TGFβ inhibitors are considered for metastasis prevention in PDAC patients in the clinic.

Several studies have correlated KC (Bayon et al., "Role of Kupffer Cells in Arresting Circulating Tumor Cells and Controlling Metastatic Growth in the Liver," *Hepatology* 23:1224-1231 (1996); Kruse et al., "Macrophages Promote Tumour Growth and Liver Metastasis in an Orthotopic Syngeneic Mouse Model of Colon Cancer," *Int. J. Colorectal Disease* 28:1337-1349 (2013); Wen et al., "Bimodal Role of Kupffer Cells During Colorectal Cancer Liver Metastasis," *Cancer Biology & Therapy* 14:606-613 (2013), which are hereby incorporated by reference in their entirety) and ECM changes (Grzesiak et al., Knockdown of the Beta(1) Integrin Subunit Reduces Primary Tumor Growth and Inhibits Pancreatic Cancer Metastasis," *Int. J. Cancer. Journal international du Cancer* 129:2905-2915 (2011); Saito et al., "Inhibition of Hepatic Metastasis in Mice Treated With Cell-Binding Domain of Human Fibronectin and Angiogenesis Inhibitor TNP-470." *Int. J. Clin. Oncol.* 6:215-220 (2001); Zvibel et al., "Extracellular Matrix Modulates Expression of Growth Factors and Growth-Factor Receptors in Liver-Colonizing Colon-Cancer Cell Lines," *Int. J. Cancer. Journal international du Cancer* 77:295-301 (1998), which are hereby incorporated by reference in their entirety) with circulating tumor cell arrest and liver metastasis. In addition, myeloid cell recruitment to the liver was also shown to precede liver metastasis (Porembka et al., "Pancreatic Adenocarcinoma Induces Bone Marrow Mobilization of Myeloid-Derived Suppressor Cells Which Promote Primary Tumor Growth," *Cancer Immunol. Immunother.: CII* 61:1373-1385 (2012); Yamamoto et al., "TSU68 Prevents Liver Metastasis of Colon Cancer Xenografts by Modulating the Premetastatic Niche," *Cancer Res.* 68:9754-9762 (2008); Zhang et al., "Development and Characterization of a Reliable Mouse Model of Colorectal Cancer Metastasis to the Liver," *Clin. Exper. Metastasis* 30:903-918 (2013); Seubert et al., "Tissue Inhibitor of Metalloproteinases (TIMP)-1 Creates a Premetastatic Niche in the Liver Through SDF-1/CXCR4-Dependent Neutrophil Recruitment in Mice," *Hepatology* 61:238-248 (2015), which are hereby incorporated by reference in their entirety). As demonstrated here for the first time, liver pre-metastatic niche formation during PDAC metastasis depends on tumor exosome-derived MIF. Moreover, this process is driven by TGFβ-signaling, FN deposition, and recruitment of BM-derived macrophages to future liver metastatic niches. By individually targeting MIF, FN, and macrophages, the effects of PDAC-derived exosome education was reverted at various steps during liver pre-metastatic niche formation. Strategies aimed at targeting these particular molecules (TGFβ, MIF, FN) and cell types (BM-derived cells) have been previously explored (Kruse et al., "Macrophages Promote Tumour Growth and Liver Metastasis in an Orthotopic Syngeneic Mouse Model of Colon Cancer," *Int. J. Colorectal Disease* 28:1337-1349 (2013); Kato et al., "A New Type of Antimetastatic Peptide Derived From Fibronectin," *Clin. Cancer Res.: An Official Journal of the American Association for Cancer Research* 8:2455-2462 (2002); Bissell, D. M., "Therapy for Hepatic Fibrosis: Revisiting the Preclinical Models," *Clinics and Res. Hepatol. Gastroenterol.* 35:521-525 (2011); Korpal & Kang, "Targeting the Transforming Growth Factor-Beta Signalling Pathway in Metastatic Cancer," *European J. Cancer* 46:1232-1240 (2010); Noy & Pollard, "Tumor-Associated Macrophages: From Mechanisms to Therapy. *Immunity* 41:49-61 (2014), which are hereby incorporated by reference in their entirety). The detailed dissection of the sequential events of PDAC metastasis initiation shown herein provides an understanding of how tumor secreted factors, specifically exosomes, orchestrate this process and these findings open new avenues for early detection, prevention, and therapeutic intervention.

Figure 16:
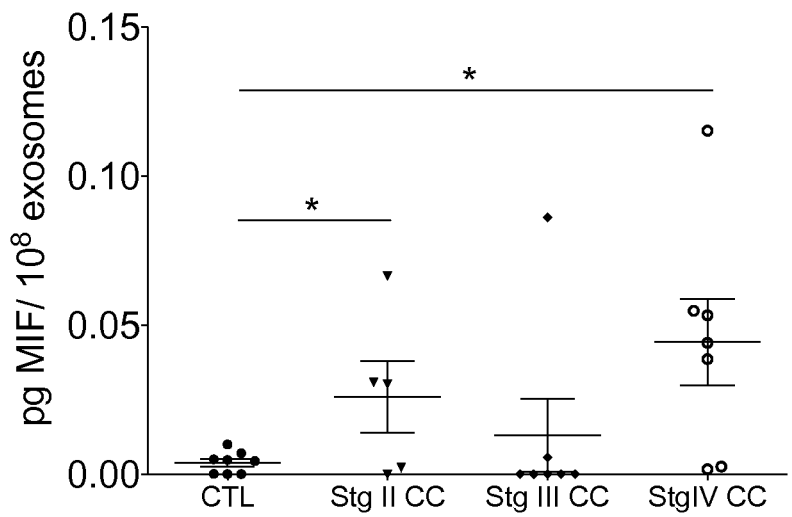
FIG. 16 is a graph showing levels of exosomal MIF expression in patients having various stages of colorectal cancer and control patients.
Figure 17A:
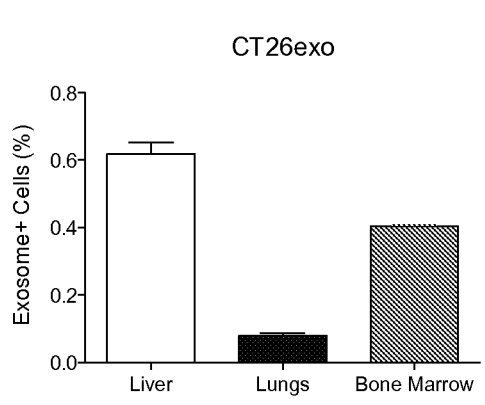
FIG. 17A is a graph showing in vivo distribution of exosomes isolated from the mouse colorectal cancel cell lineage CT26 to the liver, lungs, and bone marrow.
Figure 17B:
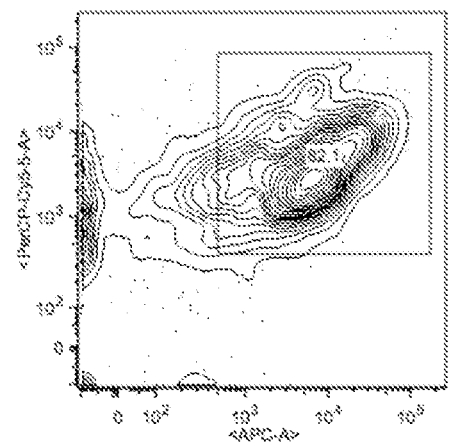
FIG. 17B is showing the specific incorporation of colorectal cancer exosomes by CD11b+ F4/80+ Kupffer cells in the liver.
Figure 18:
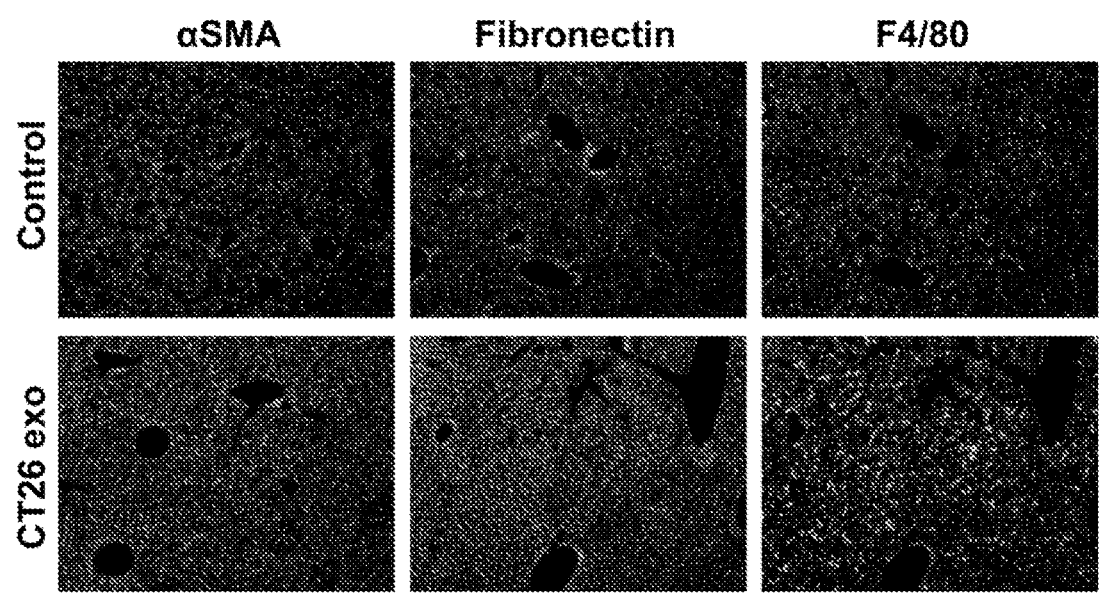
FIG. 18 is a panel of immunofluorescence images showing liver pre-metastatic niche formation by murine colorectal cancel cell lineage CT26 exosomes.

Example 8—Colorectal Cancer-Derived Exosomes Preferentially Fuse with Kupffer Cells and Enhance Metastatic Burden in Liver Like pancreatic cancer derived exosome, colorectal and gastric cancer derived exosomes are also capable of inducing liver metastatic disease. FIG. 16 is a graph showing an increase in exosomal MIF expression in plasma exosomes isolated from colorectal patients at various stages of the disease as compared to exosomes isolated from tumor free plasma (CTL). FIG. 17A shows that in mice educated with exosomes isolated from the mouse CT26 colorectal cancer cell lineage, the exosomes preferentially distribute to the liver and are incorporated specifically by CD11b$^+$/F4/80$^+$ Kupffer cells. FIG. 17B shows that colorectal cancer exosomes fuse specifically with CD11b$^+$/F4/80$^+$ kupffer cells in the liver. The colorectal cancer cell exosomes are capable of inducing pre-metastatic liver formation as indicated by the increase in αSMA expression, fibronectin accumulation, and infiltration of F4/80+ cells in the liver of the educated mice (see FIG. 18).

Example 9—Exosomal Mediators of Liver Pre-Metastatic Niche Formation

In addition to MIF, other potential exosomal mediators of liver premetastatic niche formation were investigated in not only pancreatic cancer derived exosomes, but also colorectal and gastric cancer derived exosomes. Table 6 below provides a list of the exosomal markers of metastatic liver disease that have both prognostic and therapeutic utility in accordance with the methods of the present invention.

TABLE 6

Exosomal Mediators of Metastatic Liver Disease

| | | Pancreatic Cancer | | | | | | COLORECTAL CANCER | |
| --- | --- | --- | --- | --- | --- | --- | --- | --- | --- |
| | | MOUSE | | HUMAN | | | | MOUSE | |
| Symbol | Enterez Gene Name | PAN02 | PDAC | BxPc3 | HPAF-II | AsPC-1 | Mia-PaCa2 | CT26 | CT26-R3 |
| ANXA1 | Annexin A1 | + | + | + | + | + | + | + | + |
| CD44 | CD44 | + | + | + | − | − | + | + | + |
| CD47 | CD47 | + | + | + | + | − | + | + | + |
| CDH1 | Cadherin 1 | + | + | + | + | − | − | + | − |
| FLNA | Filamin A | + | + | + | + | − | + | + | + |
| HMGB1 | High mobility group box 1 | + | − | − | − | − | − | + | + |
| ITGB3 | Integrin Beta 3 | + | + | + | − | − | − | + | + |
| LGALS1 | lectin, galactoside-binding, soluble, 1 | + | + | + | − | + | + | + | + |
| LGALS3 | lectin, galactoside-binding, soluble, 3 | + | + | + | + | + | + | + | + |
| MIF | macrophage migration inhibitory factor | + | + | + | + | + | + | + | + |
| MMP14 | matrix metalloproteinase 14 | + | − | + | − | + | + | − | − |
| PLAUR | plasminogen activator, urokinase receptor | + | + | − | − | − | − | − | − |
| PTGS2 | prostagiandin-endoperoxide symthase 2 | + | − | − | − | − | − | − | + |
| RAC1 | ras-related C3 botulinum toxin substrate 1 | + | − | + | + | + | + | + | + |

| | | COLORECTAL CANCER HUMAN | | | GASTRIC CANCER HUMAN | | |
| --- | --- | --- | --- | --- | --- | --- | --- |
| Symbol | Enterez Gene Name | HT29 | HCT116 | SW620 | SNU-1 | SNU-16 | % |
| ANXA1 | Annexin A1 | + | + | − | + | + | 69.2307692 |
| CD44 | CD44 | + | + | − | − | + | 69.2307692 |
| CD47 | CD47 | − | − | − | + | − | 61.5384615 |
| CDH1 | Cadherin 1 | − | + | + | − | + | 61.5384615 |
| FLNA | Filamin A | + | + | + | + | − | 92.3076923 |
| HMGB1 | High mobility group box 1 | + | + | + | − | − | 46.1538462 |
| ITGB3 | Integrin Beta 3 | − | + | + | − | − | 53.8461538 |
| LGALS1 | lectin, galactoside-binding, soluble, 1 | + | + | + | + | − | 84.6153846 |
| LGALS3 | lectin, galactoside-binding, soluble, 3 | + | + | + | + | + | 100 |
| MIF | mecrophage migration inhibitory factor | + | + | + | + | + | 100 |
| MMP14 | matrix metalloproteinase 14 | − | − | − | − | − | 30.7692308 |
| PLAUR | plasminogen activator, urokinase receptor | − | + | − | − | − | 23.0769231 |
| PTGS2 | prostagiandin-endoperoxide symthase 2 | − | − | − | − | − | 15.3846154 |
| RAC1 | ras-related C3 botulinum toxin substrate 1 | + | + | + | + | − | 84.6153846 |

What is claimed is:

1. A method comprising:
   selecting a subject having a pancreatic lesion;
   obtaining, from the selected subject, a sample containing exosomes;
   isolating exosomes from said sample; and
   detecting, in said isolated exosomes, protein levels of Annexin A1 (ANXA1), filamin A (FLNA), lectin galactoside-binding soluble 3 (LGALS3), and macrophage migration inhibitory factor (MIF).

2. The method of claim 1, wherein the subject has a pre-tumoral pancreatic lesion.

3. The method of claim 1, wherein said detecting comprises:
   detecting exosomal levels of the one or more proteins in the sample using an immunoassay.

4. A method of inhibiting metastatic liver disease in a subject, said method comprising:
   selecting a subject having a pancreatic lesion and increased exosomal levels of proteins Annexin A1 (ANXA1), filamin A (FLNA), lectin galactoside-binding soluble 3 (LGALS3), and macrophage migration inhibitory factor (MIF) relative to exosomal levels of said proteins in a subject not having a pancreatic lesion, and
   administering to the selected subject, an inhibitor of liver pre-metastatic niche (LPMN) formation in an amount effective to inhibit metastatic liver disease in the subject.

5. The method of claim 4, wherein the inhibitor of LPMN formation is selected from the group consisting of a MIF inhibitor, a TGFβ inhibitor, a fibronectin inhibitor, a macrophage inhibitor, a liver fibrosis inhibitor and any combination thereof.

6. The method of claim 5, wherein the MIF inhibitor is an anti-MIF antibody or a small molecule MIF antagonist.

7. The method of claim 4, wherein the selected subject has a pre-tumoral pancreatic lesion.

* * * * *

SEQUENCE LISTING

```
<160> NUMBER OF SEQ ID NOS: 5

<210> SEQ ID NO 1
<211> LENGTH: 49
<212> TYPE: PRT
<213> ORGANISM: Artificial
<220> FEATURE:
<223> OTHER INFORMATION: Fibronectin binding peptide

<400> SEQUENCE: 1

Lys Asp Gln Ser Pro Leu Ala Gly Glu Ser Gly Glu Thr Glu Tyr Ile
1               5                   10                  15

Thr Glu Val Tyr Gly Asn Gln Gln Asn Pro Val Asp Ile Asp Lys Lys
                20                  25                  30

Leu Pro Asn Glu Thr Gly Phe Ser Gly Asn Met Val Glu Thr Glu Asp
            35                  40                  45

Thr
```

```
<210> SEQ ID NO 2
<211> LENGTH: 96
<212> TYPE: PRT
<213> ORGANISM: Artificial
<220> FEATURE:
<223> OTHER INFORMATION: Fibronectin binding peptide

<400> SEQUENCE: 2

Arg Asn Pro His Leu Met Gly Ile Gly Gly Leu Ala Gly Glu Ser
1               5                   10                  15

Gly Glu Thr Thr Pro Lys Pro Gly Gln Thr Gly Gln Gly Pro Val
                20                  25                  30

Ile Glu Thr Thr Glu Asp Thr Gln Lys Gly Met Ser Gly Gln Ser Gly
            35                  40                  45

Gly Thr Ile Glu Ser Glu Asn Thr Lys Lys Pro Glu Val Met Ile Gly
        50                  55                  60

Gly Gln Gly Gln Thr Ile Glu Thr Thr Glu Asp Thr Gln Lys Gly Met
65                  70                  75                  80

Ser Gly Gln Ser Gly Gly Thr Ile Glu Ser Glu Asp Thr Lys Lys Pro
                85                  90                  95

<210> SEQ ID NO 3
<211> LENGTH: 75
<212> TYPE: PRT
<213> ORGANISM: Artificial
<220> FEATURE:
<223> OTHER INFORMATION: Fibronectin binding peptide

<400> SEQUENCE: 3

Tyr Glu Gln Gly Gly Asn Ile Val Asp Ile Asp Phe Asp Ser Val Pro
1               5                   10                  15

Gln Ile His Gly Gln Asn Lys Gly Asn Gln Ser Phe Glu Glu Asp Thr
                20                  25                  30

Glu Lys Asp Lys Pro Lys Tyr Glu His Gly Gly Asn Ile Ile Asp Ile
            35                  40                  45

Asp Phe Asp Ser Val Pro His Ile His Gly Phe Asn Lys His Thr Glu
        50                  55                  60

Ile Ile Glu Glu Asp Thr Asn Lys Asp Lys Pro
65                  70                  75

<210> SEQ ID NO 4
<211> LENGTH: 14
<212> TYPE: PRT
<213> ORGANISM: Artificial
<220> FEATURE:
<223> OTHER INFORMATION: TGFBeta1 inhibitory peptide

<400> SEQUENCE: 4

Val Leu Ala Leu Tyr Asn Gln His Asn Pro Gly Ala Ser Ala
1               5                   10

<210> SEQ ID NO 5
<211> LENGTH: 12
<212> TYPE: PRT
<213> ORGANISM: Artificial
<220> FEATURE:
<223> OTHER INFORMATION: TGFBeta1 inhibitory peptide

<400> SEQUENCE: 5

Thr Ser Leu Asp Ala Ser Ile Ile Trp Ala Met Met
1               5                   10
```